US012121571B2

(12) United States Patent
Choi et al.

(10) Patent No.: US 12,121,571 B2
(45) Date of Patent: Oct. 22, 2024

(54) RECOMBINANT L-ASPARAGINASE

(71) Applicant: Jazz Pharmaceuticals Ireland Ltd., Dublin (IE)

(72) Inventors: Mi Rim Choi, Encino, CA (US); Tong Lin, Palo Alto, CA (US); Jeffrey Silverman, Burlingame, CA (US)

(73) Assignee: Jazz Pharmaceuticals Ireland Ltd., Dublin (IE)

( * ) Notice: Subject to any disclaimer, the term of this patent is extended or adjusted under 35 U.S.C. 154(b) by 0 days.

(21) Appl. No.: 17/078,376

(22) Filed: Oct. 23, 2020

(65) Prior Publication Data
US 2021/0308237 A1  Oct. 7, 2021

Related U.S. Application Data

(60) Provisional application No. 63/047,222, filed on Jul. 1, 2020, provisional application No. 62/926,201, filed on Oct. 25, 2019.

(51) Int. Cl.
| | |
|---|---|
| *A61K 38/50* | (2006.01) |
| *A61K 9/00* | (2006.01) |
| *A61P 1/00* | (2006.01) |

(52) U.S. Cl.
CPC ............ *A61K 38/50* (2013.01); *A61K 9/0019* (2013.01); *A61P 1/00* (2018.01); *C12Y 305/01001* (2013.01)

(58) Field of Classification Search
None
See application file for complete search history.

(56) References Cited

U.S. PATENT DOCUMENTS

| | | | |
|---|---|---|---|
| 9,221,882 B2 | 12/2015 | Skerra et al. | |
| 9,322,008 B2 | 4/2016 | Kundu et al. | |
| 10,406,235 B2 | 9/2019 | Ma et al. | |
| 11,141,468 B2 | 10/2021 | Aguera et al. | |
| 2019/0010192 A1 | 1/2019 | Binder et al. | |
| 2019/0127742 A1* | 5/2019 | Coleman | C12N 9/82 |
| 2020/0277379 A1 | 9/2020 | Bostwick et al. | |
| 2021/0401953 A1 | 12/2021 | Sellers et al. | |
| 2022/0080033 A1 | 3/2022 | Mukherjee et al. | |

FOREIGN PATENT DOCUMENTS

| | | |
|---|---|---|
| CN | 102657852 A | 9/2012 |
| WO | WO 2011/003633 A1 | 1/2011 |
| WO | WO 2019/109018 A1 | 6/2019 |
| WO | WO2020/089743 A1 | 5/2020 |
| WO | WO2021/032997 A1 | 2/2021 |

OTHER PUBLICATIONS

Erwinaze, "Highlights of Prescribing Information: Erwinaze", pp. 1-9. (Year: 2016).*
Covini et al., "Expanding Targets for a Metabolic Therapy of Cancer: L-Asparaginase", Recent Patents on Anti-Cancer Drug Discovery, vol. 7, p. 4-13. (Year: 2012).*
Balcão et al., "Structural and functional stabilization of protein entities: state of the art", Advanced Drug Delivery Reviews, vol. 93, pp. 25-41. (Year: 2015).*
Rowe et al., "Handbook of Pharmaceutical Excipients: Sodium Phosphate, Monobasic", 6th Edition, London, p. 659-661. (Year: 2009).*
Lomilino et al., "Asparagine synthetase: Function, structure, and role in disease", Journal of Biological Chemistry, vol. 292(49), pp. 19952-19958. (Year: 2017).*
Sun et al., "SLC1A3 contributes to L-asparaginase resistance in solid tumors", The EMBO Journal, vol. 38, pp. 1-16. (Year: 2019).*
Hernandez-Illas M, Lin T, Rey A, et al. A Phase 1 Study of the Safety, Tolerability, and Pharmacokinetics of Recombinant Crisantaspase Produced in Pseudomonas fluorescens (RC-P) in Healthy Adults [abstract]. Blood. 2019; 134(suppl 1):3817 pp. 1-4.
Lin T, Dumas T, Kaullen J, et al. Population Pharmacokinetic (PK) Model Development and Simulation for Recombinant Crisantaspase Produced in Pseudomonas fluorescens (RC-P) [abstract]. Clinical Pharmacology & Therapeutics. 2020;107(suppl 1):S5-S121. PII-056.
Lin T, Hernandez-Illas M, Rey A, et al. A Randomized Phase 1 Study of the Safety, Tolerability, and Pharmacokinetics of Recombinant Erwinia Asparaginase (JZP-458) in Healthy Adult Volunteers. Clinical and Translational Science. doi:10.1111/cts.12947 pp. 1-32.
Lin T, Dumas T, Kaullen J, et al. Population Pharmacokinetic Model Development and Simulation for Recombinant Erwinia Asparaginase Produced in Pseudomonas fluorescens (JZP-458) pp. 1-25.
Maese L, Rizzari C, Coleman R, et al. Can recombinant technology address asparaginase Erwinia chrysanthemi shortages? Submitted to Pediatric Blood & Cancer pp. 1-28. Maese L, Rau RE, Raetz R, et al. Open-label, Multicenter, Phase 2/3 Study of Recombinant Crisantaspase Produced in Pseudomonas fluorescens (RC-P) in Patients with Acute Lymphoblastic Leukemia (ALL) or Lymphoblastic Lymphoma (LBL) Following Hypersensitivity to *Escherichia coli*-derived Asparaginases [abstract]. Blood. 2019;134(suppl 1):2586 pp. 1-3.
Maese L, Rau RE, Raetz R, et al. A Phase 2/3 study of JZP-458 in patients with acute lymphoblastic leukemia (ALL)/lymphoblastic lymphoma (LBL) who are hypersensitive to *E. coli*-derived asparaginases [abstract]. J Clin Oncol. 2020;38(15_suppl). TPS7568 pp. 1-3.
Adamson, RH et al. Evaluation of the embryotoxic activity of L asparaginase. Arch Int Pharmacodyn 1970;186(2):310-20.

(Continued)

*Primary Examiner* — Michelle F. Paguio Frising
*Assistant Examiner* — Grant C Currens
(74) *Attorney, Agent, or Firm* — DLA Piper LLP (US)

(57) ABSTRACT

The present invention provides compositions and methods for treating a disease treatable by asparagine depletion in a human subject comprising administering to a human subject a recombinant L-asparaginase.

32 Claims, 33 Drawing Sheets
Specification includes a Sequence Listing.

(56) References Cited

OTHER PUBLICATIONS

American Cancer Society. Types of Non-Hodgkin Lymphoma in Children; dated Jan. 27, 2016. Available at: https://www.cancer.org/cancer/childhood-non-hodgkin-lymphoma/treating/by-stage.html. Accessed Mar. 20, 2020. 23 pages.

Ashworth, Lae et al., Comparison of the L-Asparaginases from *Escherichia coli* and *Erwinia carotovora* as immunosuppressants. Cancer Res 1974;34:1353-9.

Asparlas, Summary Basis of Approval. Application #761102, Approval Date: Dec. 20, 2018 https://www.accessdata.fda.gov/drugsatfda_docs/nda/2018/761102Orig1s000TOC.cfm. 2 pages.

Asselin, B et al., Asparaginase pharmacokinetics and implications of therapeutic drug monitoring. Leukemia & lymphoma. Aug. 3, 2015; 56(8):2273-80.

Avramis, Vi et al., A randomized comparison of native *Escherichia coli* asparaginase and polyethylene glycol conjugated asparaginase for treatment of children with newly diagnosed standard-risk acute lymphoblastic leukemia: a Children's Cancer Group study. Blood, The Journal of the American Society of Hematology. Mar. 1, 20025;99(6):1986-94.

Ballerini, A et al. Pharmacodynamic effects in the cerebrospinal fluid of rats after intravenous administration of different asparaginase formulations. Cancer Chemother Pharmacol Jun. 2017;79(6):1267-1271. doi: 10.1007/s00280-017-3307-8.

Barry, E et al., Favorable outcome for adolescents with acute lymphoblastic leukemia treated on Dana-Farber Cancer Institute acute lymphoblastic leukemia consortium protocols. Journal of clinical oncology. Mar. 1, 2007;25(7):813-9.

Bassan, R et al., Lymphoblastic lymphoma: an updated review on biology, diagnosis, and treatment. European journal of Haematology. May 2016; 96(5):447-60.

Benbough, Je et al. The effect of chemical modification of L asparaginase on its persistence in circulating blood of animals. Biochem Pharmacol 1979;28:833.

Berenbaum, MC. Immunosuppression by L-asparaginase. Nature Feb. 7, 1970;225(5232):550-2. doi:10.1038/225550a0.

Blazek, R et al., Improvement in the persistence of microbial asparaginase and glutaminase in the circulation of the rat by chemical modifications. Biochim Biophys Acta 1981;677:220-4.

Borek, D et al., Sequence analysis of enzymes with asparaginase activity. Acta Biochim Pol 2001;48(4):893-902.

Caruso, V et al., Thrombotic complications in childhood acute lymphoblastic leukemia: a meta-analysis of 17 prospective studies comprising 1752 pediatric patients. Blood. Oct. 1, 2006; 108(7):2216-22.

Celle, G et al. Toxic and immunodepressive effects of L-asparaginase from *E. coli* and from Erwinia carotovora following chronic administration in rats. Arzneimittelforschung 1977;27(11):2046-50.

Chen, Q. et al. Autophagy suppression potentiates the anti-glioblastoma effect of asparaginase in vitro and in vivo. Oncotarget 2017;8(53):91052-66.

Chien, WW et al., Pharmacology, immunogenicity, and efficacy of a novel pegylated recombinant *Erwinia chrysanthemi*-derived L-asparaginase. Invest New Drugs 2014;32:795-805.

Chiu, M et al., Glutamine depletion by crisantaspase hinders the growth of human hepatocellular carcinoma xenografts. Br J Cancer 2014;111:1159-67.

Covini, D. et al. Expanding targets for a metabolic therapy of cancer: L asparaginase. Recent Pat Anticancer Drug Discov 2012;7:4-13.

Dana-Farber Cancer Institute: Childhood Lymphoblastic Lymphoma. Available at: https://www.dana-farber.org/childhood-lymphoblastic-lymphoma/. Accessed Feb. 8, 2021.

Davies, B et al., Physiological parameters in laboratory animals and humans. Pharm Res 1993;10(7):1093-95.

DeAngelo, DJ et al., Long-term outcome of a pediatric-inspired regimen used for adults aged 18-50 years with newly diagnosed acute lymphoblastic leukemia. Leukemia. Mar. 2015; 29(3):526-34.

Durden, DL et al., Kinetic analysis of hepatotoxicity associated with antineoplastic asparaginases. Cancer Res 1983;43(4):1602-5.

Duval, M et al., Comparison of *Escherichia coli*-asparaginase with *Erwinia*-asparaginase in the treatment of childhood lymphoid malignancies: Results of a randomized European Organisation for Research and Treatment of Cancer-Children's Leukemia Group phase 3 trial. Blood 2002;99:2734-9.

Emadi, A et al., Asparaginase in the treatment of non-ALL hematologic malignancies Cancer Chemother Pharmacol 2014;73:875-83.

Erwinaze® (asparaginase Erwinia chrysanthemi) Prescribing Information, 2011 (withdrawn 2021). Jazz Pharmaceuticals, Inc.; Palo Alto, CA.

European Medicines Agency (EMA). Guideline on bioanalytical method validation. Jul. 21, 2011 (Effective: Feb. 1, 2012) Available at: https://www.ema.europa.eu/en/bioanalytical-method-validation.

European Medicines Agency (EMA). Guideline on immunogenicity assessment of therapeutic proteins. May 18, 2017 (Effective: Dec. 1, 2017). Available at: https://www.ema.europa.eu/en/immunogenicity-assessment-biotechnology-derived-therapeutic-proteins.

Figueiredo, L et al., Asparaginase Erwinia chrysanthemi as a component of a multi-agent chemotherapeutic regimen for the treatment of patients with acute lymphoblastic leukemia who have developed hypersensitivity to *E. coli*-derived asparaginase. Expert Review of Hematology. Mar. 3, 2016;9(3):227-34.

Food and Drug Administration (FDA.) Guidance for Industry: Bioanalytical method validation. May 2018.

Food and Drug Administration (FDA). Guidance for Industry: Immunogenicity testing of therapeutic proteins—developing and validating assays for anti-drug antibody detection. Feb. 2019. Available at: https://www.fda.gov/regulatory-information/search-fda-guidance-documents/immunogenicity-testing-therapeutic-protein-products-developing-and-validating-assays-anti-drug.

Hall, JG. The partitioning of L-asparaginase between blood and lymph. In: E Grundmann and Oeltgen HF. Recent Results in Cancer Research, vol. 33. Berlin, East Germany; Springer-Verlag. 1970.

Han, T et al., In vitro blastogenesis inhibited by Erwinia carotovora L-asparaginase. Nat New Biol Sep. 13, 1972;239(89):50-1. doi: 10.1038/newbio239050a0.

Hijiya, N et al., Asparaginase-associated toxicity in children with acute lymphoblastic leukemia. Leukemia & lymphoma. Apr. 2, 2016; 57(4):748-57.

Horowitz et al., Asparagine synthetase activity of mouse leukemias. Science May 3, 1968;160(3827):533-5. doi: 10.1126/science.160.3827.533.

Howard, SC et al., Endocrine complications in pediatric patients with acute lymphoblastic leukemia. Blood reviews. Dec. 1, 2002; 16(4):225-43.

Karamitros, CS et al., Human 60-kDa lysophospholipase contains an N-terminal L-asparaginase domain which is allosterically regulated by L-asparagine. J Biol Chem 2014;289(19):12962-75.

Kearney, SL et al., Clinical course and outcome in children with acute lymphoblastic leukemia and asparaginase-associated pancreatitis. Pediatric Blood & Cancer. Aug. 2009; 53(2):162-7.

KIDD J(a). Regression of transplanted lymphomas induced in vivo by means of normal guinea pig serum. I. Course of transplanted cancers of various kinds in mice and rats given guinea pig serum, horse serum, or rabbit serum. J Exp Med 1953;98:565-82.

KIDD J(b). Regression of transplanted lymphomas induced in vivo by means of normal guinea pig serum. II. Studies on the nature of the active serum constituent: Histological mechanism of the regression: Tests for effects of guinea pig serum on lymphoma cells in vitro: Discussion. J Exp Med 1953;98:583-606.

Knoderer, HM et al., Predicting asparaginase-associated pancreatitis. Pediatric blood & cancer. Oct. 15, 2007; 49(5):634-9.

Kotzia, Ga et al., l-Asparaginase from *Erwinia chrysanthemi* 3937: Cloning, expression and characterization. J Biotechnol 2007;127:657-69.

Leukemia Foundation. Lymphoblastic Lymphoma, dated Jun. 18, 2019. Available at: https://www.leukaemia.org.au/disease-information/lymphomas/non-hodgkin-lymphoma/other-non-hodgkin-lymphomas/lymphoblastic-lymphoma/. Accessed Mar. 18, 2020. 2 pages.

(56) References Cited

OTHER PUBLICATIONS

Liu, C et al., Clinical and genetic risk factors for acute pancreatitis in patients with acute lymphoblastic leukemia. Journal of Clinical Oncology. Jun. 20, 2016; 34(18):2133-2140.

Mayo Clinic. Acute Lymphocytic Leukemia. Available at: https://www.mayoclinic.org/diseases-conditions/acute-lymphocytic-leukemia/symptoms-causes/syc-20369077. Accessed Feb. 8, 2021. 3 pages.

Minetto, P et al., Glutamine-dependence targeting by asparaginase significantly increases anti-myeloma activity of proteasome inhibitors. [Abstract 1796] Blood Dec. 7, 2017;130 (Suppl 1).

Minton, NP et al., Nucleotide sequence of the *Erwinia chrysanthemi* NCPPB 1066 L-asparaginase gene. Gene 1986;46:25-35.

Moghrabi, A et al., Results of the Dana-Farber Cancer Institute All Consortium Protocol 95-01 for children with acute lymphoblastic leukemia. Blood. Feb. 1, 2007;109(3):896-904.

Nachman, JB et al., Augmented post-induction therapy for children with high-risk acute lymphoblastic leukemia and a slow response to initial therapy. New England Journal of Medicine. Jun. 4, 1998;338(23):1663-71.

Neish et al., Inhibition of Rd/3 rat sarcoma by L-asparaginase alone and in combination with sodium para-amino-salicylate. Z Krebsforsch Klin Onkol Cancer Res Clin Oncol 1973;79(2):78-84. doi: 10.1007/BF00284381.

Nguyen, Ha et al., A novel L-asparaginase with low L-glutaminase coactivity is highly efficacious against both T and B cell acute lymphoblastic leukemias in vivo. Cancer Res 2018;78(6):1549-60.

Nomme, J et al., Elucidation of the specific function of the conserved threonine triad responsible for human L-asparaginase autocleavage and substrate hydrolysis. J Mol Biol 2014;426:2471-85.

Ogawa, C. et al., Treatment Outcome of Discontinued L-Asparaginase in Children with Standard-Risk Acute Lymphoblastic Leukemia: Tokyo Children's Cancer Study Group (TCCSG) Study L99-15. Blood 2005; 106 (11):878.

Okusanya, O et al., Intramuscular (IM) or intravenous (IV): Impact of Erwinia asparaginase route of administration on asparaginase activity. Journal of Clinical Oncology 2015; 33:15_suppl, 10031.

P06608, UniProtKB Database. 1988.

Panetta et al., Higher plasma asparaginase activity after intramuscular than intravenous Erwinia asparaginase, Pediatric Blood Cancer 2020:e28244.

Panosyan, EH et al., Asparaginase antibody and asparaginase activity in children with higher-risk acute lymphoblastic leukemia: Children's Cancer Group Study CCG-1961. Journal of Pediatric Hematology/Oncology. Apr. 1, 2004; 26(4):217-26.

Panosyan, EH et al., Deamination of glutamine is a prerequisite for optimal asparagine deamination by asparaginases in vivo (CCG-1961). Anticancer Res Mar.-Apr. 2004;24(2C):1121-5.

Parmentier, JH et al., Glutaminase activity determines cytotoxicity of L-asparaginases on most leukemia cell lines. Leuk Res 2015;39:757-62.

Parsons, SK et al., . Asparaginase-associated lipid abnormalities in children with acute lymphoblastic leukemia. Blood, The Journal of the American Society of Hematology. Mar. 15, 1997; 89(6):1886-95.

Patel, N et al., A dyad of lymphoblastic lysosomal cysteine proteases degrades the antileukemic drug L-asparaginase. J Clin Invest Jul. 2009;119(7):1964-73. doi: 10.1172/JCI37977.

Payne, JH et al., Thrombosis and acute lymphoblastic leukaemia. British journal of haematology. Aug. 2007; 138(4):430-45.

Peng, H. et al., Hypermethylation of CpG islands in the mouse asparagine synthetase gene: relationship to asparaginase sensitivity in lymphoma cells. Partial methylation in normal cells. Br J Cancer 2001;85(6):930-5. doi: 10.1054/bjoc.2001.2000.

Pieters, R et al., L-asparaginase treatment in acute lymphoblastic leukemia: a focus on Erwinia asparaginase. Cancer. Jan. 15, 2011; 117(2):238-49.

Place, AE et al., Intravenous pegylated asparaginase versus intramuscular native *Escherichia coli* L-asparaginase in newly diagnosed childhood acute lymphoblastic leukaemia (DFCI 05-001): a randomised, open-label phase 3 trial. The lancet oncology. Dec. 1, 2015;16(16):1677-90.

Plourde, PV et al., Safety profile of asparaginase Erwinia chrysanthemi in a large compassionate-use trial. Pediatric blood & cancer. Jul. 2014; 61(7):1232-8.

Pui, CH et al., Treatment of acute lymphoblastic leukemia. New England Journal of Medicine. Jan. 12, 2006; 354(2):166-78.

Raetz, EA et al., Tolerability and efficacy of L-asparaginase therapy in pediatric patients with acute lymphoblastic leukemia. J Pediatr Hematol Oncol 2010 32(7):554-63. doi: 10.1097/MPH.0b013e3181e6f003.

Raja, RA et al., Asparaginase-associated pancreatitis in children with acute lymphoblastic leukaemia in the Nopho All 2008 protocol. British journal of haematology. Apr. 2014;165(1):126-33.

Riccardi, R et al., L-asparaginase pharmacokinetics and asparagine levels in cerebrospinal fluid of rhesus monkeys and humans. Cancer Res 1981;41(11 Pt 1):4554-8.

Roberts, J. et al., A comparative study of the antitumor effectiveness of *E. coli* and Erwinia asparaginases. Cancer Biochem Biophys 1976;1:175-8.

Runzi, M et al., Drug-associated pancreatitis: facts and fiction. Pancreas. Jul. 1, 1996; 13(1):100-9.

Rutter, DA et al., The influence of the iso-electric point of L-asparaginase upon its persistence in the blood. Br J Exp Pathol 1971;52:610.

Ryu IH, Long-Term Survival after T-cell Lymphoblastic Lymphoma Treated with One Cycle of Hyper-CVAD Regimen. Cancer Res Treat. 2015; 47(1):115-119.

Sahu, S et al., L-asparaginase (Leunase) induced pancreatitis in childhood acute lymphoblastic leukemia. Pediatric hematology and oncology. Jan. 1, 1998;15(6):533-8.

Sallan, W et al., Influence of intensive asparaginase in the treatment of childhood non-T-cell acute lymphoblastic leukemia. Cancer Research. Nov. 1, 1983; 43(11):5601-7.

Salzer, WL et al., Erwinia asparaginase achieves therapeutic activity after pegaspargase allergy: a report from the Children's Oncology Group. Blood. Jul. 25, 2013; 122(4):507-14.

Salzer, WL et al., Development of asparaginase *Erwinia chrysanthemi* for the treatment of acute lymphoblastic leukemia. Ann NY Acad Sci 2014;1329:81-92.

Salzer, WL et al., Asparaginase activity levels and monitoring in patients with acute lymphoblastic leukemia. Leukemia & lymphoma. Aug. 3, 2018; 59(8):1797-806.

Samarasinghe, S et al., . Incidence and outcome of pancreatitis in children and young adults with acute lymphoblastic leukaemia treated on a contemporary protocol, UKALL 2003. British journal of haematology. Sep. 2013;162(5):710-3.

Sanghez, V et al., Efficacy of asparaginase *Erwinia chrysanthemi* with and without temozolomide against glioma cells and intracranial mouse medulloblastoma. Anticancer Res 2018;38:2627-34.

Serravalle, S et al., Synergistic cytotoxic effect of L-asparaginase combined with decitabine as a demethylating agent in pediatric T-ALL, with specific epigenetic signature. Biomed Res Int 2016; Article ID 1985750, 6 pp. http://dx.doi.org/10.1155/2016/1985750.

Siemers, RF et al., High-dose cytosine arabinoside-associated pancreatitis. Cancer. Oct. 15, 1985; 56(8):1940-2.

Silverman, LB et al., Improved outcome for children with acute lymphoblastic leukemia: results of Dana-Farber Consortium Protocol 91-01. Blood, The Journal of the American Society of Hematology. Mar. 1, 2001; 97(5):1211-8.

Sobin, LH et al., Alterations in protein and nucleic acid metabolism of lymphoma $6C_3$ HED-og cells in mice given guinea pig serum. J Exp Med 1966;123(1):55-74. doi: 10.1084/jem.123.1.55.

Song, P et al., The role of autophagy in asparaginase-induced immune suppression of macrophages Cell Death Dis 2017;8:e2721; doi:10.1038/cddis.2017.144 2017.

Song, P et al., Asparaginase induces apoptosis and cytoprotective autophagy in chronic myeloid leukemia cells. Oncotarget 2015;6(6):3861-73.

Stock, W et al., What determines the outcomes for adolescents and young adults with acute lymphoblastic leukemia treated on cooperative group protocols? A comparison of Children's Cancer Group

(56) References Cited

OTHER PUBLICATIONS and Cancer and Leukemia Group B studies. Blood, The Journal of the American Society of Hematology. Sep. 1, 2008; 112(5):1646-54.
Stock, W et al., Prevention and management of asparaginase/pegasparaginase-associated toxicities in adults and older adolescents: recommendations of an expert panel. Leukemia & Lymphoma. Dec. 1, 2011; 52(12):2237-53.
Stock, W et al., A pediatric regimen for older adolescents and young adults with acute lymphoblastic leukemia: results of CALGB 10403. Blood. Apr. 4, 2019; 133(14):1548-59.
Summary of Product Characteristics. Kidrolase. https://pp.jazzpharma.com/pi/kidrolase.ca.PM-en.pdf. Accessed Mar. 5, 2021.
Tong, WH et al., A prospective study on drug monitoring of PEGasparaginase and Erwinia asparaginase and asparaginase antibodies in pediatric acute lymphoblastic leukemia, Blood. Mar. 27, 2014; 123(13): 2026-2033.
Ueno, T. et al., Cell cycle arrest and apoptosis of leukemia cells induced by L-asparaginase. Leukemia 1997;11:1858-61.
Uren, Jr. et al., Immunological and pharmacological characterization of poly-DL-alanyl-modified *Erwinia carotovora* L-asparaginase. Cancer Res 1982;42:4068-71.
Uren, Jr. et al., Improvement in the therapeutic, immunological, and clearance properties of *Escherichia coli* and *Erwinia carotovora* L-asparaginases by attachment of poly-DL-alanyl peptides. Cancer Res 1979;39:1927-33.
Van Der Sluis, IM et al., Consensus expert recommendations for identification and management of asparaginase hypersensitivity and silent inactivation. Haematologica 2016;100(3):279-85.
Vora, A et al., Augmented post-remission therapy for a minimal residual disease-defined high-risk subgroup of children and young people with clinical standard-risk and intermediate-risk acute lymphoblastic leukaemia (UKALL 2003): a randomised controlled trial. The lancet oncology. Jul. 1, 2014;15(8):809-18.
Vrooman, LM et al., Erwinia asparaginase after allergy to *E. coli* asparaginase in children with acute lymphoblastic leukemia. Pediatric Blood & Cancer. Feb. 2010; 54(2):199-205.
Vrooman, LM et al., Postinduction dexamethasone and individualized dosing of *Escherichia Coli* L-asparaginase each improve outcome of children and adolescents with newly diagnosed acute lymphoblastic leukemia: results from a randomized study—Dana-Farber Cancer Institute All Consortium Protocol 00-01. Journal of Clinical Oncology. Mar. 20, 2013;31(9):1202.
Wade, He et al., A new L-asparaginase with antitumour activity? Lancet 1968;2(7571):776-7. doi:10.1016/s0140-6736(68)90977-x.
Weaver, G., Steroid-induced pancreatitis. Gastroenterology. Mar. 1, 1982; 82(3):601.
Wolthers, Bo et al., Asparaginase-associated pancreatitis: a study on phenotype and genotype in the Nopho All 2008 protocol. Leukemia. 2017a Feb.; 31(2):325-32.
Wolthers, Bo et al., Asparaginase-associated pancreatitis in childhood acute lymphoblastic leukemia: an observational Ponte di Legno Toxicity Working Group study. The Lancet Oncology. 2017b Sep. 1; 18(9):1238-48.
Woo, MH et al., Hypersensitivity or development of antibodies to asparaginase does not impact treatment outcome of childhood acute lymphoblastic leukemia. Journal of Clinical Oncology. Apr. 7, 2000; 18(7):1525-32.
Young, DM et al., Clinicopathologic and ultrastructural studies of L asparaginase-induced hypocalcemia in rabbits. An experimental animal model of acute hypoparathyroidism. Lab Invest 1973;29(4):374-86.
Study No. SSARL-DPH-72-02; The toxicity of L-asparaginase from Erwinia carotovora (NSC 106977) in rabbits. Aug. 21, 1972.
Study No. SSARL-DPH-72-05; Effects of *E. Coli* L-Asparaginase (NSC 109229) and L-Asparaginase from Erwinia Carotovora (NSC 106977) on Rabbits, Rats, and Hamsters. Sep. 21, 1972.
Study No. SSARL-DPH-69-00; Toxicity studies on Erwinia carotovora L-asparaginase Batch Aug. 17, 1969 (NSC 109229) following daily IV administration to rhesus monkeys. Dec. 26, 1969 21 pages.
Study No. SSARL-DPH-71-01; Comparative Toxicity of IV Administration of Erwinia Carotovora L-Asparaginase and *E. Coli* L-Asparaginase to Rhesus Monkeys. Feb. 8, 1971 60 pages.
Study No. SSARL-DPH-71-02; Toxicity studies on NSC 106977, Erwinia L-asparaginase, MRE, Batch 9 following daily IV administration to a rhesus monkey. Mar. 16, 1971.
Study No. SSARL-DPH-70-07; Non Diabetogenic action of Erwinia L-Asparaginase when administered intravenously to a rhesus monkey and a rabbit. May 21, 1970.
CA Office Action in Canadian Application No. 3,156,066, dated Jul. 10, 2023, 5 pages.
EP Office Action in European Application No. 20803449.6, dated Oct. 13, 2023, 8 pages.
Ogawa et al., "Phase I/II Clinical Trial of Erwinia Asparaginase (Erwinase (R)) in Combination with Prednisolone, Vincristine and Pirarubicin in Children and Young Adults with Acute Lymphoblastic Leukemia (ALL) or Lymphoblastic Lymphoma (LBL)", Blood, Dec. 2014, 124(21): 3657, 8 pages.
Ogawa et al., "Plasma asparaginase Activity, asparagine concentration, and toxicity after administration of Erwinia asparaginase in children and young adults with acute lymphoblastic leukemia: Phase I/II clinical trial in Japan", Pediatric Blood and Cancer, Feb. 2017, 64(9): e26475.
SA Office Action in Saudi Arabian Application No. 522432357, dated May 8, 2024, 9 pages (with English translation).
FDA Highlights of Prescribing Information for Erwinaze published Mar. 2016.†
Minton N.P., Bullman, H.M.S., Scawen M.D., Atkinson T and Gilbert, H.J. Nucleotide sequence of the Erwinia chrysanthemi NCPPB 1066 L-asparaginase gene. Gene 46, 25-35 (1986).†
Jazz Pharmaceuticals Advances Recombinant Crisantaspase Development Program published Aug. 6, 2019.†
Summary of Product Characteristics, Labelling and Package Leaflet published Sep. 2016.†

\* cited by examiner
† cited by third party

Figure 1

Table 1. Treatment-emergent Adverse Events (TEAEs)

| Participants with TEAEs by preferred term, n (%) | RC-P, IV 25 mg/m² (N = 6) | RC-P, IV 37.5 mg/m² (N = 6) | RC-P, IM 12.5 mg/m² (N = 6) | RC-P, IM 25 mg/m² (N = 6) |
|---|---|---|---|---|
| Nausea | 3 (50) | 6 (100) | 2 (33) | 4 (67) |
| Vomiting | 2 (33) | 2 (33) | 1 (17) | 2 (33) |
| Dyspepsia | 1 (17) | 1 (17) | 5 (83) | 0 |
| Leukopenia | 1 (17) | 0 | 0 | 1 (17) |
| Soft feces | 1 (17) | 0 | 0 | 0 |
| Decreased appetite | 0 | 1 (17) | 0 | 0 |
| Diarrhea | 0 | 1 (17) | 0 | 0 |
| Gastroesophageal reflux | 0 | 0 | 0 | 1 (17) |
| Headache | 0 | 0 | 0 | 1 (17) |
| Malaise | 0 | 0 | 0 | 1 (17) |
| Neck pain | 0 | 1 (17) | 0 | 0 |
| Oral disorder | 0 | 0 | 0 | 1 (17) |
| Pain in extremity | 0 | 0 | 1 (17) | 0 |
| Paresthesia | 0 | 1 (17) | 0 | 0 |
| Upper respiratory infection | 0 | 1 (17) | 0 | 1 (17) |

Table 2. Proportion of Participants with Serum Asparaginase Activity Levels ≥0.1 IU/mL at 48 and 72 Hours After RC-P Administration

| Category | SAA Level | RC-P, IV 25 mg/m² (N = 6) | RC-P, IV 37.5 mg/m² (N = 6) | RC-P, IM 12.5 mg/m² (N = 6) | RC-P, IM 25 mg/m² (N = 6) |
|---|---|---|---|---|---|
| n (%) ≥0.1 IU/mL | SAA at 48 hours | 6 (100) | 6 (100) | 6 (100) | 6 (100) |
|  | SAA at 72 hours | 4 (67) | 6 (100) | 6 (100) | 6 (100) |

Figure 2

| Test Article | Condition | Total HMW% | Main Peak % |
|---|---|---|---|
| R-CRIS | Unstressed | 0.3 | 99.7 |
| | 5 Freeze/Thawed (F/T) | 0.4 | 99.6 |
| | 10 F/T | 0.5 | 99.5 |
| E.coli RC | Unstressed | 1.0 | 99.0 |
| | 5 F/T | 1.5 | 98.5 |
| | 10 F/T | 1.7 | 97.8 |
| Erwinase® | Unstressed | 5.8 | 94.2 |
| | 5 F/T | 5.8 | 94.2 |
| | 10 F/T | 5.9 | 94.1 |

Figure 3

| Test Article | Condition | Tetramer [%] | Octamer [%] | Higher Aggregates [%] |
|---|---|---|---|---|
| R-CRIS | Unstressed | 98.7 | 1.1 | 0.1 |
|  | 5 Freeze/Thawed (F/T) | 97.7 | 1.8 | 0.3 |
|  | 10 F/T | 97.2 | 2.3 | 0.3 |
| Erwinase® | Unstressed | 92.5 | 5.5 | 1.7 |
|  | 5 F/T | 92.0 | 5.9 | 1.9 |
|  | 10 F/T | 91.7 | 6.1 | 1.9 |
| E.coli RC | Unstressed | 97.2 | 2.1 | 0.2 |
|  | 5 F/T | 96.4 | 2.8 | 0.4 |
|  | 10 F/T | 96.5 | 2.8 | 0.4 |

Figure 4

| Test Article | Condition | Aggregates [%] | Main Peak [%] | Sedimentation coefficient [S] |
|---|---|---|---|---|
| R-CRIS | Unstressed | 1.0 | 99.0 | 7.38 |
| | 5 Freeze/Thawed (F/T) | 1.0 | 99.0 | 7.38 |
| | 10 F/T | 0.6 | 99.3 | 7.36 |
| E.coli RC | Unstressed | 3.6 | 96.0 | 7.32 |
| | 5 F/T | 2.6 | 97.4 | 7.35 |
| | 10 F/T | 2.6 | 96.9 | 7.35 |
| Erwinase® | Unstressed | 5.1 | 94.9 | 7.34 |
| | 5 F/T | 5.4 | 94.6 | 7.36 |
| | 10 F/T | 6.7 | 93.3 | 7.35 |

Figure 5

| Sample name | HMW (%) | Main Peak (%) | LMW (%) |
|---|---|---|---|
| R-CRIS | 0.2 | 99.6 | 0.2 |
| Erwinase® | 6.3 | 93.4 | 0.2 |

Figure 6

| Sample name | HMW | | Octamer | | Tetramer | | LMW | |
|---|---|---|---|---|---|---|---|---|
| | UV Rel. Peak Area [%] | Mw [kDa] | UV Rel. Peak Area [%] | Mw [kDa] | UV Rel. Peak Area [%] | Mw [kDa] | UV Rel. Peak Area [%] | Mw [kDa] |
| A | 0.04 | 435.10 | 0.26 | 246.30 | 99.28 | 134.80 | 0.42 | 114.50 |
| B | 0.04 | 407.00 | 0.26 | 240.30 | 99.27 | 134.80 | 0.42 | 118.00 |
| Average (n=2) | 0.04 | 421.05 | 0.26 | 243.30 | 99.28 | 134.80 | 0.42 | 116.25 |

Figure 9

Proportion of Healthy Volunteers With SAA Levels at 48 and 72 Hours Postdose

| Category | SAA Level | JZP-458 12.5 mg/m² IM (N = 6) | JZP-458 25 mg/m² IM (N = 6) | JZP-458 25 mg/m² IV (N = 6) | JZP-458 37.5 mg/m² IV (N = 6) | ERW 25,000 IU/m² IM (N = 3) | ERW 25,000 IU/m² IV (N = 3) |
|---|---|---|---|---|---|---|---|
| ≥0.1 IU/mL, n (%) | SAA at 48 hours | 6 (100) | 6 (100) | 6 (100) | 6 (100) | 3 (100) | 3 (100) |
|  | SAA at 72 hours | 6 (100) | 6 (100) | 4 (67) | 6 (100) | 3 (100) | 3 (100) |
| ≥0.4 IU/mL, n (%) | SAA at 48 hours | 4 (67) | 6 (100) | 5 (83) | 6 (100) | 3 (100) | 3 (100) |
|  | SAA at 72 hours | 0 | 5 (83) | 0 | 1 (17) | 1 (33) | 0 |

Figure 10

| Treatment, Mean (CV%) | $C_{max}$ (IU/mL) | $C_{48h}$ (IU/mL) | $C_{72h}$ (IU/mL) | $t_{max}$ (h) | $t_{1/2}$ (h) | $AUC_{0-t}$ (IU·h/mL) | $AUC_{0-inf}$ (IU·h/mL) | $CL^a$ (L/h) | $V^a$ (L) |
|---|---|---|---|---|---|---|---|---|---|
| JZP-458 12.5 mg/m² IM (N = 6) | 0.6 (13.2) | 0.4 (18.7) | 0.2 (32.9) | 24.0 (24.0-36.0) | 23.4 (23.6) | 33.3 (15.1) | 36.9 (18.4) | 0.4 (27.3) | 14.1 (25.1) |
| JZP-458 25 mg/m² IM (N = 6)[b] | 1.2 (18.8) | 0.9 (17.3) | 0.5 (33.6) | 36.0 (24.0-48.0) | 19.1 (21.8) | 66.3 (15.6) | 67.4 (9.0) | 0.4 (11.1) | 11.7 (20.9) |
| JZP-458 25 mg/m² IV (N = 6) | 10.9 (10.2) | 0.5 (37.7) | 0.1 (52.3) | 2.3 (2.0-3.5) | 11.5 (12.8) | 181 (20.5) | 182 (20.4) | 0.2 (25.7) | 2.7 (22.4) |
| JZP-458 37.5 mg/m² IV (N = 6) | 16.8 (18.1) | 1.2 (66.3) | 0.3 (63.8) | 2.3 (2.0-3.5) | 12.6 (11.2) | 315 (29.1) | 317 (29.5) | 0.1 (25.0) | 2.5 (16.6) |
| ERW 25,000 IU/m² IM (N = 3) | 1.3 (25.7) | 0.9 (11.6) | 0.4 (14.3) | 24.0 (24.0-36.0) | 20.6 (26.1) | 70.5 (15.3) | 75.8 (11.7) | 0.4 (20.8) | 13.0 (32.2) |
| ERW 25,000 IU/m² IV (N = 3) | 9.0 (21.0) | 0.8 (31.1) | 0.3 (37.6) | 2.0 (2.0-2.5) | 14.9 (12.0) | 180 (14.6) | 183 (15.1) | 0.2 (13.9) | 3.5 (8.1) |

Figure 11

TEAEs

| | JZP-458 12.5 mg/m² IM (N=6) | JZP-458 25 mg/m² IM (N=6) | JZP-458 25 mg/m² IV (N=6) | JZP-458 37.5 mg/m² IV (N=6) | ERW 25,000 IU/m² IM (N=3) | ERW 25,000 IU/m² IV (N=3) |
|---|---|---|---|---|---|---|
| TEAEs, n (%) | | | | | | |
| Any TEAE | 5 (83) | 4 (67) | 4 (67) | 6 (100) | 2 (67) | 3 (100) |
| Grade 1 | 5 (83) | 4 (67) | 4 (67) | 6 (100) | 2 (67) | 3 (100) |
| Grade 2 | 0 | 1 (17) | 1 (17) | 1 (17) | 0 | 1 (33) |
| Grade ≥3 | 0 | 0 | 0 | 0 | 0 | 0 |
| Serious TEAEs | 0 | 0 | 0 | 0 | 0 | 0 |
| Treatment-related TEAEs, n (%)ᵃ | | | | | | |
| Nausea | 2 (33) | 4 (67) | 3 (50) | 6 (100) | 2 (67) | 3 (100) |
| Vomiting | 1 (17) | 2 (33) | 2 (33) | 2 (33) | 0 | 2 (67) |
| Dyspepsia | 5 (83) | 0 | 0 | 0 | 1 (33) | 0 |
| Headache | 0 | 1 (17) | 0 | 0 | 0 | 1 (33) |
| Leukopenia | 0 | 1 (17) | 1 (17) | 0 | 0 | 0 |
| Decreased appetite | 0 | 0 | 0 | 1 (17) | 0 | 0 |
| Diarrhea | 0 | 0 | 0 | 1 (17) | 0 | 0 |
| Soft feces | 0 | 0 | 1 (17) | 0 | 0 | 0 |
| Gastroesophageal reflux disease | 0 | 1 (17) | 0 | 0 | 0 | 0 |
| Malaise | 0 | 1 (17) | 0 | 0 | 0 | 0 |
| Paresthesia | 0 | 0 | 0 | 1 (17) | 0 | 0 |

Figure 16

Baseline Demographics

| Characteristic | JZP-458 12.5 mg/m² IM (N = 6) | JZP-458 25 mg/m² IM (N = 6) | JZP-458 25 mg/m² IV (N = 6) | JZP-458 37.5 mg/m² IV (N = 6) | ERW 25,000 IU/m² IM (N = 3) | ERW 25,000 IU/m² IV (N = 3) |
|---|---|---|---|---|---|---|
| Age, mean ± SD, years | 43.0 ± 8.9 | 33.5 ± 7.7 | 33.8 ± 7.1 | 42.8 ± 6.8 | 36.0 ± 10.8 | 41.3 ± 3.8 |
| Male, n (%) | 6 (100) | 4 (67) | 4 (67) | 3 (50) | 1 (33) | 1 (33) |
| Weight, mean ± SD, kg | 80.8 ± 11.2 | 74.4 ± 5.5 | 80.0 ± 10.9 | 78.3 ± 11.0 | 74.9 ± 13.4 | 68.7 ± 8.6 |
| Body surface area, mean ± SD, m² | 2.0 ± 0.2 | 1.9 ± 0.1 | 2.0 ± 0.1 | 1.9 ± 0.1 | 1.9 ± 0.2 | 1.8 ± 0.1 |
| Ethnicity, n (%)[a] | | | | | | |
| Hispanic/Latino | 6 (100) | 5 (83) | 6 (100) | 6 (100) | 3 (100) | 3 (100) |
| Not Hispanic/Latino | 0 | 1 (17) | 0 | 0 | 0 | 0 |
| Race, n (%) | | | | | | |
| White | 5 (83) | 5 (83) | 5 (83) | 5 (83) | 2 (67) | 3 (100%) |
| Black/African American | 1 (17) | 1 (17) | 1 (17) | 1 (17) | 1 (33) | 0 |

Figure 17

Dose Proportionality Assessment for JZP-458 Based on SAA

| Route of Administration | SAA PK Parameter | n | Slope Estimate | 90% CI for Slope |
|---|---|---|---|---|
| IM | $C_{max}$ (IU/mL) | 12 | 1.02 | (0.77, 1.26) |
| | $AUC_{0-t}$ (IU·h/mL) | 12 | 1.00 | (0.76, 1.23) |
| | $AUC_{0-inf}$ (IU·h/mL) | 11 | 0.89 | (0.64, 1.13) |
| IV | $C_{max}$ (IU/mL) | 12 | 1.04 | (0.66, 1.43) |
| | $AUC_{0-t}$ (IU·h/mL) | 12 | 1.34 | (0.72, 1.95) |
| | $AUC_{0-inf}$ (IU·h/mL) | 12 | 1.33 | (0.72, 1.95) |

Figure 18

PK Summary Based on SAC

| Treatment, Mean (CV%) | $C_{max}$ (ng/mL) | $t_{max}$ (h) | $t_{1/2}$ (h) | $AUC_{0-t}$ (ng·h/mL) | $AUC_{0-inf}$ (ng·h/mL) | $CL^a$ (L/h) | $V^a$ (L) |
|---|---|---|---|---|---|---|---|
| JZP-458 12.5 mg/m² IM (N = 6)[b] | 858 (23.7) | 30.0 (24.0-36.0) | 28.9 (51.1) | 50,300 (18.2) | 58,800 (13.3) | 0.4 (22.4) | 11.3 (18.0) |
| JZP-458 25 mg/m² IM (N = 6) | 1,990 (13.7) | 30.0 (24.0-36.0) | 25.4 (20.0) | 106,000 (15.2) | 121,000 (19.3) | 0.4 (18.5) | 14.3 (13.4) |
| JZP-458 25 mg/m² IV (N = 6) | 14,400 (16.6) | 2.5 (2.0-4.0) | 12.0 (9.2) | 264,000 (18.8) | 266,000 (18.8) | 0.2 (28.1) | 3.2 (22.1) |
| JZP-458 37.5 mg/m² IV (N = 6) | 24,200 (7.9) | 2.5 (2.0-5.0) | 12.7 (12.8) | 443,000 (27.4) | 446,000 (28.1) | 0.2 (24.9) | 2.9 (13.3) |
| ERW 25,000 IU/m² IM (N = 3) | 1,790 (15.6) | 10.0 (10.0-36.0) | 25.3 (18.7) | 102,000 (12.1) | 113,000 (12.6) | 0.4 (25.5) | 15.1 (14.5) |
| ERW 25,000 IU/m² IV (N = 3) | 14,200 (17.1) | 3.0 (3.0-4.0) | 15.3 (13.2) | 267,000 (18.6) | 271,000 (18.5) | 0.2 (18.1) | 3.3 (16.5) |

Figure 19

Dose Proportionality Assessment for JZP-458 Based on SAC

| Route of Administration | Serum Asparaginase Concentrations PK Parameter | n | Slope Estimate | 90% CI for Slope |
|---|---|---|---|---|
| IM | $C_{max}$ (ng/mL) | 12 | 1.24 | (0.94, 1.54) |
| | $AUC_{0-t}$ (ng·h/mL) | 12 | 1.09 | (0.82, 1.35) |
| | $AUC_{0-inf}$ (ng·h/mL) | 9 | 1.03 | (0.69, 1.36) |
| IV | $C_{max}$ (ng/mL) | 12 | 1.31 | (0.96, 1.66) |
| | $AUC_{0-t}$ (ng·h/mL) | 12 | 1.25 | (0.65, 1.85) |
| | $AUC_{0-inf}$ (ng·h/mL) | 12 | 1.25 | (0.64, 1.86) |

Study design

Mean SAA-time Profiles for All Treatments and Corresponding Mean Plasma L-glutamine Levels

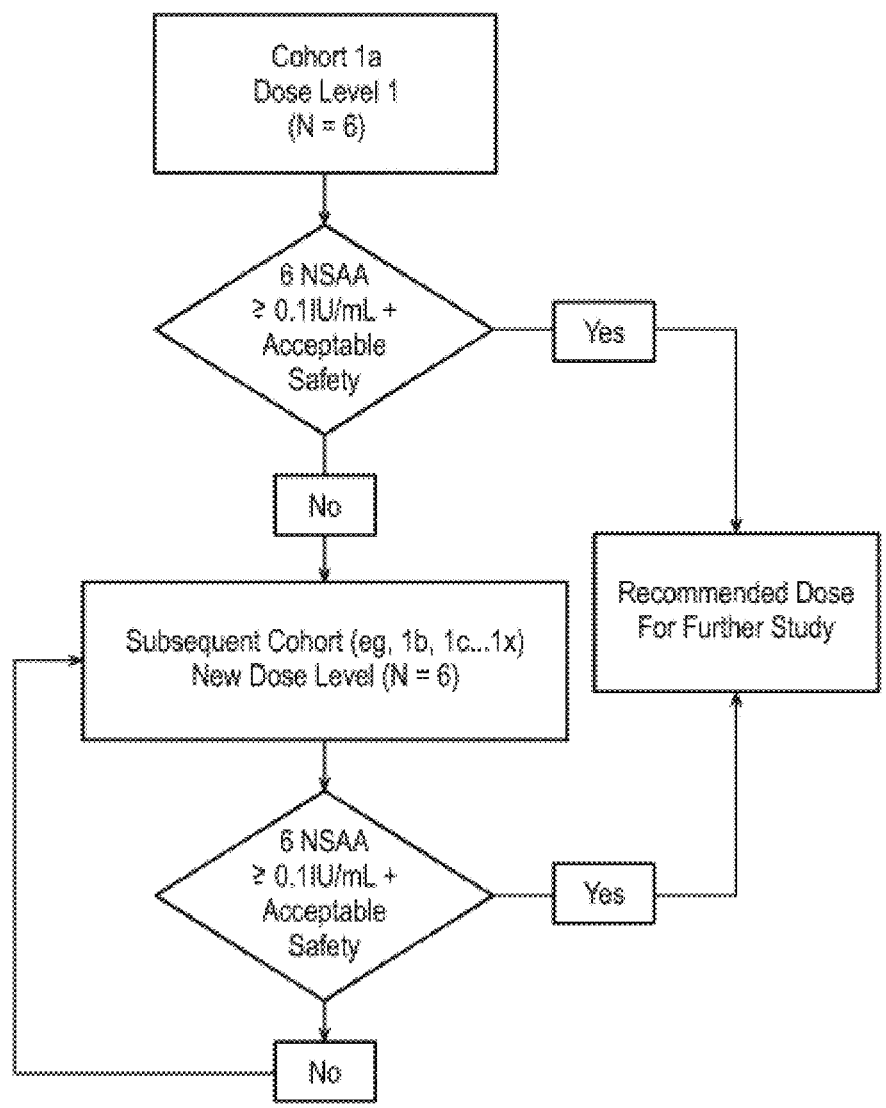

Figure 24

Table 2: Summary of SAA Results (IU/mL) with JZP-458 IM in Course 1 (Evaluable Participants) (Study JZP458-201)

| Route/ Dose Level | Time Point | Mean (95% CI) SAA (IU/mL) | Median (Q1, Q3) SAA (IU/mL) |
|---|---|---|---|
| IM/25 mg/m² (N = 26) | Last 48 hour | 0.4504 (0.3637-0.5370) | 0.4091 (0.2813, 0.6577) |
| | Last 72 hour | 0.1560 (0.1144-0.1976) | 0.1345 (0.0886, 0.2178) |
| IM/37.5 mg/m² (N = 16) | Last 48 hour | 0.7146 (0.3976-1.0316) | 0.6503 (0.3248, 0.8736) |
| | Last 72 hour | 0.2605 (0.1326-0.3884) | 0.1732 (0.1157, 0.2849) |

Abbreviations: IM = intramuscular; Q1 = first quartile; Q3 = third quartile; SAA = serum asparaginase activity
Source: Table 9 (Cohort 1a), Appendix 1; Table 9 (Cohort 1b), Appendix 2

Figure 25

Table 3: Proportion of Participants with NSAA Levels ≥ 0.1 and ≥ 0.4 IU/mL at the Last 48 and 72 Hours in Course 1 (Evaluable Participants) (Study JZP458-201)

| NSAA Level | Time Point | JZP-458, IM 25 mg/m² (N = 26) | JZP-458, IM 37.5 mg/m² (N = 16) |
|---|---|---|---|
| ≥ 0.1 IU/mL, n (%) | Last 48 hour | 25 (96.2) | 15 (93.8) |
| | Last 72 hour | 17 (65.4) | 13 (81.3) |
| ≥ 0.4 IU/mL, n (%) | Last 48 hour | 13 (50.0) | 9 (56.3) |
| | Last 72 hour | 1 (3.8) | 3 (18.8) |

Abbreviations: IM = intramuscular; NSAA = nadir serum asparaginase activity
Source: Tables 1.1 and 1.2 (Cohort 1a), Appendix 1; Tables 1.1 and 1.2 (Cohort 1b), Appendix 2

Figure 3: Simulated JZP-458 Median SAA Profiles with 95% Prediction Intervals – Semi-log scale (FMW Dosing Schedule) (Phase 2/3 JZP485-201 IM Simulation Model)

Figure 27

Table 4: Proportion of Patients Treated with JZP-458 Expected to Achieve Target SAA Trough Levels (FMW Dosing Schedule) (Phase 2/3 JZP458-201 IM Simulation Model)

| Route/Dose Level | Proportion of Patients ≥ 0.1 IU/mL (95% CI) | | | | | Mean SAA (IU/mL) (95% PI) | | | |
|---|---|---|---|---|---|---|---|---|---|
| | Dose 1 72-Hour Trough | Dose 4[a] 72-Hour Trough | Dose 5 48-Hour Trough | Dose 5 48-Hour Trough | | Dose 1 72-Hour Trough | Dose 4[a] 72-Hour Trough | Dose 5 48-Hour Trough | |
| IM/25 mg/m² | 62.4 (60.2, 64.5) | 68.7 (66.7, 70.7) | 99.1 (98.6, 99.5) | | | 0.15 (0.03, 0.38) | 0.19 (0.04, 0.56) | 0.37 (0.12, 0.87) | |
| IM/37.5 mg/m² | 84.1 (82.4, 85.7) | 87 (85.5, 88.5) | 99.9 (99.7, 100) | | | 0.23 (0.06, 0.6) | 0.29 (0.06, 0.88) | 0.58 (0.2, 1.32) | |
| IM/50 mg/m² | 92.4 (91.2, 93.6) | 94.2 (93.2, 95.2) | 100 (100, 100) | | | 0.31 (0.07, 0.77) | 0.39 (0.08, 1.15) | 0.77 (0.25, 1.75) | |
| IM/65 mg/m² | 96.4 (95.6, 97.2) | 97.4 (96.7, 98.1) | 100 (100, 100) | | | 0.39 (0.09, 0.98) | 0.49 (0.1, 1.41) | 0.98 (0.31, 2.16) | |
| IM/80 mg/m² | 98.9 (98.4, 99.3) | 99.3 (98.9, 99.6) | 100 (100, 100) | | | 0.48 (0.12, 1.22) | 0.61 (0.13, 1.83) | 1.21 (0.41, 2.78) | |

Abbreviations: CL = clearance; IM = intramuscular; SAA = serum asparaginase activity
Proportion represents the number calculated for 2000 simulated subjects per dose level.
FMW = A dosing schedule of Friday, Monday, and Wednesday. Patient population age range was 2 to 85 years.
The 95% Wald CI was calculated using SAS proc freq with the following option: / binomial (CL = WALD).
95% PI = prediction interval based on the percentiles (2.5 and 97.5 percentiles) for the simulated data
[a] Indicates the last 72 hours, which is the primary endpoint in the JZP458-201 protocol.
Source: PPK Modeling and Simulation Memorandum, Table 5

Figure 28

Table 5:   Overview of Treatment-emergent Adverse Events (Safety Analysis Set) (Study JZP458-201)

| Number (%) of Participants with the following: | JZP-458, IM 25 mg/m$^2$ (N = 31) | JZP-458, IM 37.5 mg/m$^2$ (N = 17) |
|---|---|---|
| Any TEAEs | 26 (83.9) | 13 (76.5) |
| Serious TEAEs | 9 (29.0) | 3 (17.6) |
| Treatment-related TEAEs | 13 (41.9) | 9 (52.9) |
| Serious treatment-related TEAEs | 1 (3.2) | 2 (11.8) |
| Grade 3 or 4 TEAEs | 18 (58.1) | 6 (35.3) |
| Treatment-related Grade 3 or 4 TEAEs | 6 (19.4) | 4 (23.5) |
| TEAEs leading to discontinuation of study drug | 1 (3.2) | 0 |

| Number (%) of Participants with the following: | JZP-458, IM 25 mg/m$^2$ (N = 31) | JZP-458, IM 37.5 mg/m$^2$ (N = 17) |
|---|---|---|
| Treatment-related TEAEs leading to discontinuation of study drug | 1 (3.2) | 0 |
| TEAEs leading to death | 0 | 0 |

Figure 29

Table 6: Grade 3 or 4 Treatment-emergent Adverse Events (Safety Analysis Set, Cohort 1a) (Study JZP458-201)

| Preferred Term, n (%) | JZP-458, IM 25 mg/m² (N = 31) |
|---|---|
| At least 1 Grade 3 or 4 TEAE | 18 (58.1) |
| Neutrophil count decreased | 9 (29.0) |
| White blood cell count decreased | 5 (16.1) |
| Febrile neutropenia | 6 (19.4) |
| Anemia | 5 (16.1) |
| Lymphocyte count decreased | 3 (9.7) |
| Platelet count decreased | 3 (9.7) |
| Alanine aminotransferase increased | 2 (6.5) |
| Neutropenia | 1 (3.2) |
| Lymphocyte count increased | 1 (3.2) |
| Decreased appetite | 1 (3.2) |
| Methaemoglobinaemia | 1 (3.2) |
| Stomatitis | 1 (3.2) |
| Fatigue | 1 (3.2) |
| Pyrexia | 1 (3.2) |
| Drug hypersensitivity | 1 (3.2) |
| Upper respiratory tract infection | 1 (3.2) |
| Lymphocyte count increased | 1 (3.2) |
| Dehydration | 1 (3.2) |
| Hypertriglyceridaemia | 1 (3.2) |
| Presyncope | 1 (3.2) |
| Uncoded event | 1 (3.2) |

Figure 30

Table 7: Grade 3 or 4 Treatment-emergent Adverse Events (Safety Analysis Set, Cohort 1b) (Study JZP458-201)

| Preferred Term, n (%) | JZP-458, IM 37.5 mg/m$^2$ (N = 17) |
|---|---|
| At least 1 Grade 3 or 4 TEAE | 6 (35.3) |
| Febrile neutropenia | 3 (17.6) |
| Neutrophil count decreased | 2 (11.8) |
| Platelet count decreased | 1 (5.9) |
| Anemia | 1 (5.9) |
| Sinus tachycardia | 1 (5.9) |
| Proctalgia | 1 (5.9) |
| Fatigue | 1 (5.9) |
| Allergic transfusion reaction | 1 (5.9) |

RECOMBINANT L-ASPARAGINASE

PRIORITY CLAIM

This application claims priority to U.S. Provisional Application Nos. 62/926,201 filed Oct. 25, 2019 and 63/047,222, filed Jul. 1, 2020, which are hereby incorporated by reference in their entirety.

TECHNICAL FIELD

The present invention provides a recombinant L-asparaginase, and its use in therapy.

BACKGROUND

Proteins with L-asparagine aminohydrolase activity, commonly known as L-asparaginases, have successfully been used for the treatment of various diseases that are potentially fatal, including Acute Lymphoblastic Leukemia (ALL) and Lymphoblastic Lymphoma (LBL), for which children constitute a large proportion of patients stricken with these diseases.

L-asparaginases of bacterial origin have a high immunogenic and antigenic potential. Currently on the market as first line treatment are *E. coli* derived L-asparaginase and pegaspargase. These products can provoke adverse hypersensitivity reactions including allergic reaction, silent inactivation, and anaphylactic shock in patients. Patients who experience hypersensitivity reactions to these products often have to stop treatment, resulting in poorer prognosis and survival rates. These patients have turned to Erwinaze® after experiencing hypersensitivity reactions. Erwinaze® has been plagued by supply issues for years, reportedly it can take 9 months to prepare. Even today the issues persist and Erwinase® shortages are common. The FDA has issued warning letters to the manufacturer stating that "changes in the source material or cell line have a substantial potential to adversely affect the identity, strength, quality, purity or potency of Erwinase®."

There is a need for immunogenically non-cross reactive treatment options. A recombinant L-asparaginase (like recombinant L-asparaginase recombinantly produced in *Pseudomonas fluorescens*) with no immunological cross-reactivity to *E. coli*-derived asparaginase would address a significant medical need (as a component of a multi-agent chemotherapeutic regimen) for patients with ALL/Lymphoblastic Lymphoma (LBL), by helping to ensure availability of an asparaginase for patients who have developed hypersensitivity to *E. coli*-derived asparaginase.

BRIEF SUMMARY OF THE INVENTION

Accordingly, the present disclosure provides a recombinant L-asparaginase with no immunological cross-reactivity to *E. coli*-derived asparaginase.

In one aspect, the present disclosure provides a method of treating a disease treatable by asparagine depletion in a human subject, the method comprising administering to the human subject a recombinant L-asparaginase in an amount from about 10 mg/m$^2$ to about 100 mg/m$^2$, wherein the recombinant L-asparaginase is a tetramer, wherein the tetramer has four monomers, wherein each monomer has an amino acid sequence comprising SEQ ID NO: 1.

In some embodiments, the recombinant L-asparaginase is not conjugated with a PEG moiety. In some embodiments, the recombinant L-asparaginase is not conjugated with a proline- or alanine-containing peptide.

In some embodiments, the human subject has been previously treated with an *E. coli*-derived asparaginase. In some further embodiments, the *E. coli*-derived asparaginase is conjugated to a PEG moiety.

In some embodiments, the human subject experienced silent inactivation of the *E. coli*-derived asparaginase.

In some embodiments, the human subject experienced an allergic reaction to the *E. coli*-derived asparaginase. In some embodiments, the human subject experienced anaphylaxis to the *E. coli*-derived asparaginase.

In some embodiments, the disease treatable by L-asparagine depletion is acute lymphoblastic leukemia (ALL). In some embodiments, the disease treatable by L-asparagine depletion is Lymphoblastic Lymphoma (LBL). In some embodiments, the ALL or LBL is relapsed ALL or relapsed LBL.

In some embodiments, the recombinant L-asparaginase is administered three times a week. In some embodiments, the recombinant L-asparaginase is administered every other day over a period of 5 consecutive days followed by a rest period of 2 consecutive days. In some embodiments, the recombinant L-asparaginase is administered on Monday, Wednesday, and Friday of the same week. In some embodiments, the recombinant L-asparaginase is administered for 2 weeks.

In some embodiments, the recombinant L-asparaginase is administered intramuscularly. In some embodiments, the recombinant L-asparaginase is administered intramuscularly in an amount of about 25 mg/m$^2$. In some embodiments, the recombinant L-asparaginase is administered intramuscularly in an amount between about 15 mg/m$^2$ and about 45 mg/m$^2$. In some embodiments, the recombinant L-asparaginase is administered intramuscularly in an amount between about 27 mg/m$^2$ and about 37.5 mg/m$^2$. In some embodiments, the recombinant L-asparaginase is administered intramuscularly in an amount between about 25 mg/m$^2$ and about 80 mg/m$^2$. In some embodiments, the recombinant L-asparaginase is administered intramuscularly in an amount between about 37.5 mg/m$^2$ and about 80 mg/m$^2$. In some embodiments, the recombinant L-asparaginase is administered intramuscularly in an amount between about 37.5 mg/m$^2$ and about 65 mg/m$^2$. In some embodiments, the recombinant L-asparaginase is administered intramuscularly in an amount between about 25 mg/m$^2$ and about 37.5 mg/m$^2$. In some embodiments, the recombinant L-asparaginase is administered intramuscularly in an amount between about 30 mg/m$^2$ and about 75 mg/m$^2$. In some embodiments, the recombinant L-asparaginase is administered intramuscularly in an amount between about 35 mg/m$^2$ and about 70 mg/m$^2$.

In some embodiments, the recombinant L-asparaginase is administered intramuscularly in an amount between about 40 mg/m$^2$ and about 65 mg/m$^2$. In some embodiments, the recombinant L-asparaginase is administered intramuscularly in an amount between about 45 mg/m$^2$ and about 60 mg/m$^2$. In some embodiments, the recombinant L-asparaginase is administered intramuscularly in an amount between about 50 mg/m$^2$ and about 55 mg/m$^2$. In some embodiments, the recombinant L-asparaginase is administered intramuscularly in an amount between about 40 mg/m$^2$ and about 75 mg/m$^2$. In some embodiments, the recombinant L-asparaginase is administered intramuscularly in an amount between about 45 mg/m$^2$ and about 70 mg/m$^2$. In some embodiments, the recombinant L-asparaginase is administered intramuscularly in an amount between about 50 mg/m$^2$ and about 65 mg/m$^2$. In some embodiments, the recombinant L-asparaginase is administered intramuscularly in an amount between about 55 mg/m² and about 60 mg/m². In some embodiments, the recombinant L-asparaginase is administered intramuscularly in an amount between about 40 mg/m² and about 60 mg/m². In some embodiments, the recombinant L-asparaginase is administered intramuscularly in an amount between about 45 mg/m² and about 55 mg/m². In some embodiments, the recombinant L-asparaginase is administered intramuscularly in an amount between about 47.5 mg/m² and about 50 mg/m². In some embodiments, the recombinant L-asparaginase is administered intramuscularly in an amount between about 30 mg/m² and about 35 mg/m².

In some embodiments, the recombinant L-asparaginase is administered intravenously. In some embodiments, the recombinant L-asparaginase is administered intravenously in an amount of about 37.5 mg/m². In some embodiments, the recombinant L-asparaginase is administered intravenously in an amount between about 25 mg/m² and about 55 mg/m². In some embodiments, the recombinant L-asparaginase is administered intravenously in an amount between about 27.5 mg/m² and about 47.5 mg/m². In some embodiments, the recombinant L-asparaginase is administered intravenously in an amount between about 21.5 mg/m² and about 38.5 mg/m². In some embodiments, the recombinant L-asparaginase is administered intravenously in an amount between about 25 mg/m² and about 37.5 mg/m². In some embodiments, the recombinant L-asparaginase is administered intravenously in an amount between about 25 mg/m² and about 100 mg/m². In some embodiments, the recombinant L-asparaginase is administered intravenously in an amount between about 25 mg/m² and about 65 mg/m². In some embodiments, the recombinant L-asparaginase is administered intravenously in an amount between about 25 mg/m² and about 80 mg/m². In some embodiments, the recombinant L-asparaginase is administered intravenously in an amount between about 30 mg/m² and about 35 mg/m². In some embodiments, the recombinant L-asparaginase is administered intravenously in an amount between about 30 mg/m² and about 95 mg/m². In some embodiments, the recombinant L-asparaginase is administered intravenously in an amount between about 35 mg/m² and about 90 mg/m². In some embodiments, the recombinant L-asparaginase is administered intravenously in an amount between about 40 mg/m² and about 85 mg/m². In some embodiments, the recombinant L-asparaginase is administered intravenously in an amount between about 45 mg/m² and about 80 mg/m². In some embodiments, the recombinant L-asparaginase is administered intravenously in an amount between about 50 mg/m² and about 75 mg/m². In some embodiments, the recombinant L-asparaginase is administered intravenously in an amount between about 55 mg/m² and about 70 mg/m². In some embodiments, the recombinant L-asparaginase is administered intravenously in an amount between about 60 mg/m² and about 65 mg/m². In some embodiments, the recombinant L-asparaginase is administered intravenously in an amount between about 30 mg/m² and about 60 mg/m². In some embodiments, the recombinant L-asparaginase is administered intravenously in an amount between about 35 mg/m² and about 55 mg/m². In some embodiments, the recombinant L-asparaginase is administered intravenously in an amount between about 40 mg/m² and about 50 mg/m². In some embodiments, the recombinant L-asparaginase is administered intravenously in an amount between about 42.5 mg/m² and about 57.5 mg/m². In some embodiments, the recombinant L-asparaginase is administered intravenously in an amount between about 30 mg/m² and about 75 mg/m². In some embodiments, the recombinant L-asparaginase is administered intravenously in an amount between about 40 mg/m² and about 65 mg/m². In some embodiments, the recombinant L-asparaginase is administered intravenously in an amount between about 45 mg/m² and about 60 mg/m². In some embodiments, the recombinant L-asparaginase is administered intravenously in an amount between about 50 mg/m² and about 55 mg/m².

In some embodiments, the nadir serum asparaginase activity (NSAA) as measured from a serum sample from the human subject equals or exceeds 0.1 IU/mL after administration after treatment with the recombinant L-asparaginase.

In some embodiments, the recombinant L-asparaginase is co-administered with one or more other chemotherapeutic agents as part of a multi-agent chemotherapeutic regimen.

In some embodiments, the recombinant L-asparaginase demonstrates less than 6% aggregation. In some embodiments, the recombinant L-asparaginase demonstrates less than 1% aggregation.

In some embodiments, the recombinant L-asparaginase is not lyophilized.

In another aspect, the present disclosure provides a method of treating a disease treatable by asparagine depletion in a human subject, the method comprising administering to the human subject a recombinant L-asparaginase, wherein the recombinant L-asparaginase is recombinantly produced in *Pseudomonas fluorescens*, wherein the recombinant L-asparaginase is a tetramer, wherein the tetramer has four monomers, wherein each monomer has an amino acid sequence comprising SEQ ID NO: 1.

In some embodiments, the recombinant L-asparaginase is not conjugated with a PEG moiety. In some embodiments, the recombinant L-asparaginase is not conjugated with a proline- or alanine-containing peptide.

In some embodiments, the human subject has been previously treated with an *E. coli*-derived asparaginase. In some embodiments, the *E. coli*-derived asparaginase is conjugated to a PEG moiety.

In some embodiments, the human subject experienced silent inactivation of the *E. coli*-derived asparaginase.

In some embodiments, the human subject experienced an allergic reaction to the *E. coli*-derived asparaginase.

In some embodiments, the human subject experienced anaphylaxis to the *E. coli*-derived asparaginase.

In some embodiments, the disease treatable by L-asparagine depletion is acute lymphoblastic leukemia (ALL). In some embodiments, the disease treatable by L-asparagine depletion is Lymphoblastic Lymphoma (LBL). In some embodiments, the ALL or LBL is relapsed ALL or relapsed LBL.

In some embodiments, the recombinant L-asparaginase is administered three times a week. In some embodiments, the recombinant L-asparaginase is administered every other day over a period of 5 consecutive days followed by a rest period of 2 consecutive days. In some embodiments, the recombinant L-asparaginase is administered on Monday, Wednesday, and Friday of the week.

In some embodiments, the recombinant L-asparaginase is administered for 2 weeks.

In some embodiments, recombinant L-asparaginase is administered in an amount from about 10 mg/m² to about 100 mg/m².

In some embodiments, the recombinant L-asparaginase is administered intramuscularly. In some embodiments, the recombinant L-asparaginase is administered intramuscularly in an amount of about 25 mg/m². In some embodiments, the recombinant L-asparaginase is administered intramuscularly in an amount between about 15 mg/m² and about 45 mg/m². In some embodiments, the recombinant L-asparaginase is administered intramuscularly in an amount between about 27 mg/m² and about 37.5 mg/m². In some embodiments, the recombinant L-asparaginase is administered intramuscularly in an amount between about 25 mg/m² and about 80 mg/m². In some embodiments, the recombinant L-asparaginase is administered intramuscularly in an amount between about 37.5 mg/m² and about 80 mg/m². In some embodiments, the recombinant L-asparaginase is administered intramuscularly in an amount between about 37.5 mg/m² and about 65 mg/m². In some embodiments, the recombinant L-asparaginase is administered intramuscularly in an amount between about 25 mg/m² and about 37.5 mg/m². In some embodiments, the recombinant L-asparaginase is administered intramuscularly in an amount between about 30 mg/m² and about 75 mg/m². In some embodiments, the recombinant L-asparaginase is administered intramuscularly in an amount between about 35 mg/m² and about 70 mg/m². In some embodiments, the recombinant L-asparaginase is administered intramuscularly in an amount between about 40 mg/m² and about 65 mg/m². In some embodiments, the recombinant L-asparaginase is administered intramuscularly in an amount between about 45 mg/m² and about 60 mg/m². In some embodiments, the recombinant L-asparaginase is administered intramuscularly in an amount between about 50 mg/m² and about 55 mg/m². In some embodiments, the recombinant L-asparaginase is administered intramuscularly in an amount between about 40 mg/m² and about 75 mg/m². In some embodiments, the recombinant L-asparaginase is administered intramuscularly in an amount between about 45 mg/m² and about 70 mg/m². In some embodiments, the recombinant L-asparaginase is administered intramuscularly in an amount between about 50 mg/m² and about 65 mg/m². In some embodiments, the recombinant L-asparaginase is administered intramuscularly in an amount between about 55 mg/m² and about 60 mg/m². In some embodiments, the recombinant L-asparaginase is administered intramuscularly in an amount between about 40 mg/m² and about 60 mg/m². In some embodiments, the recombinant L-asparaginase is administered intramuscularly in an amount between about 45 mg/m² and about 55 mg/m². In some embodiments, the recombinant L-asparaginase is administered intramuscularly in an amount between about 47.5 mg/m² and about 50 mg/m². In some embodiments, the recombinant L-asparaginase is administered intramuscularly in an amount between about 30 mg/m² and about 35 mg/m².

In some embodiments, the recombinant L-asparaginase is administered intravenously. In some embodiments, the recombinant L-asparaginase is administered intravenously in an amount of about 37.5 mg/m². In some embodiments, the recombinant L-asparaginase is administered intravenously in an amount between about 25 mg/m² and about 55 mg/m². In some embodiments, the recombinant L-asparaginase is administered intravenously in an amount between about 27.5 mg/m² and about 47.5 mg/m². In some embodiments, the recombinant L-asparaginase is administered intravenously in an amount between about 21.5 mg/m² and about 38.5 mg/m². In some embodiments, the recombinant L-asparaginase is administered intravenously in an amount between about 25 mg/m² and about 37.5 mg/m². In some embodiments, the recombinant L-asparaginase is administered intravenously in an amount between about 25 mg/m² and about 100 mg/m². In some embodiments, the recombinant L-asparaginase is administered intravenously in an amount between about 25 mg/m² and about 65 mg/m². In some embodiments, the recombinant L-asparaginase is administered intravenously in an amount between about 25 mg/m² and about 80 mg/m². In some embodiments, the recombinant L-asparaginase is administered intravenously in an amount between about 30 mg/m² and about 35 mg/m². In some embodiments, the recombinant L-asparaginase is administered intravenously in an amount between about 30 mg/m² and about 95 mg/m². In some embodiments, the recombinant L-asparaginase is administered intravenously in an amount between about 35 mg/m² and about 90 mg/m². In some embodiments, the recombinant L-asparaginase is administered intravenously in an amount between about 40 mg/m² and about 85 mg/m². In some embodiments, the recombinant L-asparaginase is administered intravenously in an amount between about 45 mg/m² and about 80 mg/m². In some embodiments, the recombinant L-asparaginase is administered intravenously in an amount between about 50 mg/m² and about 75 mg/m². In some embodiments, the recombinant L-asparaginase is administered intravenously in an amount between about 55 mg/m² and about 70 mg/m². In some embodiments, the recombinant L-asparaginase is administered intravenously in an amount between about 60 mg/m² and about 65 mg/m². In some embodiments, the recombinant L-asparaginase is administered intravenously in an amount between about 30 mg/m² and about 60 mg/m². In some embodiments, the recombinant L-asparaginase is administered intravenously in an amount between about 35 mg/m² and about 55 mg/m². In some embodiments, the recombinant L-asparaginase is administered intravenously in an amount between about 40 mg/m² and about 50 mg/m². In some embodiments, the recombinant L-asparaginase is administered intravenously in an amount between about 42.5 mg/m² and about 57.5 mg/m². In some embodiments, the recombinant L-asparaginase is administered intravenously in an amount between about 30 mg/m² and about 75 mg/m². In some embodiments, the recombinant L-asparaginase is administered intravenously in an amount between about 40 mg/m² and about 65 mg/m². In some embodiments, the recombinant L-asparaginase is administered intravenously in an amount between about 45 mg/m² and about 60 mg/m². In some embodiments, the recombinant L-asparaginase is administered intravenously in an amount between about 50 mg/m² and about 55 mg/m².

In some embodiments, the nadir serum asparaginase activity (NSAA) as measured from a serum sample from the human subject equals or exceeds 0.1 IU/mL after administration after treatment with the recombinant L-asparaginase.

In some embodiments, the recombinant L-asparaginase is co-administered with one or more other chemotherapeutic agents as part of a multi-agent chemotherapeutic regimen.

In some embodiments, a composition comprising recombinant L-asparaginase demonstrates less than 6% aggregation of the recombinant L-asparaginase protein. In some embodiments, the composition demonstrates less than 1% aggregation of the recombinant L-asparaginase protein.

In some embodiments, the recombinant L-asparaginase is not lyophilized or a composition containing the L-asparaginase is not a lyophilized composition.

In another aspect, the present disclosure provides a method of treating a disease treatable by asparagine depletion in a human subject, the method comprising administering to the human subject a composition comprising a recombinant L-asparaginase, wherein the recombinant L-asparaginase is a tetramer, wherein the tetramer has four monomers, wherein the composition demonstrates less than 6% aggregation of the recombinant L-asparaginase protein.

In some embodiments, the recombinant L-asparaginase is not conjugated with a PEG moiety. In some embodiments, the recombinant L-asparaginase is not conjugated with a proline- or alanine-containing peptide.

In some embodiments, the human subject has been previously treated with an *E. coli*-derived asparaginase. In some embodiments, the *E. coli*-derived asparaginase is conjugated to a PEG moiety.

In some embodiments, the human subject experienced silent inactivation of the *E. coli*-derived asparaginase. In some embodiments, the human subject experienced an allergic reaction to the *E. coli*-derived asparaginase.

In some embodiments, the human subject experienced anaphylaxis to the *E. coli*-derived asparaginase.

In some embodiments, the disease treatable by L-asparagine depletion is acute lymphoblastic leukemia (ALL). In some embodiments, the disease treatable by L-asparagine depletion is Lymphoblastic Lymphoma (LBL). In some embodiments, the ALL or LBL is relapsed ALL or relapsed LBL.

In some embodiments, the recombinant L-asparaginase is administered three times a week. In some embodiments, the recombinant L-asparaginase is administered every other day over a period of 5 consecutive days followed by a rest period of 2 consecutive days. In some embodiments, the recombinant L-asparaginase is administered on Monday, Wednesday, and Friday of the same week.

In some embodiments, the recombinant L-asparaginase is administered for 2 weeks.

In some embodiments, the recombinant L-asparaginase is administered in an amount from about 10 mg/m$^2$ to about 100 mg/m$^2$.

In some embodiments, the recombinant L-asparaginase is administered intramuscularly. In some embodiments, the recombinant L-asparaginase is administered intramuscularly in an amount of about 25 mg/m$^2$. In some embodiments, recombinant L-asparaginase is administered intramuscularly in an amount between about 15 mg/m$^2$ and about 45 mg/m$^2$. In some embodiments, the recombinant L-asparaginase is administered intramuscularly in an amount between about 27 mg/m$^2$ and about 37.5 mg/m$^2$. In some embodiments, the recombinant L-asparaginase is administered intramuscularly in an amount between about 25 mg/m$^2$ and about 80 mg/m$^2$. In some embodiments, the recombinant L-asparaginase is administered intramuscularly in an amount between about 37.5 mg/m$^2$ and about 80 mg/m$^2$. In some embodiments, the recombinant L-asparaginase is administered intramuscularly in an amount between about 37.5 mg/m$^2$ and about 65 mg/m$^2$. In some embodiments, the recombinant L-asparaginase is administered intramuscularly in an amount between about 25 mg/m$^2$ and about 37.5 mg/m$^2$. In some embodiments, the recombinant L-asparaginase is administered intramuscularly in an amount between about 30 mg/m$^2$ and about 75 mg/m$^2$. In some embodiments, the recombinant L-asparaginase is administered intramuscularly in an amount between about 35 mg/m$^2$ and about 70 mg/m$^2$. In some embodiments, the recombinant L-asparaginase is administered intramuscularly in an amount between about 40 mg/m$^2$ and about 65 mg/m$^2$. In some embodiments, the recombinant L-asparaginase is administered intramuscularly in an amount between about 45 mg/m$^2$ and about 60 mg/m$^2$. In some embodiments, the recombinant L-asparaginase is administered intramuscularly in an amount between about 50 mg/m$^2$ and about 55 mg/m$^2$. In some embodiments, the recombinant L-asparaginase is administered intramuscularly in an amount between about 40 mg/m$^2$ and about 75 mg/m$^2$. In some embodiments, the recombinant L-asparaginase is administered intramuscularly in an amount between about 45 mg/m$^2$ and about 70 mg/m$^2$. In some embodiments, the recombinant L-asparaginase is administered intramuscularly in an amount between about 50 mg/m$^2$ and about 65 mg/m$^2$. In some embodiments, the recombinant L-asparaginase is administered intramuscularly in an amount between about 55 mg/m$^2$ and about 60 mg/m$^2$. In some embodiments, the recombinant L-asparaginase is administered intramuscularly in an amount between about 40 mg/m$^2$ and about 60 mg/m$^2$. In some embodiments, the recombinant L-asparaginase is administered intramuscularly in an amount between about 45 mg/m$^2$ and about 55 mg/m$^2$. In some embodiments, the recombinant L-asparaginase is administered intramuscularly in an amount between about 47.5 mg/m$^2$ and about 50 mg/m$^2$. In some embodiments, the recombinant L-asparaginase is administered intramuscularly in an amount between about 30 mg/m$^2$ and about 35 mg/m$^2$.

In some embodiments, the recombinant L-asparaginase is administered intravenously. In some embodiments, the recombinant L-asparaginase is administered intravenously in an amount of about 37.5 mg/m$^2$. In some embodiments, the recombinant L-asparaginase is administered intravenously in an amount between about 25 mg/m$^2$ and about 55 mg/m$^2$. In some embodiments, the recombinant L-asparaginase is administered intravenously in an amount between about 27.5 mg/m$^2$ and about 47.5 mg/m$^2$. In some embodiments, the recombinant L-asparaginase is administered intravenously in an amount between about 21.5 mg/m$^2$ and about 38.5 mg/m$^2$. In some embodiments, the recombinant L-asparaginase is administered intravenously in an amount between about 25 mg/m$^2$ and about 37.5 mg/m$^2$. In some embodiments, the recombinant L-asparaginase is administered intravenously in an amount between about 25 mg/m$^2$ and about 100 mg/m$^2$. In some embodiments, the recombinant L-asparaginase is administered intravenously in an amount between about 25 mg/m$^2$ and about 65 mg/m$^2$. In some embodiments, the recombinant L-asparaginase is administered intravenously in an amount between about 25 mg/m$^2$ and about 80 mg/m$^2$. In some embodiments, the recombinant L-asparaginase is administered intravenously in an amount between about 30 mg/m$^2$ and about 35 mg/m$^2$. In some embodiments, the recombinant L-asparaginase is administered intravenously in an amount between about 30 mg/m$^2$ and about 95 mg/m$^2$. In some embodiments, the recombinant L-asparaginase is administered intravenously in an amount between about 35 mg/m$^2$ and about 90 mg/m$^2$. In some embodiments, the recombinant L-asparaginase is administered intravenously in an amount between about 40 mg/m$^2$ and about 85 mg/m$^2$. In some embodiments, the recombinant L-asparaginase is administered intravenously in an amount between about 45 mg/m$^2$ and about 80 mg/m$^2$. In some embodiments, the recombinant L-asparaginase is administered intravenously in an amount between about 50 mg/m$^2$ and about 75 mg/m$^2$. In some embodiments, the recombinant L-asparaginase is administered intravenously in an amount between about 55 mg/m$^2$ and about 70 mg/m$^2$. In some embodiments, the recombinant L-asparaginase is administered intravenously in an amount between about 60 mg/m$^2$ and about 65 mg/m$^2$. In some embodiments, the recombinant L-asparaginase is administered intravenously in an amount between about 30 mg/m$^2$ and about 60 mg/m$^2$. In some embodiments, the recombinant L-asparaginase is administered intravenously in an amount between about 35 mg/m$^2$ and about 55 mg/m$^2$. In some embodiments, the recombinant L-asparaginase is administered intravenously in an amount between about 40 mg/m$^2$ and about 50 mg/m$^2$. In some embodiments, the recombinant L-asparaginase is administered intravenously in an amount between about 42.5 mg/m$^2$ and about 57.5 mg/m$^2$. In some embodiments, the recombinant L-asparaginase is administered intravenously in an amount between about 30 mg/m$^2$ and about 75 mg/m². In some embodiments, the recombinant L-asparaginase is administered intravenously in an amount between about 40 mg/m² and about 65 mg/m². In some embodiments, the recombinant L-asparaginase is administered intravenously in an amount between about 45 mg/m² and about 60 mg/m². In some embodiments, the recombinant L-asparaginase is administered intravenously in an amount between about 50 mg/m² and about 55 mg/m².

In some embodiments, the nadir serum asparaginase activity (NSAA) as measured from a serum sample from the human subject equals or exceeds 0.1 IU/mL after administration after treatment with the recombinant L-asparaginase.

In some embodiments, the recombinant L-asparaginase is co-administered with one or more other chemotherapeutic agents as part of multi-agent chemotherapeutic regimen.

In some embodiments, each monomer of the tetramer has an amino acid sequence comprising SEQ ID NO: 1.

In some embodiments, the recombinant L-asparaginase is recombinantly produced in *Pseudomonas fluorescens*.

In some embodiments, the amount of aggregation of demonstrated by a composition comprising recombinant L-asparaginase is less than 1%.

In some embodiments, the recombinant L-asparaginase is not lyophilized.

In some embodiments, the multi-agent chemotherapeutic regimen is the recombinant L-asparaginase and one additional chemotherapeutic agent.

In some embodiments, the multi-agent chemotherapeutic regimen is the recombinant L-asparaginase and two or more additional chemotherapeutic agents.

In one aspect, the present invention provides a method of treating a disease in a human subject, the method comprising administering to the human subject recombinant L-asparaginase in an amount from about 10 mg/m² to about 100 mg/m², wherein the recombinant L-asparaginase is a tetramer, wherein the tetramer comprises four monomers, and wherein each monomer has an amino acid sequence comprising SEQ ID NO: 1.

In some embodiments, the disease is a member selected from sarcoma, breast cancer, metastatic breast cancer, liver cancer, stomach cancer, prostate cancer, colorectal cancer, and head and neck cancer.

In some embodiments, the recombinant L-asparaginase is not conjugated with a PEG moiety.

In some embodiments, the recombinant L-asparaginase is administered to the human subject as a substitute for a dose of a long-acting *E-coli*-derived asparaginase.

In some embodiments, six doses of recombinant L-asparaginase are administered to the human subject as a substitute for one dose of the long-acting *E. coli*-derived asparaginase.

In some embodiments, the long-acting *E. coli*-derived asparaginase is pegaspargase.

In some embodiments, a dose regimen for the recombinant L-asparaginase comprises a cycle, wherein the cycle comprises a first dose, a second dose, and a third dose, wherein the cycle is optionally repeatable, and wherein the first dose, second dose, and third dose are administered about 48-72 hours apart.

In some embodiments, a dose regimen for the recombinant L-asparaginase comprises a cycle, wherein the cycle is optionally repeatable, and wherein the cycle comprises administration of the recombinant L-asparaginase every other day over a period of five consecutive days followed by a rest period of two consecutive days, wherein the first dose of the cycle is 25 mg/m², the second dose of the cycle is 25 mg/m² and the third dose of the cycle is 37.5 mg/m², followed by the rest period of two consecutive days.

In some embodiments, a dose regimen for the recombinant L-asparaginase comprises a cycle, wherein the cycle is optionally repeatable, and wherein the cycle comprises administration of the recombinant L-asparaginase every other day over a period of five consecutive days followed by a rest period of two consecutive days, wherein the first dose of the cycle is 37.5 mg/m², the second dose of the cycle is 37.5 mg/m² and the third dose of the cycle is 37.5 mg/m², followed by the rest period of two consecutive days.

In some embodiments, a dose regimen for the recombinant L-asparaginase comprises a cycle, wherein the cycle is optionally repeatable, and wherein the cycle comprises administration of the recombinant L-asparaginase every other day over a period of five consecutive days followed by a rest period of two consecutive days, wherein the first dose of the cycle is 37.5 mg/m², the second dose of the cycle is 25 mg/m² and the third dose of the cycle is 37.5 in mg/m², followed by the rest period of two consecutive days.

In some embodiments, a dose regimen for the recombinant L-asparaginase comprises a cycle, wherein the cycle is optionally repeatable, and wherein the cycle comprises administration of the recombinant L-asparaginase every other day over a period of five consecutive days followed by a rest period of two consecutive days, wherein the first dose of the cycle is 37.5 mg/m², the second dose of the cycle is 25 mg/m² and the third dose of the cycle is 25 mg/m², followed by the rest period of two consecutive days.

In some embodiments, the first dose of the cycle is administered on a Monday, the second dose of the cycle is given on a Wednesday, and the third dose of the cycle is given on a Friday.

BRIEF DESCRIPTION OF THE DRAWINGS

The invention may be best understood from the following detailed description when read in conjunction with the accompanying drawings. Included in the drawings are the following figures:

FIG. 1 shows the results of the safety study in Example 2.

FIG. 2 shows the purities of recombinant L-asparaginase, *E. coli*-derived recombinant crisantaspase, and Erwinase® evaluated by the SEC-HPLC Method outlined in Example 5.

FIG. 3 shows the purities of recombinant L-asparaginase, *E. coli*-derived recombinant crisantaspase, and Erwinase® evaluated by the SEC-MALLS Method outlined in Example 5.

FIG. 4 shows the results obtained from the analysis of the sedimentation velocity AUC data outlined in Example 5.

FIG. 5 shows the size profile of recombinant L-asparaginase was assessed by SE-UHPLC according to the release method as outlined in Example 6.

FIG. 6 shows high molecular weight species present in the recombinant L-asparaginase were measured using SEC-MALLS as outlined in Example 6.

FIG. 9 shows the proportion of Healthy Volunteers with SAA Levels at 48 and 72 Hours Postdose according to Example 7. Abbreviations: ERW, asparaginase *Erwinia chrysanthemi*; IM, intramuscular; IV, intravenous; SAA, serum asparaginase activity.

FIG. 10 shows PK Summary Based on SAA in the study described in Example 7. Abbreviations: $AUC_{0-inf}$, area under the curve from time 0 extrapolated to infinity; $AUC_{0-t}$, area under the curve from time 0 to the time of last quantifiable SAA; $C_{48\ h}$, SAA at 48 hours; $C_{72\ h}$, SAA at 72 hours; CL, clearance; $C_{max}$, maximum SAA; CV, coefficient of variation; ERW, asparaginase *Erwinia chrysanthemi*; IM, intramuscular; IV, intravenous; PK, pharmacokinetics; SAA, serum asparaginase activity; $t_{max}$, time at which $C_{max}$ is observed; $t_{1/2}$, half-life; V, volume of distribution. [a]For IM treatments, CL=CL/F (apparent clearance) and V=Vz/F (apparent volume of distribution). For IV treatments, CL=CL and V=Vss (estimate of the volume of distribution at steady state). [b]n=5 for $t_{1/2}$, $AUC_{0-inf}$, CL, and V. N is the number of healthy volunteers exposed. Mean (CV %) presented for all parameters except for $t_{max}$ values, which are reported as median and range.

FIG. 11 shows TEAEs after treatment as described in Example 7. Abbreviations: ERW, asparaginase *Erwinia chrysanthemi*; IM, intramuscular; IV, intravenous; TEAE, treatment-emergent adverse event. [a]By preferred term using MedDRA dictionary, version 22.0; treatment-related TEAEs are shown in descending order of frequency.

FIG. 16 shows baseline demographics for the study in Example 7. Abbreviations: ERW, asparaginase *Erwinia chrysanthemi*; IM, intramuscular; IV, intravenous; SD, standard deviation. [a]Ethnicity was self-reported; healthy volunteers could identify as more than one ethnicity.

FIG. 17 shows the Dose Proportionality Assessment for JZP-458 Based on SAA as described further in the study in Example 7. Abbreviations: $AUC_{0-inf}$, area under the curve from time 0 extrapolated to infinity; $AUC_{0-t}$, area under the curve from time 0 to the time of the last quantifiable SAA; CI, confidence interval; $C_{max}$, maximum SAA; IM, intramuscular; IV, intravenous PK, pharmacokinetics; SAA, serum asparaginase activity. Results are based on the power model: ln (parameter)=intercept+slope×ln (dose).

FIG. 18 shows a PK Summary based on SAC as described further in Example 7. Abbreviations: $AUC_{0-inf}$, area under the curve from time 0 extrapolated to infinity; $AUC_{0-t}$, area under the curve from time 0 to the time of last quantifiable SAA; CL, clearance; $C_{max}$, maximum SAA; CV, coefficient of variation; ERW, asparaginase *Erwinia chrysanthemi*; IM, intramuscular; IV, intravenous; PK, pharmacokinetics; $t_{1/2}$, half-life; SAA, serum asparaginase activity; SAC, serum asparaginase concentration; $t_{max}$, time at which $C_{max}$ is observed; V, volume of distribution. [a]For IM treatments, CL=CL/F (apparent clearance) and V=Vz/F (apparent volume of distribution). For IV treatments, CL=CL and V=Vss (estimate of the volume of distribution at steady state). [b]n=3 for $AUC_{0-inf}$, CL, and V; n=5 for $t_{1/2}$. N is the number of healthy volunteers exposed. Mean (CV %) presented for all parameters except for $t_{max}$ values, which are reported as median and range.

FIG. 19 shows the Dose Proportionality Assessment for JZP-458 Based on SAC. Abbreviations: $AUC_{0-inf}$, area under the curve from time 0 extrapolated to infinity; $AUC_{0-t}$, area under the curve from time 0 to the time of the last quantifiable SAA; CI, confidence interval; $C_{max}$, maximum SAA; IM, intramuscular; IV, intravenous; PK, pharmacokinetics; SAA, serum asparaginase activity; SAC, serum asparaginase concentration. Results are based on the power model: ln (parameter)=intercept+slope×ln (dose).

FIG. 23 shows Part B JZP-458 Dose Cohorts (Example 8). The SDRC will assess the safety and tolerability issues for participants in Cohort 1 to determine if additional participants at a different dose level are needed. The SDRC will review NSAA and safety/tolerability data when 6 evaluable participants in each subcohort complete Course 1. Abbreviations: IU=International Units; IV=intravenous; NSAA=nadir serum asparaginase activity; SDRC=Study Data Review Committee FIG. 24 shows a summary of SAA results (IU/mL) with JZP-458 in Course 1 (Evaluable Participants) (Example 8).

FIG. 25 shows the proportion of patients with NSAA levels ≥0.1 and ≥0.4 IU/mL at the last 48 and 72 hours in Course 1 (evaluable participants) (Example 8).

FIG. 27 shows the proportion of patients treated with JZP-458 expected to achieve target SAA trough levels (FMW Dosing Schedule) (Example 8 IM Simulation Model).

FIG. 28 shows an overview of treatment-emergent adverse events (Safety Analysis Set) (Example 8).

FIG. 29 shows Grade 3 or 4 treatment-emergent adverse events (Safety Analysis Set Cohort 1a) (Example 8).

FIG. 30 shows Grade 3 or 4 treatment-emergent adverse events (Safety Analysis Set Cohort 1a) (Example 8). Percentages were calculated with the number of participants in the Safety Analysis Set as a denominator. Adverse events were coded to SOC and PT using MedDRA 22.1. The severity of AEs was recorded using CTCAE 5.0. A TEAE was defined as any event with onset date on or after the first dose of study treatment through the end of the study or any ongoing event that worsens in severity after the date of the first dose of study treatment through the end of the study. Abbreviations: AE=adverse event; CTCAE=Common Terminology Criteria for Adverse Events; IM=intramuscular injection; PT=preferred term; SOC=system organ class; TEAE=treatment-emergent adverse event

DETAILED DESCRIPTION OF THE INVENTION

Figure 7:
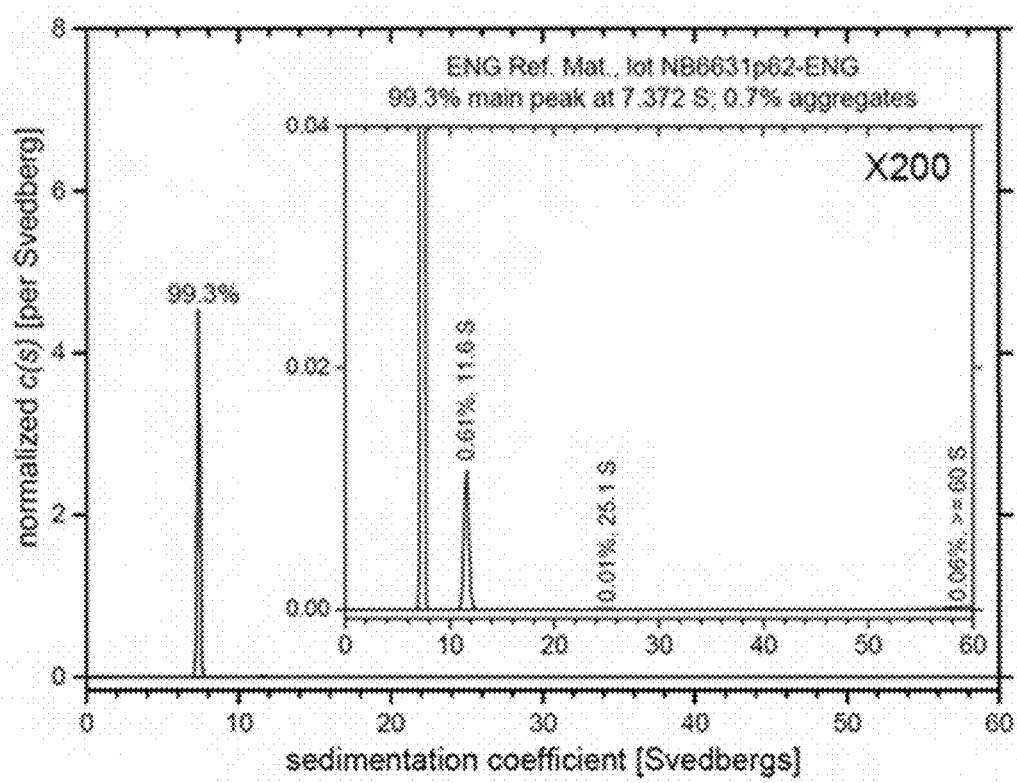
FIG. 7 shows the normalized sedimentation coefficient distribution of recombinant L-asparaginase (commercial scale) as outlined in Example 6.

L-asparaginases of bacterial origin have a high immunogenic and antigenic potential. These products can provoke adverse hypersensitivity reactions including allergic reaction, silent inactivation, and anaphylactic shock in patients. L-asparaginases are enzymes with L-asparagine aminohydrolase activity. L-asparaginase enzymatic activity may include not only deamidation of asparagine to aspartic acid and ammonia, but also deamidation of glutamine to glutamic acid and ammonia. L-asparaginases from *E. coli* and *Erwinia chrysanthemi* are commonly used to treat a variety of diseases treated by asparagine depletion, including ALL and LBL. While healthy cells can produce asparagine, some diseased cells are unable to produce asparagine as they lack asparagine synthetase. When an L-asparaginase is administered to a diseased patient, the L-asparaginase reduces the levels of soluble asparagine, starving the diseased cells but not the healthy cells and leading to selective diseased cell death. Antibodies developed after treatment with L-asparaginase from *E. coli* do not cross react with L-asparaginase from *Erwinia chrysanthemi*. L-asparaginases produced in *Erwinia chrysanthemi* require long lead times for manufacture (for example Erwinase®). The present invention comprises a recombinant L-asparaginase that does not cross-react with L-asparaginase from *E. coli* and provides the improvements over the *E. coli*-derived L-asparaginase and the *Erwinia chrysanthemi*-derived L-asparaginase. These improvements are described herein.

I. Definitions

Unless otherwise expressly defined, the terms used herein will be understood according to their ordinary meaning in the art.

As used herein, the term "disease treatable by depletion of asparagine" refers to a condition or disorder wherein the cells involved in or responsible for the condition or disorder either lack or have a reduced ability to synthesize L-asparagine. Depletion or deprivation of L-asparagine can be partial or substantially complete (e.g., to levels that are undetectable using methods and apparatus that are known in the art).

As used herein, the term "therapeutically effective amount" refers to the amount of a protein (e.g., asparaginase or recombinant L-asparaginase thereof), required to produce a desired therapeutic effect.

The term "comprising the sequence of SEQ ID NO: 1" means that the amino-acid sequence of the protein may not be strictly limited to SEQ ID NO: 1 but may contain additional amino-acids.

The term "subject" or "patient" intends an animal, a mammal, or yet further a human patient.

The term "host cell or a non-human host transformed with the vector" relates to a host cell or a non-human host that comprises the vector or the nucleic acid as described herein. Host cells for the expression of polypeptides are well known in the art and comprise prokaryotic cells as well as eukaryotic cells. Appropriate culture media and conditions for the above described host cells are known in the art.

"Culturing the host or host cell" includes expression of a protein, including as a fusion protein, as defined herein and/or the polypeptide as defined herein and/or of the asparaginase in the host or host cell.

As used herein, the term "about" modifying, for example, the dimensions, volumes, quantity of an ingredient in a composition, concentrations, process temperature, process time, yields, flow rates, pressures, and like values, and ranges thereof, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods; and like considerations. The term "about" also encompasses amounts that differ due to aging of, for example, a composition, formulation, or cell culture with a particular initial concentration or mixture, and amounts that differ due to mixing or processing a composition or formulation with a particular initial concentration or mixture. Whether modified by the term "about" the claims appended hereto include equivalents to these quantities. The term "about" further may refer to a range of values that are similar to the stated reference value. In certain embodiments, the term "about" refers to a range of values that fall within 10, 9, 8, 7, 6, 5, 4, 3, 2, 1 percent or less of the stated reference value.

The terms "co-administration," "co-administering," "administered in combination with," "administering in combination with," "simultaneous," and "concurrent," as used herein, encompass administration of two or more active pharmaceutical ingredients to a human subject so that both active pharmaceutical ingredients and/or their metabolites are present in the human subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present is also encompassed in the methods of the invention.

As used herein, the term "therapeutically effective amount" refers to the amount of a protein (e.g., recombinant L-asparaginase or conjugate thereof), required to produce a desired therapeutic effect.

The terms "*E. coli*-derived L-asparaginase," "L-asparaginase from *E. coli*," "*E. coli* asparaginase," and "*E. coli* L-asparaginase" are used interchangeably to refer to an asparaginase that is natively produced in *E. coli*.

The terms "*Erwinia*-derived L-asparaginase," "*Erwinia* asparaginase," "*Erwinia* L-asparaginase," "*Erwinia* asparaginase," "L-asparaginase from *Erwinia*," and "asparaginase from *Erwinia*," are used interchangeably herein to refer to an asparaginase that is natively produced in *Erwinia*.

The terms "L-asparaginase from *Erwinia chrysanthemi*," "*Erwinia chrysanthemi* L-asparaginase" and "*Erwinia chrysanthemi*-derived L-asparaginase" are used interchangeably to refer to an asparaginase that is natively produced in *Erwinia chrysanthemi*. *Erwinia chrysanthemi* (also known as *Pectobacterium chrysanthemi*) has been renamed *Dickeya chrysanthemi*. Thus, the terms *Erwinia chrysanthemi*, *Pectobacterium chrysanthemi* and *Dickeya chrysanthemi* are used interchangeably herein.

Erwinaze® (Biologic License Application 125359) is an *Erwinia chrysanthemi* L-asparaginase type II product commercially approved in the United States for treatment of ALL in patients. Its active ingredient is *Erwinia chrysanthemi* L-asparaginase type II (see Erwinaze® package insert, incorporated herein by reference).

II. Recombinant L-Asparaginase

In one aspect, a recombinant L-asparaginase in accordance with the disclosure provided herein is an L-asparaginase. In a further aspect, a recombinant L-asparaginase in accordance with the invention described herein is an enzyme with L-asparagine aminohydrolase activity. Such a recombinant L-asparaginase's enzymatic activity may include not only deamidation of asparagine to aspartic acid and ammonia, but also deamidation of glutamine to glutamic acid and ammonia.

In some embodiments, a recombinant L-asparaginase as disclosed herein is active as a multimer. In some embodiments, the recombinant L-asparaginase is an active enzyme as a tetramer. A tetramer is composed of four subunits (also known as monomers). In some embodiments, a recombinant L-asparaginase is a tetramer consisting of four identical 35 kD subunits. In some embodiments, the recombinant L-asparaginase is a non-disulfide bonded tetrameric therapeutic protein. In a particular embodiment, each of the subunits or monomers of a multimeric recombinant L-asparaginase comprises the amino acid sequence of SEQ ID NO: 1. In a particular embodiment, each of the subunits or monomers of a tetrameric recombinant L-asparaginase comprises the amino acid sequence of SEQ ID NO: 1. In another embodiment, the L-asparaginase is from *Erwinia chrysanthemi* NCPPB 1066 (Genbank Accession No. CAA32884, incorporated herein by reference in its entirety), either with or without signal peptides and/or leader sequences.

In some embodiments, the recombinant L-asparaginase is composed of multiple subunits, for example, four subunits or monomers (tetramer). A corresponding modified recombinant protein may then, e.g., consist of 1 to 20 (or more) peptides conjugated to each of the monomers of that tetramer. In some embodiments, the recombinant L-asparaginase comprises a monomer and 1, 2, 3, 4, 5, 6, 7, 8, 9, 10, 11, 12, 13, 14, 15, 16, 17, 18, 19, and 20 (or more) peptides conjugated to each of the L-asparaginase monomers. In a specific embodiment, the L-asparaginase is a multimer comprising multiple subunits or monomers, such as a tetramer, and each of the monomers in that tetramer is conjugated to 1 peptide, resulting in a tetramer comprising 4 conjugated peptides, one for each monomer. In some embodiments, the recombinant L-asparaginase is a tetramer comprising 1-4 peptides conjugated to each of the L-monomers. In some embodiments, the recombinant L-asparaginase is a tetramer comprising 4-20 peptides conjugated to each of the L-monomers. In some embodiments, the recombinant L-asparaginase is a tetramer comprising 6-18 peptides conjugated to each of the L-monomers. In some embodiments, the recombinant L-asparaginase is a tetramer comprising 6-18 peptides conjugated to each of the L-monomers. In some embodiments, the recombinant L-asparaginase is a tetramer comprising 10-15 peptides conjugated to each of the L-monomers.

In one aspect, the invention relates to a modified protein having a recombinant L-asparaginase and multiple chemically attached peptide sequences. In a further aspect the length of the peptide sequences are from about 10 to about 100, from about 15 to about 60 or from about 20 to about 40.

Fragments of recombinant L-asparaginase, preferably fragments of the recombinant L-asparaginase of SEQ ID NO: 1, may be of use in the presently described invention. The term "a fragment of recombinant L-asparaginase" (e.g. a fragment of the recombinant L-asparaginase of SEQ ID NO: 1) means that the sequence of the recombinant L-asparaginase may include fewer amino-acids than in the recombinant L-asparaginases exemplified herein (e.g. the recombinant L-asparaginase of SEQ ID NO: 1) but still enough amino-acids to confer L-aminohydrolase activity. For example, a "fragment of recombinant L-asparaginase" is a fragment that is/consists of at least about 150 or 200 contiguous amino acids of one of the recombinant L-asparaginases exemplified herein (e.g. the recombinant L-asparaginase of SEQ ID NO: 1) (for example about 150, 160, 170, 180, 190, 200, 210, 220, 230, 240, 250, 260, 270, 280, 290, 300, 310, 320, 321, 322, 323, 324, 325, 326 contiguous amino acids) and/or wherein said fragment has up to 50 amino acids deleted from the N-terminus of said recombinant L-asparaginases exemplified herein (e.g. the recombinant L-asparaginase of SEQ ID NO: 1) (e.g. up to 1, 2, 3, 4, 5, 6, 7, 8, 9, 10, 15, 20, 25, 30, 35, 40, 45, or 50) and/or has up to up to 75 or 100 amino acids deleted from the C-terminus of said recombinant L-asparaginases exemplified herein (e.g. the recombinant L-asparaginase of SEQ ID NO: 1) (e.g. up to 1, 2, 3, 4, 5, 6, 7, 8, 9, 10, 15, 20, 25, 30, 35, 40, 45, 50, 55, 60, 70, 75, 80, 85, 90, 95 or 100) and/or has deleted amino acids at both the N-terminus and the C-terminus of said recombinant L-asparaginases exemplified herein (e.g. the recombinant L-asparaginase of SEQ ID NO: 1), wherein the total number of amino acids deleted can be up to 125 or 150 amino acids.

Indeed, a person skilled in the art will understand how to select and design homologous proteins retaining substantially their L-asparaginase activity. Typically, a Nessler assay is used for the determination of L-asparaginase activity according to a method described by Mashburn and Wriston (Mashburn, L., and Wriston, J. (1963) "Tumor Inhibitory Effect of L-Asparaginase," Biochem Biophys Res Commun 12, 50, incorporated herein by reference in its entirety).

It is well known in the art that a polypeptide can be modified by substitution, insertion, deletion and/or addition of one or more amino-acids while retaining its enzymatic activity. The term "one or more amino acids" in this context can refer to one, two, three, four, five, six, seven, eight, nine, ten or more amino acids. For example, substitution of one amino-acid at a given position by a chemically equivalent amino-acid that does not affect the functional properties of a protein is common Substitutions may be defined as exchanges within one of the following groups:

Small aliphatic, non-polar or slightly polar residues: Ala, Ser, Thr, Pro, Gly

Polar, negatively charged residues and their amides: Asp, Asn, Glu, Gln

Polar, positively charged residues: His, Arg, Lys

Large aliphatic, non-polar residues: Met, Leu, Ile, Val, Cys

Large aromatic residues: Phe, Tyr, Trp.

Thus, changes that result in the substitution of one negatively charged residue for another (such as glutamic acid for aspartic acid) or one positively charged residue for another (such as lysine for arginine) can be expected to produce a functionally equivalent product.

The positions where the amino-acids are modified and the number of amino-acids that may be modified in the amino-acid sequence are not particularly limited. The skilled artisan is able to recognize the modifications that can be introduced without affecting the activity of the protein. For example, modifications in the N- or C-terminal portion of a protein may be expected not to alter the activity of a protein under certain circumstances. With respect to asparaginases, in particular, much characterization has been done, particularly with respect to the sequences, structures, and the residues forming the active catalytic site. This provides guidance with respect to residues that can be modified without affecting the activity of the enzyme. All known L-asparaginases from bacterial sources have common structural features. All are homotetramers with four active sites between the N- and C-terminal domains of two adjacent monomers (Aghaipour (2001) Biochemistry 40, 5655-5664, incorporated herein by reference in its entirety). All have a high degree of similarity in their tertiary and quaternary structures (Papageorgiou (2008) FEBS J. 275, 4306-4316, incorporated herein by reference in its entirety). The sequences of the catalytic sites of L-asparaginases are highly conserved between *Erwinia chrysanthemi*, *Erwinia carotovora*, and *E. coli* L-asparaginase II (Id). The active site flexible loop contains amino acid residues 14-33, and structural analysis show that Thr15, Thr95, Ser62, Glu63, Asp96, and Ala120 contact the ligand (Id). Aghaipour et al. have conducted a detailed analysis of the four active sites of *Erwinia chrysanthemi* L-asparaginase by examining high resolution crystal structures of the enzyme complexed with its substrates (Aghaipour (2001) Biochemistry 40, 5655-5664). Kotzia et al. provide sequences for L-asparaginases from several species and subspecies of *Erwinia* and, even though the proteins have only about 75-77% identity between *Erwinia chrysanthemi* and *Erwinia carotovora*, they each still have L-asparaginase activity (Kotzia (2007) J. Biotechnol. 127, 657-669). Moola et al performed epitope mapping studies of *Erwinia chrysanthemi* 3937 L-asparaginase and were able to retain enzyme activity even after mutating various antigenic sequences in an attempt to reduce immunogenicity of the asparaginase (Moola (1994) Biochem. J. 302, 921-927). In view of the extensive characterization that has been performed on L-asparaginases, one of skill in the art could determine how to make fragments and/or sequence substitutions while still retaining enzyme activity. More specifically, fragments of the protein of SEQ ID NO: 1 are also comprised within the definition of the protein used in the recombinant L-asparaginase of the invention. The term "a fragment of SEQ ID NO: 1" means that the sequence of the polypeptide may include fewer amino-acids than the full-length SEQ ID NO:1 but retains enough of the protein to confer L-aminohydrolase activity. In some embodiments, a recombinant L-asparaginase has at least about 80% homology or identity with the protein comprising SEQ ID NO: 1. In some embodiments, a recombinant L-asparaginase comprises a sequence identity of at least about 85%, 86%, 87%, 88%, 89%, 90%91%, 92%, 93%, 94%, 95%, 96%, 97%, 98%, 99% identity to the amino acid sequence of SEQ ID NO: 1. The terms "homology" and "sequence identity" are used interchangeably herein. The term "comprising the sequence of SEQ ID NO: 1" (for example if the L-asparaginase has 100% homology or sequence identity to the amino acid sequence of SEQ ID NO: 1) means that the amino acid sequence of the asparaginase may not be strictly limited to SEQ ID NO: 1 but may contain one, two, three, four, five, six, seven, eight, nine, ten or more additional amino acids.

SEQ ID NO: 1 is as follows:

```
ADKLPNIVILATGGTIAGSAATGTQTTGYKAGALG

VDTLINAVPEVKKLANVKGEQFSNMASENMTGDVVLKLSQ

RVNELLARDDVDGVVITHGTDTVEESAYFLHLTVKSDKPV

VFVAAMRPATAISADGPMNLLEAVRVAGDKQSRGRGVMVV

LNDRIGSARYITKTNASTLDTFKANEEGYLGVIIGNRIYY

QNRIDKLHTTRSVFDVRGLTSLPKVDILYGYQDDPEYLYD

AAIQHGVKGIVYAGMGAGSVSVRGIAGMRKAMEKGVVVIR

STRTGNGIVPPDEELPGLVSDSLNPAHARILLMLALTRTS

DPKVIQEYFHTY
```

The present disclosure also relates to a nucleic acid encoding the recombinant L-asparaginase described herein, particularly a nucleic acid encoding SEQ ID NO: 1 as defined herein.

A. PEGylation

In certain aspects, the recombinant L-asparaginase of the invention as described herein further comprises and/or is conjugated to a polymer. In some embodiments, the recombinant L-asparaginase as described herein is conjugated with a polyethylene glycol (PEG) moiety. In other embodiments, the recombinant L-asparaginase is not conjugated with a PEG moiety.

Polymers are selected from the group of non-toxic water soluble polymers such as polysaccharides, e.g. hydroxyethyl starch, poly amino acids, e.g. poly lysine, polyester, e.g., polylactic acid, and poly alkylene oxides, e.g., polyethylene glycol (PEG). Polyethylene glycol (PEG) or monomethoxy-polyethyleneglycol (mPEG) is well known in the art and comprises linear and branched polymers. Examples of some polymers, particularly PEG, are provided in the following, each of which is herein incorporated by reference in its entirety: U.S. Pat. Nos. 5,672,662; 4,179,337; 5,252,714; U.S. Patent Application Publication No. 2003/0114647;

U.S. Pat. Nos. 6,113,906; 7,419,600; 9,920,311 PCT Publication WO2019/109018, and PCT Publication No. WO2004/083258.

The quality of such polymers is characterized by the polydispersity index (PDI). The PDI reflects the distribution of molecular weights in a given polymer sample and is calculated from the weight average molecular weight divided by the number average molecular weight. It indicates the distribution of individual molecular weights in a batch of polymers. The PDI has a value always greater than 1, but as the polymer chains approach the ideal Gauss distribution (=monodispersity), the PDI approaches 1.

In one embodiment, the conjugate has the formula: Asp-[NH—CO—CH$_2$)x-CO—NH-PEG]n, wherein Asp is the recombinant L-asparaginase, NH is one or more of the NH groups of the lysine residues and/or the N-terminus of the Asp, PEG is a polyethylene glycol moiety, n is a number that represents at least about 40% to about 100% of the accessible amino groups (e.g., lysine residues and/or the N-terminus) in the Asp, and x is an integer ranging from about 1 to about 8, more specifically, from about 2 to about 5. In a specific embodiment, the PEG is monomethoxypolyethylene glycol (mPEG).

B. PASylation

In some embodiments, the recombinant L-asparaginase is conjugated with a proline- or alanine-containing peptide. In other embodiments, the recombinant crisantaspase is not conjugated with a proline-, alanine-, or serine-containing peptide.

In some embodiments, the recombinant L-asparaginase is a fusion protein comprising (i) a recombinant L-asparaginase having at least 85%, 90%, 91%, 92%, 93%, 94%, 95%, 96%, 97%, 98%, 99%, or 100% identity to the amino acid sequence of SEQ ID NO: 1 and (ii) one or more polypeptide(s), wherein the polypeptide consists solely of proline and alanine amino acid residues.

In such fusion proteins, the proline residues in the polypeptide consisting solely of proline and alanine amino acid residues may constitute more than about 10% and less than about 70% of the polypeptide. Accordingly, in such fusion proteins, it may be preferred that 10% to 70% of the total number of amino acid residues in the polypeptide are proline residues; more preferably, 20% to 50% of the total number of amino acid residues comprised in the polypeptide are proline residues; and even more preferably, 30% to 40% (e.g., 30%, 35% or 40%) of the total number of amino acid residues comprised in the polypeptide are proline residues. The polypeptide may comprise a plurality of amino acid repeats, wherein said repeat consists of proline and alanine residues and wherein no more than 6 consecutive amino acid residues are identical. Particularly, the polypeptide may comprise or consist of the amino acid sequence AAPAAPA-PAAPAAPAPAAPA or circular permuted versions or (a) multimers(s) of the sequences as a whole or parts of the sequence. In other embodiments, the recombinant L-asparaginase specifically lacks such a polypeptide, e.g., the recombinant L-asparaginase is not conjugated to a polypeptide containing the above-described percentages or repeats of proline residues.

The invention also relates to a nucleic acid encoding the recombinant L-asparaginase, particularly a fusion protein as defined herein. In some embodiments, the nucleotide sequence is a sequence encoding any of the recombinant L-asparaginases comprising SEQ ID NO: 1 and a polypeptide, wherein the polypeptide consists solely of proline and alanine amino acid residues, preferably wherein the protein is a fusion protein, described herein, except that one or more amino acid is added, deleted, inserted or substituted, with the proviso that the fusion protein having this amino acid sequence retains L-asparaginase activity. In other embodiments, the nucleotide sequence is a sequence encoding any recombinant L-asparaginase comprises SEQ ID NO: 1, wherein that sequence is not conjugated to (or part of a sequence encoding a fusion protein that contains) a polypeptide that consists solely of proline and alanine amino acid residues.

The recombinant L-asparaginase according to the present disclosure can be prepared using methods known in the art, particularly those methods disclosed in U.S. Pat. No. 10,174,302 and PCT Application No. WO2019/109018, herein incorporated by reference for exemplary embodiments.

C. Compositions Comprising Recombinant L-Asparaginase

The present disclosure also provides for compositions comprising a recombinant L-asparaginase. Such compositions may include a recombinant L-asparaginase in combination with other elements (including without limitation buffers, salts, and excipients). Such compositions may include vehicles for administering L-asparaginase into a subject, including for example particles, powders, and encapsulation.

In some embodiments, a recombinant L-asparaginase described herein can be encapsulated. The encapsulation of asparaginase in erythrocytes can in some instances serve to improve the therapeutic index (D. Schrijvers et al., Clin. Pharmacokinet. 2003, 42 (9): 779-791). Methods for encapsulation are described for example in EP1773452, which is incorporated by reference herein in its entirety and in particular for all teachings related to encapsulation of L-asparaginase.

III. Functional Aspects and Other Characteristics of a Recombinant L-Asparaginase and Compositions Thereof As will be appreciated, discussion herein of functional aspects and other characteristics of recombinant L-asparaginase can also apply to compositions comprising the recombinant L-asparaginase of the presently disclosed invention.

In some aspects, a recombinant L-asparaginase described herein may elicit a lower immunogenic response in the patient as compared to a wild-type L-asparaginase. In some embodiments, the recombinant L-asparaginase described herein can have a greater AUC value after a single dose compared to the native L-asparaginase. These characteristics of the recombinant L-asparaginase described herein are beneficial for a patient that may have had a previous hypersensitivity to an E. coli L-asparaginase or a PEGylated form thereof. In some embodiments, the recombinant L-asparaginase described herein does not raise any significant antibody response for a particular period of time after administration of a single dose, e.g., greater than about 1 week, 2 weeks, 3 weeks, 4, weeks, 5 weeks, 6 weeks, 7 weeks, 8 weeks, 9 weeks, 10 weeks, 11 weeks, 12 weeks, or longer. In one example, "does not raise any significant antibody response" means that the subject receiving the recombinant L-asparaginase is identified within art-recognized parameters as antibody-negative. Antibody levels can be determined by methods known in the art, for example ELISA or surface plasmon resonance assays (Zalewska-Szewczyk (2009) Clin. Exp. Med. 9, 113-116; Avramis (2009) Anticancer Research 29, 299-302, each of which is incorporated herein by reference in its entirety).

Compositions comprising the recombinant L-asparaginase of the present invention display reduced aggregation compared to those containing Erwinase® and *Erwinia chrysanthemi* L-asparaginase recombinantly expressed in *E. coli*. In some embodiments, compositions comprising the recombinant L-asparaginase described herein demonstrates reduced aggregation compared to compositions containing other forms L-asparaginase. For example, processes for manufacturing an unconjugated recombinant L-asparaginase of the present invention result in lower aggregation than Erwinase® and *Erwinia chrysanthemi* L-asparaginase recombinantly expressed in *E. coli*. The process for making batches of Erwinase® for example, results in a product with about 6% aggregation (see Example 5 and Example 6). Batches of a recombinant L-asparaginase of the present disclosure generally have less than about 1% aggregation (See Example 5 and Example 6).

In some embodiments, the recombinant L-asparaginase of the disclosure has greater purity than other L-asparaginases. In some embodiments, purity is measured by demonstrating the amount of aggregation in a given sample of an asparaginase. The amount of aggregation may be demonstrated by various methods described in the art, including but not limited to Size-Exclusion Chromatogaphy (SEC-HPLC), Size-Exclusion Ultrahigh-Performance Liquid Chromatography (SE-UHPLC), Size Exclusion Chromatography-Multi-Angle Light Scattering (SEC MALLS), and sedimentation velocity Analytical Ultracentrifugation (svAUC). In some embodiments, the amount of aggregation of the recombinant L-asparaginase is less than 10%, 9%, 8%, 7%, 6%, 5%, 4%, 3%, 2%, 1%, 0.5%, 0.25%, 0.2%, 0.1%, or 0.01%. In some embodiments, the amount of aggregation seen in compositions containing the recombinant L-asparaginase is less than 1-10%. In some embodiments, the amount of aggregation seen in compositions containing the recombinant L-asparaginase is less than 10%. In some embodiments, the amount of aggregation of the recombinant L-asparaginase is less than 9%. In some embodiments, the amount of aggregation of the recombinant L-asparaginase is less than 8%. In some embodiments, the amount of aggregation of the recombinant L-asparaginase is less than 7%. In some embodiments, the amount of aggregation of the recombinant L-asparaginase is less than 6%. In some embodiments, the amount of aggregation of the recombinant L-asparaginase is less than 5%. In some embodiments, the amount of aggregation of the recombinant L-asparaginase is less than 4%. In some embodiments, the amount of aggregation of the recombinant L-asparaginase is less than 3%. In some embodiments, the amount of aggregation of the recombinant L-asparaginase is less than 2%. In some embodiments, the amount of aggregation of the recombinant L-asparaginase is less than 1%. In some embodiments, the amount of aggregation of the recombinant L-asparaginase is less than 0.5%. In some embodiments, the amount of aggregation of the recombinant L-asparaginase is less than 0.25%. In some embodiments, the amount of aggregation of the recombinant L-asparaginase is less than 0.2%. In some embodiments, the amount of aggregation of the recombinant L-asparaginase is less than 0.1%. In some embodiments, the amount of aggregation of the recombinant L-asparaginase is less than 0.01%. In some embodiments, the amount of aggregation of the recombinant L-asparaginase is between 0.01% and 10%. In some embodiments, the amount of aggregation of the recombinant L-asparaginase is between about 0.01% and about 9%. In some embodiments, the amount of aggregation of the recombinant L-asparaginase is between about 0.01% and about 8%. In some embodiments, the amount of aggregation of the recombinant L-asparaginase is between about 0.01% and about 7%. In some embodiments, the amount of aggregation of the recombinant L-asparaginase is between about 0.01% and about 6%. In some embodiments, the amount of aggregation of the recombinant L-asparaginase is between about 0.1% and about 5%. In some embodiments, the amount of aggregation of the recombinant L-asparaginase is between about 0.2% and about 4%. In some embodiments, the amount of aggregation of the recombinant L-asparaginase is between about 0.25% and about 3%. In some embodiments, the amount of aggregation of the recombinant L-asparaginase is between about 0.5% and about 2%. In some embodiments, the amount of aggregation of the recombinant L-asparaginase is about 1%. In some embodiments, the amount of aggregation of the recombinant L-asparaginase is 1%.

It is known to those skilled in the art that lower amounts of aggregation typically results in a product with lower immunogenicity. Immunogenicity is a key factor in causing adverse events in the clinic and is regulated by the Federal Drug Administration (FDA) (See U.S. Department of Health and Human Services, Guidance for Industry: Immunogenicity Assessment for Therapeutic Protein Products, 2014, p. 15-17 of Quaternary Structure: Product Aggregates and Measurement of Aggregates; See also, Ratanji et al; Immunogenicity of therapeutic proteins: Influence of Aggregation. *Journal of Immunotoxicology*, 2014; 11(2): 99-109; Wang et al; Immunogenicity of Protein Aggregates-Concerns and Realities, *International Journal of Pharmaceutics*, 2012, 431(1-2): 1-11; and Moussa et al, Immunogenicity of Therapeutic Protein Aggregates, Journal of Pharmaceutical Sciences, 2016; 105(2): 417-430).

In addition, protein aggregation correlates with enzyme activity, as aggregation interferes with the ability of the enzyme to function and also may cause a reduction in the total yield of active enzyme. Protein aggregation causes challenges for manufacturing and development, delaying the time it takes to get therapeutics to patients and increasing cost. The recombinant crisantaspase of present disclosure demonstrates lower aggregation than other *Erwinia chrysanthemi* L-asparaginase recombinantly expressed in *E. coli* and *Erwinia chrysanthemi*-derived L-asparaginases. These aspects of the recombinant L-asparaginase make it an improvement over the art.

The recombinant L-asparaginase of the present disclosure may have any combination of the properties in the above sections or any other properties described herein.

IV. Methods of Manufacturing a Recombinant L-Asparaginase

In some embodiments, the recombinant crisantaspase disclosed herein is recombinantly produced in *Pseudomonas fluorescens*. In some embodiments, the *Pseudomonas fluorescens* is deficient in native L-asparaginase.

In some embodiments, the present disclosure provides methods for cytoplasmic production of a recombinant L-asparaginase in soluble form at high yields, wherein the recombinant protein is periplasmically produced at lower yields in its native host. In its native host, *Erwinia chrysanthemi*, L-asparaginase is produced in the periplasm. The present invention provides methods that allow production of high levels of soluble and/or active recombinant L-asparaginase in the cytoplasm of the host cell. In embodiments, methods provided herein yield high levels of soluble and/or active recombinant L-asparaginase in the cytoplasm of a Pseudomonadales, Pseudomonad, *Pseudomonas*, or *Pseudomonas fluorescens* host cell.

Methods that may be used for manufacturing a recombinant L-asparaginase are described for example in U.S. Pub. 2019/0127742, which is herein incorporated by reference in its entirety for all purposes and in particular for all teachings related to manufacturing methods for recombinant L-asparaginase.

A. Expression Systems

Methods herein, in some cases, comprise expressing a recombinant L-asparaginase from an expression construct in a *Pseudomonas* host cell. In some embodiments, the expression construct is a plasmid. In some embodiments, a plasmid encoding crisantaspase sequence comprises a selection marker, and host cells maintaining the plasmid are grown under selective conditions. In some embodiments, the plasmid does not comprise a selection marker. In some embodiments, the expression construct is integrated into the host cell genome. In some embodiments, the expression construct encodes crisantaspase fused to a secretion signal that directs crisantaspase to the periplasm. In some embodiments, the secretion signal is cleaved in the host cell. In some embodiments, the expression construct does not encode a secretion signal and the crisantaspase is directed to the cytoplasm.

Methods for expressing heterologous proteins, including regulatory sequences (e.g., promoters, secretion leaders, and ribosome binding sites) useful in the methods of the invention in host strains, including *Pseudomonas* host strains, are described, e.g., in U.S. Pat. No. 7,618,799, "Bacterial leader sequences for increased expression," in U.S. Pat. No. 7,985, 564, "Expression systems with Sec-system secretion," in U.S. Pat. Nos. 9,394,571 and 9,580,719, both titled "Method for Rapidly Screening Microbial Hosts to Identify Certain Strains with Improved Yield and/or Quality in the Expression of Heterologous Proteins," U.S. Pat. No. 9,453,251, "Expression of Mammalian Proteins in *Pseudomonas fluorescens*," U.S. Pat. No. 8,603,824, "Process for Improved Protein Expression by Strain Engineering," and U.S. Pat. No. 8,530,171, "High Level Expression of Recombinant Toxin Proteins," each incorporated herein by reference in its entirety. In embodiments, a secretion leader used in the context of the present invention is a secretion leader as disclosed in any of U.S. Pat. Nos. 7,618,799, 7,985,564, 9,394,571, 9,580,719, 9,453,251, 8,603,824, and 8,530,171. These patents also describe bacterial host strains useful in practicing the methods herein, that have been engineered to overexpress folding modulators or wherein protease mutations have been introduced, in order to increase heterologous protein expression.

B. Promoters

The promoters used in accordance with the methods herein may be constitutive promoters or regulated promoters. Common examples of useful regulated promoters include those of the family derived from the lac promoter (i.e. the lacZ promoter), especially the tac and trc promoters described in U.S. Pat. No. 4,551,433 to DeBoer, as well as Ptac16, Ptac17, PtacII, PlacUV5, and the T7lac promoter. In one embodiment, the promoter is not derived from the host cell organism. In certain embodiments, the promoter is derived from an *E. coli* organism.

Inducible promoter sequences are used to regulate expression of a recombinant L-asparaginase in accordance with the methods herein. In embodiments, inducible promoters useful in the methods herein include those of the family derived from the lac promoter (i.e. the lacZ promoter), especially the tac and trc promoters described in U.S. Pat. No. 4,551,433 to DeBoer, as well as Ptac16, Ptac17, PtacII, PlacUV5, and the T7lac promoter. In one embodiment, the promoter is not derived from the host cell organism. In certain embodiments, the promoter is derived from an *E. coli* organism. In some embodiments, a lac promoter is used to regulate expression of crisantaspase from a plasmid. In the case of the lac promoter derivatives or family members, e.g., the tac promoter, an inducer is IPTG (isopropyl-β-D-1-thiogalactopyranoside, also called "isopropylthiogalactoside"). In certain embodiments, IPTG is added to culture to induce expression of crisantaspase from a lac promoter in a *Pseudomonas* host cell.

Common examples of non-lac-type promoters useful in expression systems according to the methods herein include those specified in U.S. Pat. App. Pub. No. 2019/0127742, incorporated by reference herein, specifically for the examples listed in Table 1.

Also see, e.g.: J. Sanchez-Romero & V. De Lorenzo, 1999, Manual of Industrial Microbiology and Biotechnology (A. Demain & J. Davies, eds.) pp. 460-74 (ASM Press, Washington, D.C.); H. Schweizer, 2001, Current Opinion in Biotechnology, 12:439-445; R. Slater & R. Williams, 2000, Molecular Biology and Biotechnology (J. Walker & R. Rapley, eds.) pp. 125-54 (The Royal Society of Chemistry, Cambridge, UK), and L.-M. Guzman, et al., 1995, J. Bacteriol. 177(14): 4121-4130, all incorporated by reference herein. A promoter having the nucleotide sequence of a promoter native to the selected bacterial host cell also may be used to control expression of the transgene encoding the target polypeptide, e.g., a *Pseudomonas* anthranilate or benzoate operon promoter (Pant, Pben). Tandem promoters may also be used in which more than one promoter is covalently attached to another, whether the same or different in sequence, e.g., a Pant-Pben tandem promoter (interpromoter hybrid) or a Plac-Plac tandem promoter, or whether derived from the same or different organisms.

Regulated promoters utilize promoter regulatory proteins in order to control transcription of the gene of which the promoter is a part. Where a regulated promoter is used herein, a corresponding promoter regulatory protein will also be part of an expression system according to methods herein. Examples of promoter regulatory proteins include: activator proteins, for example, *E. coli* catabolite activator protein, MalT protein; AraC family transcriptional activators; repressor proteins, for example, *E. coli* LacI proteins; and dual-function regulatory proteins, for example, *E. coli* NagC protein. Many regulated-promoter/promoter-regulatory-protein pairs are known in the art. In one embodiment, the expression construct for the target protein(s) and the heterologous protein of interest are under the control of the same regulatory element.

Promoter regulatory proteins interact with an effector compound, i.e., a compound that reversibly or irreversibly associates with the regulatory protein so as to enable the protein to either release or bind to at least one DNA transcription regulatory region of the gene that is under the control of the promoter, thereby permitting or blocking the action of a transcriptase enzyme in initiating transcription of the gene. Effector compounds are classified as either inducers or co-repressors, and these compounds include native effector compounds and gratuitous inducer compounds. Many regulated-promoter/promoter-regulatory-protein/effector-compound trios are known in the art. Although, in some cases, an effector compound is used throughout the cell culture or fermentation, in one embodiment in which a regulated promoter is used, after growth of a desired quantity or density of host cell biomass, an appropriate effector compound is added to the culture to directly or indirectly result in expression of the desired gene(s) encoding the protein or polypeptide of interest.

In embodiments wherein a lac family promoter is utilized, a lad gene is sometimes present in the system. The lad gene, which is normally a constitutively expressed gene, encodes the Lac repressor protein Lad protein, which binds to the lac operator of lac family promoters. Thus, where a lac family promoter is utilized, the lad gene is sometimes also included and expressed in the expression system. Promoter systems useful in *Pseudomonas* are described in the literature, e.g., in U.S. Pat. App. Pub. No. 2008/0269070, also referenced above.

C. Other Regulatory Elements

In embodiments, a soluble recombinant L-asparaginase of the present disclosure is present in either the cytoplasm or periplasm of the cell during production. Secretion leaders useful for targeting proteins, e.g., crisantaspase, are described elsewhere herein, and in U.S. Pat. App. Pub. No. 2008/0193974, U.S. Pat. App. Pub. No. 2006/0008877, and in U.S. patent application Ser. No. 12/610,207, referenced above. In some embodiments, expression constructs are provided that encode a recombinant L-asparaginase fused to a secretion leader that transports the recombinant L-asparaginase to the periplasm of a Pseudomonad or *Pseudomonas* cell. In some embodiments, the secretion leader the secretion leader is cleaved from the recombinant L-asparaginase. In some embodiments, the secretion leader facilitates production of soluble crisantaspase.

In embodiments, the expression vector contains an optimal ribosome binding sequence. Modulating translation strength by altering the translation initiation region of a protein of interest can be used to improve the production of heterologous cytoplasmic proteins that accumulate mainly as inclusion bodies due to a translation rate that is too rapid. Secretion of heterologous proteins into the periplasmic space of bacterial cells can also be enhanced by optimizing rather than maximizing protein translation levels such that the translation rate is in sync with the protein secretion rate. The translation initiation region has been defined as the sequence extending immediately upstream of the ribosomal binding site (RBS) to approximately 20 nucleotides downstream of the initiation codon (McCarthy et al. (1990) Trends in Genetics 6:78-85, herein incorporated by reference in its entirety). In prokaryotes, alternative RBS sequences can be utilized to optimize translation levels of heterologous proteins by providing translation rates that are decreased with respect to the translation levels using the canonical, or consensus, RBS sequence (AGGAGG) described by Shine and Dalgarno (Proc. Natl. Acad. Sci. USA 71:1342-1346, 1974). By "translation rate" or "translation efficiency" is intended the rate of mRNA translation into proteins within cells. In most prokaryotes, the Shine-Dalgarno sequence assists with the binding and positioning of the 30S ribosome component relative to the start codon on the mRNA through interaction with a pyrimidine-rich region of the 16S ribosomal RNA. The RBS (also referred to herein as the Shine-Dalgarno sequence) is located on the mRNA downstream from the start of transcription and upstream from the start of translation, typically from 4 to 14 nucleotides upstream of the start codon, and more typically from 8 to 10 nucleotides upstream of the start codon. Because of the role of the RBS sequence in translation, there is a direct relationship between the efficiency of translation and the efficiency (or strength) of the RBS sequence.

In some embodiments, modification of the RBS sequence results in a decrease in the translation rate of the heterologous protein. This decrease in translation rate may correspond to an increase in the level of properly processed protein or polypeptide per gram of protein produced, or per gram of host protein. The decreased translation rate can also correlate with an increased level of recoverable protein or polypeptide produced per gram of recombinant or per gram of host cell protein. The decreased translation rate can also correspond to any combination of an increased expression, increased activity, increased solubility, or increased translocation (e.g., to a periplasmic compartment or secreted into the extracellular space). In this embodiment, the term "increased" is relative to the level of protein or polypeptide that is produced, properly processed, soluble, and/or recoverable when the protein or polypeptide of interest is expressed under the same conditions, or substantially the same conditions, and wherein the nucleotide sequence encoding the polypeptide comprises the canonical RBS sequence. Similarly, the term "decreased" is relative to the translation rate of the protein or polypeptide of interest wherein the gene encoding the protein or polypeptide comprises the canonical RBS sequence. The translation rate can be decreased by at least about 5%, at least about 10%, at least about 15%, at least about 20%, about 25%, about 30%, about 35%, about 40%, about 45%, about 50%, about 55%, about 60%, about 65%, about 70, at least about 75% or more, or at least about 2-fold, about 3-fold, about 4-fold, about 5-fold, about 6-fold, about 7-fold, or greater.

In some embodiments, the RBS sequence variants described herein can be classified as resulting in high, medium, or low translation efficiency. In one embodiment, the sequences are ranked according to the level of translational activity compared to translational activity of the canonical RBS sequence. A high RBS sequence has about 60% to about 100% of the activity of the canonical sequence. A medium RBS sequence has about 40% to about 60% of the activity of the canonical sequence. A low RBS sequence has less than about 40% of the activity of the canonical sequence.

Examples of RBS sequences according to the methods herein include those specified in U.S. Pat. App. Pub. No. 2019/0127742, which is incorporated by reference herein, specifically for the examples listed in Table 2.

An expression construct useful in practicing the methods herein include, in addition to the protein coding sequence, the following regulatory elements operably linked thereto: a promoter, a ribosome binding site (RBS), a transcription terminator, and translational start and stop signals. Useful RBSs are obtained from any of the species useful as host cells in expression systems according to, e.g., U.S. Pat. App. Pub. No. 2008/0269070 and U.S. patent application Ser. No. 12/610,207. Many specific and a variety of consensus RBSs are known, e.g., those described in and referenced by D. Frishman et al., Gene 234(2): 257-65 (8 Jul. 1999); and B. E. Suzek et al., Bioinformatics 17(12):1123-30 (December 2001). In addition, either native or synthetic RBSs may be used, e.g., those described in: EP 0207459 (synthetic RBSs); O. Ikehata et al., Eur. J. Biochem. 181(3):563-70 (1989). Further examples of methods, vectors, and translation and transcription elements, and other elements useful in the methods herein are described in, e.g.: U.S. Pat. No. 5,055, 294 to Gilroy and U.S. Pat. No. 5,128,130 to Gilroy et al.; U.S. Pat. No. 5,281,532 to Rammler et al.; U.S. Pat. Nos. 4,695,455 and 4,861,595 to Barnes et al.; U.S. Pat. No. 4,755,465 to Gray et al.; and U.S. Pat. No. 5,169,760 to Wilcox.

D. Host Strains

Bacterial hosts, including Pseudomonads, and closely related bacterial organisms are contemplated for use in practicing the methods herein. In certain embodiments, the Pseudomonad host cell is *Pseudomonas fluorescens*. In some embodiments, the host cell is a *Pseudomonas fluorescens* cell in which the cell is deficient in native L-asparaginase.

Host cells and constructs useful in practicing the methods herein are identified or made using reagents and methods known in the art and described in the literature, e.g., in U.S. Pat. App. Pub. No. 2009/0325230, "Protein Expression Systems," incorporated herein by reference in its entirety. This publication describes production of a recombinant polypeptide by introduction of a nucleic acid construct into an auxotrophic *Pseudomonas fluorescens* host cell comprising a chromosomal lacI gene insert. The nucleic acid construct comprises a nucleotide sequence encoding the recombinant polypeptide operably linked to a promoter capable of directing expression of the nucleic acid in the host cell, and also comprises a nucleotide sequence encoding an auxotrophic selection marker. The auxotrophic selection marker is a polypeptide that restores prototrophy to the auxotrophic host cell. In embodiments, the cell is auxotrophic for proline, uracil, or combinations thereof. In embodiments, the host cell is derived from MB101 (ATCC deposit PTA-7841). U. S. Pat. App. Pub. No. 2009/0325230, "Protein Expression Systems," and in Schneider, et al., 2005, "Auxotrophic markers pyrF and proC, in some cases, replace antibiotic markers on protein production plasmids in high-cell-density *Pseudomonas fluorescens* fermentation," Biotechnol. Progress 21(2): 343-8, both incorporated herein by reference in their entirety, describe a production host strain auxotrophic for uracil that was constructed by deleting the pyrF gene in strain MB101. The pyrF gene was cloned from strain MB214 (ATCC deposit PTA-7840) to generate a plasmid that complements the pyrF deletion to restore prototrophy. In particular embodiments, a dual pyrF-proC dual auxotrophic selection marker system in a *P. fluorescens* host cell is used. A pyrF deleted production host strain as described is often used as the background for introducing other desired genomic changes, including those described herein as useful in practicing the methods herein.

In embodiments, a host cell useful in the methods of the present invention is deficient in the expression of at least one protease, overexpresses at least one folding modulator, or both. In embodiments, the host cell is not deficient in the expression of a protease and does not overexpress a folding modulator, and therefore is wild-type with respect to protease and folding modulator expression. In any of these embodiments, the host cell is additionally deficient in a native L-asparaginase. In embodiments, the deficiency in the native L-asparaginase is generated by deleting or otherwise inactivating the native L-asparaginase gene using any suitable method known in the art. In embodiments, the host cell is deficient in a native Type I L-asparaginase, a native Type II L-asparaginase, or both. In embodiments, the host cell is wild-type with respect to protease and folding modulator expression, and deficient in a native Type I L-asparaginase and a native Type II L-asparaginase. For example, a host cell useful in the methods of the invention can be generated by one of skill in the art from MB101, using known methods. In embodiments, the host cell is generated by deleting or otherwise inactivating the native Type I L-asparaginase gene, the native Type II L-asparaginase gene, or both, in MB101.

It would be understood by one of skill in the art that a production host strain useful in the methods of the present invention can be generated using a publicly available host cell, for example, *P. fluorescens* MB101, e.g., by inactivating the pyrF gene, and/or the native Type IL-asparaginase gene, and/or the native Type II L-asparaginase gene, using any of many appropriate methods known in the art and described in the literature. It is also understood that a prototrophy restoring plasmid can be transformed into the strain, e.g., a plasmid carrying the pyrF gene from strain MB214 using any of many appropriate methods known in the art and described in the literature. Additionally, in such strains proteases can be inactivated, and folding modulator overexpression constructs introduced, using methods well known in the art.

In embodiments, the host cell is of the order Pseudomonadales. Where the host cell is of the order Pseudomonadales, it may be a member of the family Pseudomonadaceae, including the genus *Pseudomonas*. Gamma Proteobacterial hosts include members of the species *Escherichia coli* and members of the species *Pseudomonas fluorescens*. Host cells of the order Pseudomonadales, of the family Pseudomonadaceae, or of the genus *Pseudomonas* are identifiable by one of skill in the art and are described in the literature (e.g., Bergey's Manual of Systematics of Archaea and Bacteria (online publication, 2015)).

Other *Pseudomonas* organisms may also be useful. Pseudomonads and closely related species include Gram-negative Proteobacteria Subgroup 1, which include the group of Proteobacteria belonging to the families and/or genera described in Bergey's Manual of Systematics of Archaea and Bacteria (online publication, 2015). Table 3 presents these families and genera of organisms.

Examples of Families and Genera Listed in the Part, "Gram-Negative Aerobic Rods and Cocci" (in Bergey's Manual of Systematics of Archaea and Bacteria (online publication, 2015)) include those specified in U.S. Pat. App. Pub. No. 2019/0127742, which is incorporated by reference herein, specifically for the examples listed in Table 3.

*Pseudomonas* and closely related bacteria are generally part of the group defined as "Gram(–) Proteobacteria Subgroup 1" or "Gram-Negative Aerobic Rods and Cocci" (Bergey's Manual of Systematics of Archaea and Bacteria (online publication, 2015)). *Pseudomonas* host strains are described in the literature, e.g., in U.S. Pat. App. Pub. No. 2006/0040352, cited above.

"Gram-negative Proteobacteria Subgroup 1" also includes Proteobacteria that would be classified in this heading according to the criteria used in the classification. The heading also includes groups that were previously classified in this section but are no longer, such as the genera *Acidovorax, Brevundimonas, Burkholderia, Hydrogenophaga, Oceanimonas, Ralstonia*, and *Stenotrophomonas*, the genus *Sphingomonas* (and the genus *Blastomonas*, derived therefrom), which was created by regrouping organisms belonging to (and previously called species of) the genus *Xanthomonas*, the genus *Acidomonas*, which was created by regrouping organisms belonging to the genus *Acetobacter* as defined in Bergey's Manual of Systematics of Archaea and Bacteria (online publication, 2015). In addition hosts include cells from the genus *Pseudomonas, Pseudomonas enalia* (ATCC 14393), *Pseudomonas nigrifaciensi* (ATCC 19375), and *Pseudomonas putrefaciens* (ATCC 8071), which have been reclassified respectively as *Alteromonas haloplanktis, Alteromonas nigrifaciens*, and *Alteromonas putrefaciens*. Similarly, e.g., *Pseudomonas acidovorans* (ATCC 15668) and *Pseudomonas testosteroni* (ATCC 11996) have since been reclassified as *Comamonas acidovorans* and *Comamonas testosteroni*, respectively; and *Pseudomonas nigrifaciens* (ATCC 19375) and *Pseudomonas piscicida* (ATCC 15057) have been reclassified respectively as *Pseudoaltero-* monas nigrifaciens and Pseudoalteromonas piscicida. "Gram-negative Proteobacteria Subgroup 1" also includes Proteobacteria classified as belonging to any of the families: Pseudomonadaceae, Azotobacteraceae (now often called by the synonym, the "*Azotobacter* group" of Pseudomonadaceae), Rhizobiaceae, and Methylomonadaceae (now often called by the synonym, "Methylococcaceae"). Consequently, in addition to those genera otherwise described herein, further Proteobacterial genera falling within "Gram-negative Proteobacteria Subgroup 1" include: 1) *Azotobacter* group bacteria of the genus *Azorhizophilus*; 2) Pseudomonadaceae family bacteria of the genera *Cellvibrio*, *Oligella*, and *Teredinibacter*; 3) Rhizobiaceae family bacteria of the genera *Chelatobacter, Ensifer, Liberibacter* (also called "*Candidatus liberibacter*"), and *Sinorhizobium*; and 4) Methylococcaceae family bacteria of the genera *Methylobacter, Methylocaldum, Methylomicrobium, Methylosarcina,* and *Methylosphaera*.

The host cell, in some cases, is selected from "Gram-negative Proteobacteria Subgroup 16." "Gram-negative Proteobacteria Subgroup 16" is defined as the group of Proteobacteria of the following *Pseudomonas* species (with the ATCC or other deposit numbers of exemplary strain(s) shown in parenthesis): *Pseudomonas abietaniphila* (ATCC 700689); *Pseudomonas aeruginosa* (ATCC 10145); *Pseudomonas alcaligenes* (ATCC 14909); *Pseudomonas anguilliseptica* (ATCC 33660); *Pseudomonas citronellolis* (ATCC 13674); *Pseudomonas flavescens* (ATCC 51555); *Pseudomonas mendocina* (ATCC 25411); *Pseudomonas nitroreducens* (ATCC 33634); *Pseudomonas oleovorans* (ATCC 8062); *Pseudomonas pseudoalkaligenes* (ATCC 17440); *Pseudomonas resinovorans* (ATCC 14235); *Pseudomonas straminea* (ATCC 33636); *Pseudomonas agarici* (ATCC 25941); *Pseudomonas alcaliphila; Pseudomonas alginovora; Pseudomonas andersonii; Pseudomonas asplenii* (ATCC 23835); *Pseudomonas azelaica* (ATCC 27162); *Pseudomonas beyerinckii* (ATCC 19372); *Pseudomonas borealis; Pseudomonas boreopolis* (ATCC 33662); *Pseudomonas brassicacearum; Pseudomonas butanovora* (ATCC 43655); *Pseudomonas cellulosa* (ATCC 55703); *Pseudomonas aurantiaca* (ATCC 33663); *Pseudomonas chlororaphis* (ATCC 9446, ATCC 13985, ATCC 17418, ATCC 17461); *Pseudomonas fragi* (ATCC 4973); *Pseudomonas lundensis* (ATCC 49968); *Pseudomonas taetrolens* (ATCC 4683); *Pseudomonas cissicola* (ATCC 33616); *Pseudomonas coronafaciens; Pseudomonas diterpeniphila; Pseudomonas elongata* (ATCC 10144); *Pseudomonas flectens* (ATCC 12775); *Pseudomonas azotoformans; Pseudomonas brenneri; Pseudomonas cedrella; Pseudomonas corrugata* (ATCC 29736); *Pseudomonas extremorientalis; Pseudomonas fluorescens* (ATCC 35858); *Pseudomonas gessardii; Pseudomonas libanensis; Pseudomonas mandelii* (ATCC 700871); *Pseudomonas marginalis* (ATCC 10844); *Pseudomonas migulae; Pseudomonas mucidolens* (ATCC 4685); *Pseudomonas orientalis; Pseudomonas rhodesiae; Pseudomonas synxantha* (ATCC 9890); *Pseudomonas tolaasii* (ATCC 33618); *Pseudomonas veronii* (ATCC 700474); *Pseudomonas frederiksbergensis; Pseudomonas geniculata* (ATCC 19374); *Pseudomonas gingeri; Pseudomonas graminis; Pseudomonas grimontii; Pseudomonas halodenitrificans; Pseudomonas halophila; Pseudomonas hibiscicola* (ATCC 19867); *Pseudomonas huttiensis* (ATCC 14670); *Pseudomonas hydrogenovora; Pseudomonas jessenii* (ATCC 700870); *Pseudomonas kilonensis; Pseudomonas lanceolata* (ATCC 14669); *Pseudomonas lini; Pseudomonas marginata* (ATCC 25417); *Pseudomonas mephitica* (ATCC 33665); *Pseudomonas denitrificans* (ATCC 19244); *Pseudomonas pertucinogena* (ATCC 190); *Pseudomonas pictorum* (ATCC 23328); *Pseudomonas psychrophila, Pseudomonas filva* (ATCC 31418); *Pseudomonas monteilii* (ATCC 700476); *Pseudomonas mosselii; Pseudomonas oryzihabitans* (ATCC 43272); *Pseudomonas plecoglossicida* (ATCC 700383); *Pseudomonas putida* (ATCC 12633); *Pseudomonas reactans; Pseudomonas spinosa* (ATCC 14606); *Pseudomonas balearica; Pseudomonas luteola* (ATCC 43273). *Pseudomonas stutzeri* (ATCC 17588); *Pseudomonas amygdali* (ATCC 33614); *Pseudomonas avellanae* (ATCC 700331); *Pseudomonas caricapapayae* (ATCC 33615); *Pseudomonas cichorii* (ATCC 10857); *Pseudomonas ficuserectae* (ATCC 35104); *Pseudomonas fuscovaginae; Pseudomonas meliae* (ATCC 33050); *Pseudomonas syringae* (ATCC 19310); *Pseudomonas viridiflava* (ATCC 13223); *Pseudomonas thermocarboxydovorans* (ATCC 35961); *Pseudomonas thermotolerans; Pseudomonas thivervalensis; Pseudomonas vancouverensis* (ATCC 700688); *Pseudomonas wisconsinensis*; and *Pseudomonas xiamenensis*. In one embodiment, the host cell for expression of recombinant L-asparaginase is *Pseudomonas fluorescens*.

The host cell, in some cases, is selected from "Gram-negative Proteobacteria Subgroup 17." "Gram-negative Proteobacteria Subgroup 17" is defined as the group of Proteobacteria known in the art as the "fluorescent Pseudomonads" including those belonging, e.g., to the following *Pseudomonas* species: *Pseudomonas azotoformans; Pseudomonas brenneri; Pseudomonas cedrella; Pseudomonas cedrina; Pseudomonas corrugata; Pseudomonas extremorientalis; Pseudomonas fluorescens; Pseudomonas gessardii; Pseudomonas libanensis; Pseudomonas mandelii; Pseudomonas marginalis; Pseudomonas migulae; Pseudomonas mucidolens; Pseudomonas orientalis; Pseudomonas rhodesiae; Pseudomonas synxantha; Pseudomonas tolaasii;* and *Pseudomonas veronii*.

E. Proteases

In one embodiment, the methods provided herein comprise using a *Pseudomonas* host cell, comprising one or more mutations (e.g., a partial or complete deletion) in one or more protease genes, to produce recombinant L-asparaginase. In some embodiments, a mutation in a protease gene facilitates generation of recombinant L-asparaginase.

Exemplary target protease genes include those proteases classified as Aminopeptidases; Dipeptidases; Dipeptidyl-peptidases and tripeptidyl peptidases; Peptidyl-dipeptidases; Serine-type carboxypeptidases; Metallocarboxypeptidases; Cysteine-type carboxypeptidases; Omegapeptidases; Serine proteinases; Cysteine proteinases; Aspartic proteinases; Metallo proteinases; or Proteinases of unknown mechanism.

Aminopeptidases include cytosol aminopeptidase (leucyl aminopeptidase), membrane alanyl aminopeptidase, cystinyl aminopeptidase, tripeptide aminopeptidase, prolyl aminopeptidase, arginyl aminopeptidase, glutamyl aminopeptidase, x-pro aminopeptidase, bacterial leucyl aminopeptidase, thermophilic aminopeptidase, clostridial aminopeptidase, cytosol alanyl aminopeptidase, lysyl aminopeptidase, x-trp aminopeptidase, tryptophanyl aminopeptidase, methionyl aminopeptidas, d-stereospecific aminopeptidase, aminopeptidase ey. Dipeptidases include x-his dipeptidase, x-arg dipeptidase, x-methyl-his dipeptidase, cys-gly dipeptidase, glu-glu dipeptidase, pro-x dipeptidase, x-pro dipeptidase, met-x dipeptidase, non-stereospecific dipeptidase, cytosol non-specific dipeptidase, membrane dipeptidase, beta-ala-his dipeptidase. Dipeptidyl-peptidases and tripeptidyl peptidases include dipeptidyl-peptidase i, dipeptidyl-peptidase ii, dipeptidyl peptidase iii, dipeptidyl-peptidase iv, dipeptidyl-dipeptidase, tripeptidyl-peptidase I, tripeptidyl-peptidase II. Peptidyl-dipeptidases include peptidyl-dipeptidase a and peptidyl-dipeptidase b. Serine-type carboxypeptidases include lysosomal pro-x carboxypeptidase, serine-type D-ala-D-ala carboxypeptidase, carboxypeptidase C, carboxypeptidase D. Metallocarboxypeptidases include carboxypeptidase a, carboxypeptidase B, lysine(arginine) carboxypeptidase, gly-X carboxypeptidase, alanine carboxypeptidase, muramoylpentapeptide carboxypeptidase, carboxypeptidase h, glutamate carboxypeptidase, carboxypeptidase M, muramoyltetrapeptide carboxypeptidase, zined-ala-d-ala carboxypeptidase, carboxypeptidase A2, membrane pro-x carboxypeptidase, tubulinyl-tyr carboxypeptidase, carboxypeptidase t. Omegapeptidases include acylaminoacyl-peptidase, peptidyl-glycinamidase, pyroglutamyl-peptidase I, beta-aspartyl-peptidase, pyroglutamyl-peptidase II, n-formylmethionyl-peptidase, pteroylpoly-[gamma]-glutamate carboxypeptidase, gamma-glu-X carboxypeptidase, acylmuramoyl-ala peptidase. Serine proteinases include chymotrypsin, chymotrypsin c, metridin, trypsin, thrombin, coagulation factor Xa, plasmin, enteropeptidase, acrosin, alpha-lytic protease, glutamyl, endopeptidase, cathepsin G, coagulation factor viia, coagulation factor ixa, cucumisi, prolyl oligopeptidase, coagulation factor xia, brachyurin, plasma kallikrein, tissue kallikrein, pancreatic elastase, leukocyte elastase, coagulation factor xiia, chymase, complement component clr55, complement component cls55, classical-complement pathway c3/c5 convertase, complement factor I, complement factor D, alternative-complement pathway c3/c5 convertase, cerevisin, hypodermin C, lysyl endopeptidase, endopeptidase la, gamma-reni, venombin ab, leucyl endopeptidase, tryptase, scutelarin, kexin, subtilisin, oryzin, endopeptidase k, thermomycolin, thermitase, endopeptidase SO, T-plasminogen activator, protein C, pancreatic endopeptidase E, pancreatic elastase ii, IGA-specific serine endopeptidase, U-plasminogen, activator, venombin A, furin, myeloblastin, semenogelase, granzyme A or cytotoxic T-lymphocyte proteinase 1, granzyme B or cytotoxic T-lymphocyte proteinase 2, streptogrisin A, treptogrisin B, glutamyl endopeptidase II, oligopeptidase B, limulus clotting factor c, limulus clotting factor, limulus clotting enzyme, omptin, repressor lexa, bacterial leader peptidase I, togavirin, flavirin. Cysteine proteinases include cathepsin B, papain, ficin, chymopapain, asclepain, clostripain, streptopain, actinide, cathepsin 1, cathepsin H, calpain, cathepsin t, glycyl, endopeptidase, cancer procoagulant, cathepsin S, picornain 3C, picornain 2A, caricain, ananain, stem bromelain, fruit bromelain, legumain, histolysain, interleukin 1-beta converting enzyme. Aspartic proteinases include pepsin A, pepsin B, gastricsin, chymosin, cathepsin D, neopenthesin, renin, retropepsin, pro-opiomelanocortin converting enzyme, aspergillopepsin I, aspergillopepsin II, penicillopepsin, rhizopuspepsin, endothiapepsin, mucoropepsin, candidapepsin, saccharopepsin, rhodotorulapepsin, physaropepsin, acrocylindropepsin, polyporopepsin, pycnoporopepsin, scytalidopepsin a, scytalidopepsin b, xanthomonapepsin, cathepsin e, barrierpepsin, bacterial leader peptidase I, pseudomonapepsin, plasmepsin. Metallo proteinases include atrolysin a, microbial collagenase, leucolysin, interstitial collagenase, neprilysin, envelysin, iga-specific metalloendopeptidase, procollagen N-endopeptidase, thimet oligopeptidase, neurolysin, stromelysin 1, meprin A, procollagen C-endopeptidase, peptidyl-lys metalloendopeptidase, astacin, stromelysin, 2, matrilysin gelatinase, aeromonolysin, pseudolysin, thermolysin, bacillolysin, aureolysin, coccolysin, mycolysin, beta-lytic metalloendopeptidase, peptidyl-asp metalloendopeptidase, neutrophil collagenase, gelatinase B, leishmanolysin, saccharolysin, autolysin, deuterolysin, serralysin, atrolysin B, atrolysin C, atroxase, atrolysin E, atrolysin F, adamalysin, horrilysin, ruberlysin, bothropasin, bothrolysin, ophiolysin, trimerelysin I, trimerelysin II, mucrolysin, pitrilysin, insulysin, O-syaloglycoprotein endopeptidase, russellysin, mitochondrial, intermediate, peptidase, dactylysin, nardilysin, magnolysin, meprin B, mitochondrial processing peptidase, macrophage elastase, choriolysin, toxilysin. Proteinases of unknown mechanism include thermopsin and multicatalytic endopeptidase complex.

Certain proteases have both protease and chaperone-like activity. When these proteases are negatively affecting protein yield and/or quality it is often useful to specifically delete their protease activity, and they are overexpressed when their chaperone activity may positively affect protein yield and/or quality. These proteases include, but are not limited to: Hsp 100 (Clp/Hsl) family members RXF04587.1 (clpA), RXF08347.1, RXF04654.2 (clpX), RXF04663.1, RXF01957.2 (hslU), RXF01961.2 (hslV); Peptidyl-prolyl cis-trans isomerase family member RXF05345.2 (ppiB); Metallopeptidase M20 family member RXF04892.1 (aminohydrolase); Metallopeptidase M24 family members RXF04693.1 (methionine aminopeptidase) and RXF03364.1 (methionine aminopeptidase); and Serine Peptidase S26 signal peptidase I family member RXF01181.1 (signal peptidase).

In embodiments a host strain useful for expressing a recombinant L-asparaginase, in the methods of the invention is a *Pseudomonas* host strain, e.g., *P. fluorescens*, having a protease deficiency or inactivation (resulting from, e.g., a deletion, partial deletion, or knockout) and/or overexpressing a folding modulator, e.g., from a plasmid or the bacterial chromosome. In embodiments, the host strain is deficient in at least one protease selected from Lon, HslUV, DegP1, DegP2, Prc, AprA, DegP2 S219A, Prc1, and AprA. In embodiments, the host strain overexpresses a folding modulator selected from LepB, Tig, and DsbAC-Skp, (i.e., the combination of DsbA, DsbC and Skp; Skp is OmpH RXF4702.1, set forth as SEQ ID NO: 59 disclosed in U.S. Pub. 2019/0127742, with an example of a coding sequence set forth as SEQ ID NO: 60 disclosed in U.S. Pub. 2019/0127742). In a DsbAC-Skp overexpressor host, folding modulators DsbA, DsbC and Skp (SEQ ID NOS: 25 and 26 of U.S. Pat. No. 9,394,571 and SEQ ID NO: 60 disclosed in U.S. Pub. 2019/0127742) can be expressed from an operon. In embodiments, the host strain is deficient in at least one protease selected from Lon, HslUV, DegP1, DegP2, Prc, AprA, DegP2 S219A, Prc1, and AprA, and overexpresses a folding modulator selected from LepB, Tig, and DsbAC-Skp. In any of the above embodiments, the host strain expresses the auxotrophic markers pyrF and proC, and has a protease deficiency and/or overexpresses a folding modulator. In embodiments, the host strain expresses any other suitable selection marker known in the art. In any of the above embodiments, an asparaginase, e.g., a native Type I and/or Type II asparaginase, is inactivated in the host strain. In embodiments, the host strain is a Pseudomonadales host cell is: deficient in Lon and HslU/V; deficient in Lon, DegP1, DegP2, Prc, and AprA; deficient in Lon, DegP1, DegP2 S219A, Prc1, and AprA, and overexpresses DsbAC-Skp; deficient in AspG1 and/or AspG2; deficient in AspG1 and/or AspG2, and overexpresses Tig; deficient in AspG1 and/or AspG2, and overexpresses LepB; deficient in AspG1 and/or AspG2, and deficient in Lon and HslU/V; a host cell that is deficient in AspG1 and/or AspG2, and deficient in Lon, DegP1, DegP2, Prc, and AprA; or a host cell that is deficient in AspG1 and/or AspG2, Lon, DegP1, DegP2, Prc1, and AprA, and overexpresses DsbAC-Skp.

These and other proteases and folding modulators are known in the art and described in the literature, e.g., in U.S. Pat. No. 8,603,824. For example, Table D of the patent describes Tig (tig, Trigger factor, FKBP type ppiase (ec 5.2.1.8) RXF04655, UniProtKB-POA850 (TIG_ECOLI)). WO 2008/134461 and U.S. Pat. No. 9,394,571, titled "Method for Rapidly Screening Microbial Hosts to Identify Certain Strains with Improved Yield and/or Quality in the Expression of Heterologous Proteins," and incorporated by reference in its entirety herein, describe Tig (RXF04655.2, SEQ ID NO: 34 therein), LepB (RXF01181.1, SEQ ID NO: 56 therein), DegP1 (RXF01250, SEQ ID NO: 57 therein), AprA (RXF04304.1, SEQ ID NO: 86 therein), Prc1 (RXF06586.1, SEQ ID NO: 120 therein), DegP2, (RXF07210.1, SEQ ID NO: 124 therein), Lon (RXF04653, SEQ ID NO: 92 therein); DsbA (RXF01002.1, SEQ ID NO: 25 therein), and DsbC (RXF03307.1, SEQ ID NO: 26 therein). These sequences and those for other proteases and folding modulators also are set forth in U.S. Pat. No. 9,580,719 (Table of SEQ ID NOS in columns 93-98 therein). For example, U.S. Pat. No. 9,580,719 provides the sequence encoding HslU (RXF01957.2) and HslV (RXF01961.2) as SEQ ID NOS 18 and 19, respectively.

F. Codon Optimization

In one embodiment, the methods herein comprise expression of recombinant L-asparaginase from a construct that has been optimized for codon usage in a strain of interest. In embodiments, the strain is a *Pseudomonas* host cell, e.g., *Pseudomonas fluorescens*. Methods for optimizing codons to improve expression in bacterial hosts are known in the art and described in the literature. For example, optimization of codons for expression in a *Pseudomonas* host strain is described, e.g., in U.S. Pat. App. Pub. No. 2007/0292918, "Codon Optimization Method," incorporated herein by reference in its entirety.

In heterologous expression systems, optimization steps may improve the ability of the host to produce the foreign protein. Protein expression is governed by a host of factors including those that affect transcription, mRNA processing, and stability and initiation of translation. The polynucleotide optimization steps may include steps to improve the ability of the host to produce the foreign protein as well as steps to assist the researcher in efficiently designing expression constructs. Optimization strategies may include, for example, the modification of translation initiation regions, alteration of mRNA structural elements, and the use of different codon biases. Methods for optimizing the nucleic acid sequence of to improve expression of a heterologous protein in a bacterial host are known in the art and described in the literature. For example, optimization of codons for expression in a *Pseudomonas* host strain is described, e.g., in U.S. Pat. App. Pub. No. 2007/0292918, "Codon Optimization Method," incorporated herein by reference in its entirety.

Optimization addresses any of a number of sequence features of the heterologous gene. As a specific example, a rare codon-induced translational pause often results in reduced heterologous protein expression. A rare codon-induced translational pause includes the presence of codons in the polynucleotide of interest that are rarely used in the host organism may have a negative effect on protein translation due to their scarcity in the available tRNA pool. One method of improving optimal translation in the host organism includes performing codon optimization which sometimes results in rare host codons being removed from the synthetic polynucleotide sequence.

Alternate translational initiation also sometimes results in reduced heterologous protein expression. Alternate translational initiation include a synthetic polynucleotide sequence inadvertently containing motifs capable of functioning as a ribosome binding site (RBS). These sites, in some cases, result in initiating translation of a truncated protein from a gene-internal site. One method of reducing the possibility of producing a truncated protein, which are often difficult to remove during purification, includes eliminating putative internal RBS sequences from an optimized polynucleotide sequence.

Repeat-induced polymerase slippage often results in reduced heterologous protein expression. Repeat-induced polymerase slippage involves nucleotide sequence repeats that have been shown to cause slippage or stuttering of DNA polymerase which sometimes results in frameshift mutations. Such repeats also often cause slippage of RNA polymerase. In an organism with a high G+C content bias, there is sometimes a higher degree of repeats composed of G or C nucleotide repeats. Therefore, one method of reducing the possibility of inducing RNA polymerase slippage, includes altering extended repeats of G or C nucleotides.

Interfering secondary structures also sometimes result in reduced heterologous protein expression. Secondary structures often sequester the RBS sequence or initiation codon and have been correlated to a reduction in protein expression. Stem loop structures are also often involved in transcriptional pausing and attenuation. An optimized polynucleotide sequence usually contains minimal secondary structures in the RBS and gene coding regions of the nucleotide sequence to allow for improved transcription and translation.

Another feature that sometimes effect heterologous protein expression is the presence of restriction sites. By removing restriction sites that could interfere with subsequent sub-cloning of transcription units into host expression vectors a polynucleotide sequence is optimized.

For example, the optimization process often begins by identifying the desired amino acid sequence to be heterologously expressed by the host. From the amino acid sequence a candidate polynucleotide or DNA is designed. During the design of the synthetic DNA sequence, the frequency of codon usage is often compared to the codon usage of the host expression organism and rare host codons are removed from the synthetic sequence. Additionally, the synthetic candidate DNA sequence is sometimes modified in order to remove undesirable enzyme restriction sites and add or remove any desired signal sequences, linkers or untranslated regions. The synthetic DNA sequence is often analyzed for the presence of secondary structure that may interfere with the translation process, such as G/C repeats and stem-loop structures. Before the candidate DNA sequence is synthesized, the optimized sequence design is often be checked to verify that the sequence correctly encodes the desired amino acid sequence. Finally, the candidate DNA sequence is synthesized using DNA synthesis techniques, such as those known in the art.

In another embodiment herein, the general codon usage in a host organism, such as *P. fluorescens*, is often utilized to optimize the expression of the heterologous polynucleotide sequence. The percentage and distribution of codons that rarely would be considered as preferred for a particular amino acid in the host expression system is evaluated. Values of 5% and 10% usage is often used as cutoff values for the determination of rare codons. For example, the codons listed in Table 4 have a calculated occurrence of less than 5% in the *P. fluorescens* MB214 genome and would be generally avoided in an optimized gene expressed in a *P. fluorescens* host.

Examples of codons occurring at less than 5% in *P. fluorescens* according to the methods herein include those specified in U.S. Pat. App. Pub. No. 2019/0127742, which is incorporated by reference herein, specifically for the examples listed in Table 4.

The present disclosure contemplates the use of any recombinant L-asparaginase coding sequence, including any sequence that has been optimized for expression in the *Pseudomonas* host cell being used. Sequences contemplated for use are often optimized to any degree as desired, including, but not limited to, optimization to eliminate: codons occurring at less than 5% in the *Pseudomonas* host cell, codons occurring at less than 10% in the *Pseudomonas* host cell, a rare codon-induced translational pause, a putative internal RBS sequence, an extended repeat of G or C nucleotides, an interfering secondary structure, a restriction site, or combinations thereof.

Furthermore, the amino acid sequence of any secretion leader useful in practicing the methods provided herein is encoded by any appropriate nucleic acid sequence. Codon optimization for expression in *E. coli* is described, e.g., by Welch, et al., 2009, PLOS One, "Design Parameters to Control Synthetic Gene Expression in *Escherichia coli*," 4(9): e7002, Ghane, et al., 2008, Krishna R. et al., (2008) Mol Biotechnology "Optimization of the AT-content of Codons Immediately Downstream of the Initiation Codon and Evaluation of Culture Conditions for High-level Expression of Recombinant Human G-CSF in *Escherichia coli*," 38:221-232.

G. High Throughput Screens

In some embodiments, a high throughput screen is often conducted to determine optimal conditions for expressing soluble recombinant L-asparaginase. The conditions that be varied in the screen include, for example, the host cell, genetic background of the host cell (e.g., deletions of different proteases), type of promoter in an expression construct, type of secretion leader fused to encoded recombinant L-asparaginase, temperature of growth, OD of induction when an inducible promoter is used, amount of inducer added (e.g. amount of IPTG used for induction when a lacZ promoter or derivative thereof is used), duration of protein induction, temperature of growth following addition of an inducing agent to a culture, rate of agitation of culture, method of selection for plasmid maintenance, volume of culture in a vessel, and method of cell lysing.

In some embodiments, a library (or "array") of host strains is provided, wherein each strain (or "population of host cells") in the library has been genetically modified to modulate the expression of one or more target genes in the host cell. An "optimal host strain" or "optimal expression system" is often identified or selected based on the quantity, quality, and/or location of the expressed protein of interest compared to other populations of phenotypically distinct host cells in the array. Thus, an optimal host strain is the strain that produces the polypeptide of interest according to a desired specification. While the desired specification will vary depending on the polypeptide being produced, the specification includes the quality and/or quantity of protein, whether the protein is sequestered (e.g., in inclusion bodies) or secreted, protein folding, and the like. For example, the optimal host strain or optimal expression system produces a yield, characterized by the amount of soluble heterologous protein, the amount of recoverable heterologous protein, the amount of properly processed heterologous protein, the amount of properly folded heterologous protein, the amount of active heterologous protein, and/or the total amount of heterologous protein, of a certain absolute level or a certain level relative to that produced by an indicator strain, i.e., a strain used for comparison.

Methods of screening microbial hosts to identify strains with improved yield and/or quality in the expression of heterologous proteins are described, for example, in U.S. Patent Application Publication No. 20080269070.

H. Bacterial Growth Conditions

Growth conditions useful in the methods herein often comprise a temperature of about 4° C. to about 42° C. and a pH of about 5.7 to about 8.8. When an expression construct with a lacZ promoter or derivative thereof is used, expression is often induced by adding IPTG to a culture at a final concentration of about 0.01 mM to about 1.0 mM.

The pH of the culture is sometimes maintained using pH buffers and methods known to those of skill in the art. Control of pH during culturing also is often achieved using aqueous ammonia. In embodiments, the pH of the culture is about 5.7 to about 8.8. In certain embodiments, the pH is about 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, or 8.8 In other embodiments, the pH is about 5.7 to 5.9, 5.8 to 6.0, 5.9 to 6.1, 6.0 to 6.2, 6.1 to 6.3, 6.2 to 6.5, 6.4 to 6.7, 6.5 to 6.8, 6.6 to 6.9, 6.7 to 7.0, 6.8 to 7.1, 6.9 to 7.2, 7.0 to 7.3, 7.1 to 7.4, 7.2 to 7.5, 7.3 to 7.6, 7.4 to 7.7, 7.5 to 7.8, 7.6 to 7.9, 7.7 to 8.0, 7.8 to 8.1, 7.9 to 8.2, 8.0 to 8.3, 8.1 to 8.4, 8.2 to 8.5, 8.3 to 8.6, 8.4 to 8.7, or 8.5 to 8.8. In yet other embodiments, the pH is about 5.7 to 6.0, 5.8 to 6.1, 5.9 to 6.2, 6.0 to 6.3, 6.1 to 6.4, or 6.2 to 6.5. In certain embodiments, the pH is about 5.7 to about 6.25. In some embodiments, the pH is about 5.0 to about 8.0.

In embodiments, the growth temperature is maintained at about 4° C. to about 42° C. In certain embodiments, the growth temperature is about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., or about 42° C. In other embodiments, the growth temperature is maintained at about 25° C. to about 27° C., about 25° C. to about 28° C., about 25° C. to about 29° C., about 25° C. to about 30° C., about 25° C. to about 31° C., about 25° C. to about 32° C., about 25° C. to about 33° C., about 26° C. to about 28° C., about 26° C. to about 29° C., about 26° C. to about 30° C., about 26° C. to about 31° C., about 26° C. to about 32° C., about 27° C. to about 29° C., about 27° C. to about 30° C., about 27° C. to about 31° C., about 27° C. to about 32° C., about 26° C. to about 33° C., about 28° C. to about 30° C., about 28° C. to about 31° C., about 28° C. to about 32° C., about 29° C. to about 31° C., about 29° C. to about 32° C., about 29° C. to about 33° C., about 30° C. to about 32° C., about 30° C. to about 33° C., about 31° C. to about 32° C., about 33° C. to about 31° C. to about 32° C., about 30° C. to about 33° C., or about 32° C. to about 33° C. In embodiments, the growth temperature is maintained at about 22° C. to about 33° C. In other embodiments, the temperature is changed during culturing. In certain embodiments, the temperature is maintained at about 30° C. to about 32° C. before an agent to induce expression from the construct encoding the polypeptide or protein of interest is added to the culture, and the temperature is dropped to about 25° C. to about 27° C. after adding an agent to induce expression, e.g., IPTG is added to the culture. In one embodiment, the temperature is maintained at about 30° C. before an agent to induce expression from the construct encoding the polypeptide or protein of interest is added to the culture, and the temperature is dropped to about 25° C. after adding an agent to induce expression is added to the culture.

I. Induction

In one embodiment, fermentation is used in the methods of producing a recombinant L-asparaginase. The expression system according to the present disclosure is cultured in any fermentation format. For example, batch, fed-batch, semi-continuous, and continuous fermentation modes may be employed herein.

In embodiments, the fermentation medium may be selected from among rich media, minimal media, and mineral salts media. In other embodiments either a minimal medium or a mineral salts medium is selected. In certain embodiments, a mineral salts medium is selected.

Mineral salts media consists of mineral salts and a carbon source such as, e.g., glucose, sucrose, or glycerol. Examples of mineral salts media include, e.g., M9 medium, *Pseudomonas* medium (ATCC 179), and Davis and Mingioli medium (see, B D Davis & E S Mingioli (1950) J. Bact. 60:17-28). The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. Typically, no organic nitrogen source, such as peptone, tryptone, amino acids, or a yeast extract, is included in a mineral salts medium. Instead, an inorganic nitrogen source is used and this may be selected from among, e.g., ammonium salts, aqueous ammonia, and gaseous ammonia. A mineral salts medium will typically contain glucose or glycerol as the carbon source. In comparison to mineral salts media, minimal media often contains mineral salts and a carbon source, but is often supplemented with, e.g., low levels of amino acids, vitamins, peptones, or other ingredients, though these are added at very minimal levels. Media is often prepared using the methods described in the art, e.g., in U.S. Pat. App. Pub. No. 2006/0040352, referenced and incorporated by reference above. Details of cultivation procedures and mineral salts media useful in the methods herein are described by Riesenberg, D et al., 1991, "High cell density cultivation of *Escherichia coli* at controlled specific growth rate," J. Biotechnol. 20 (1):17-27.

Fermentation may be performed at any scale. The expression systems according to the present disclosure are useful for recombinant protein expression at any scale. Thus, e.g., microliter-scale, milliliter scale, centiliter scale, and deciliter scale fermentation volumes may be used, and 1 Liter scale and larger fermentation volumes are often used.

In embodiments, the fermentation volume is at or above about 1 Liter. In embodiments, the fermentation volume is about 0.5 liters to about 100 liters. In embodiments, the fermentation volume is about 0.5 liters, about 1 liter, about 2 liters, about 3 liters, about 4 liters, about 5 liters, about 6 liters, about 7 liters, about 8 liters, about 9 liters, or about 10 liters. In embodiments, the fermentation volume is about 0.5 liters to about 2 liters, about 0.5 liters to about 5 liters, about 0.5 liters to about 10 liters, about 0.5 liters to about 25 liters, about 0.5 liters to about 50 liters, about 0.5 liters to about 75 liters, about 10 liters to about 25 liters, about 25 liters to about 50 liters, or about 50 liters to about 100 liters. In other embodiments, the fermentation volume is at or above 5 Liters, 10 Liters, 15 Liters, 20 Liters, 25 Liters, 50 Liters, 75 Liters, 100 Liters, 200 Liters, 500 Liters, 1,000 Liters, 2,000 Liters, 5,000 Liters, 10,000 Liters, or 50,000 Liters.

J. Fermentation Format

In one embodiment, fermentation is used in the methods of producing a recombinant L-asparaginase described herein. The expression system according to the present disclosure is cultured in any fermentation format. For example, batch, fed-batch, semi-continuous, and continuous fermentation modes may be employed herein.

In embodiments, the fermentation medium may be selected from among rich media, minimal media, and mineral salts media. In other embodiments either a minimal medium or a mineral salts medium is selected. In certain embodiments, a mineral salts medium is selected.

Mineral salts media consists of mineral salts and a carbon source such as, e.g., glucose, sucrose, or glycerol. Examples of mineral salts media include, e.g., M9 medium, *Pseudomonas* medium (ATCC 179), and Davis and Mingioli medium (see, B D Davis & E S Mingioli (1950) J. Bact. 60:17-28). The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. Typically, no organic nitrogen source, such as peptone, tryptone, amino acids, or a yeast extract, is included in a mineral salts medium. Instead, an inorganic nitrogen source is used and this may be selected from among, e.g., ammonium salts, aqueous ammonia, and gaseous ammonia. A mineral salts medium will typically contain glucose or glycerol as the carbon source. In comparison to mineral salts media, minimal media often contains mineral salts and a carbon source, but is often supplemented with, e.g., low levels of amino acids, vitamins, peptones, or other ingredients, though these are added at very minimal levels. Media is often prepared using the methods described in the art, e.g., in U.S. Pat. App. Pub. No. 2006/0040352, referenced and incorporated by reference above. Details of cultivation procedures and mineral salts media useful in the methods herein are described by Riesenberg, D et al., 1991, "High cell density cultivation of *Escherichia coli* at controlled specific growth rate," J. Biotechnol. 20 (1): 17-27.

Fermentation may be performed at any scale. The expression systems according to the present disclosure are useful for recombinant protein expression at any scale. Thus, e.g., microliter-scale, milliliter scale, centiliter scale, and deciliter scale fermentation volumes may be used, and 1 Liter scale and larger fermentation volumes are often used.

In embodiments, the fermentation volume is at or above about 1 Liter. In embodiments, the fermentation volume is about 0.5 liters to about 100 liters. In embodiments, the fermentation volume is about 0.5 liters, about 1 liter, about 2 liters, about 3 liters, about 4 liters, about 5 liters, about 6 liters, about 7 liters, about 8 liters, about 9 liters, or about 10 liters. In embodiments, the fermentation volume is about 0.5 liters to about 2 liters, about 0.5 liters to about 5 liters, about 0.5 liters to about 10 liters, about 0.5 liters to about 25 liters, about 0.5 liters to about 50 liters, about 0.5 liters to about 75 liters, about 10 liters to about 25 liters, about 25 liters to about 50 liters, or about 50 liters to about 100 liters. In other embodiments, the fermentation volume is at or above 5 Liters, 10 Liters, 15 Liters, 20 Liters, 25 Liters, 50 Liters, 75 Liters, 100 Liters, 200 Liters, 500 Liters, 1,000 Liters, 2,000 Liters, 5,000 Liters, 10,000 Liters, or 50,000 Liters.

K. Protein Analysis

In embodiments, recombinant L-asparaginase produced by the methods provided herein is analyzed. Recombinant crisantaspase is sometimes analyzed, for example, by biolayer interferometry, SDS-PAGE, Western blot, Far Western blot, ELISA, absorbance, or mass spectrometry (e.g., tandem mass spectrometry).

In some embodiments, the concentration and/or amounts of recombinant L-asparaginase generated are determined, for example, by Bradford assay, absorbance, Coomassie staining, mass spectrometry, etc.

Protein yield in the insoluble and soluble fractions as described herein are often determined by methods known to those of skill in the art, for example, by capillary gel electrophoresis (CGE), and Western blot analysis. Soluble fractions are often evaluated, for example, using biolayer interferometry.

The recombinant L-asparaginase monomer of the present disclosure is capable of forming active tetramer, e.g., in cell lysate, cell sonicate, and upon further purification. Following expression of the recombinant L-asparaginase in a bacterial expression system, e.g., in a E. coli or Pseudomonas host strain, the recombinant protein can be purified using any suitable method known in the art, e.g., to remove host cell proteins. Purification methods can include, e.g., cation exchange chromatography, anion exchange chromatography, size exclusion chromatography, high performance liquid chromatography (HPLC), or a combination of these and/or other known methods. Asparaginase protein purification is described in the literature, e.g., in U.S. Pat. No. 5,310,670, "Method for the purification of Erwinia L-asparaginase," and U.S. Pat. No. 8,323,948, "Asparaginases and uses thereof," each incorporated by reference herein in its entirety. A type II asparaginase expressed in P. fluorescens is present as active, tetrameric asparaginase enzyme in sonicates.

In embodiments, a measurable characteristic (e.g., activity, size, length, or other characteristic indicative of active and/or intact protein) of an amount of an unpurified or purified asparaginase sample is compared with the same measurable characteristic of the same amount of an asparaginase standard sample (e.g., a commercially obtained asparaginase). It is understood that the amount of asparaginase protein in a sample can be determined by any suitable assay known in the art for protein measurement, and the activity by any suitable assay, e.g., as described herein.

Useful measures of protein yield include, e.g., the amount of recombinant protein per culture volume (e.g., grams or milligrams of protein/liter of culture), percent or fraction of recombinant protein measured in the insoluble pellet obtained after lysis (e.g., amount of recombinant protein in extract supernatant/amount of protein in insoluble fraction), percent or fraction of soluble recombinant protein, percent or fraction of active protein (e.g., amount of active protein/amount protein used in the assay), percent or fraction of total cell protein (tcp), amount of protein/cell, and percent dry biomass.

In embodiments, the methods herein are used to obtain a yield of soluble recombinant L-asparaginase of the present disclosure, e.g., monomer or tetramer, of about 20% to about 90% total cell protein. In certain embodiments, the yield of soluble recombinant crisantaspase is about 20% total cell protein, about 25% total cell protein, about 30% total cell protein, about 31% total cell protein, about 32% total cell protein, about 33% total cell protein, about 34% total cell protein, about 35% total cell protein, about 36% total cell protein, about 37% total cell protein, about 38% total cell protein, about 39% total cell protein, about 40% total cell protein, about 41% total cell protein, about 42% total cell protein, about 43% total cell protein, about 44% total cell protein, about 45% total cell protein, about 46% total cell protein, about 47% total cell protein, about 48% total cell protein, about 49% total cell protein, about 50% total cell protein, about 51% total cell protein, about 52% total cell protein, about 53% total cell protein, about 54% total cell protein, about 55% total cell protein, about 56% total cell protein, about 57% total cell protein, about 58% total cell protein, about 59% total cell protein, about 60% total cell protein, about 65% total cell protein, about 70% total cell protein, about 75% total cell protein, about 80% total cell protein, about 85% total cell protein, or about 90% total cell protein. In some embodiments, the yield of soluble recombinant crisantaspase is about 20% to about 25% total cell protein, about 20% to about 30% total cell protein, about 20% to about 35% total cell protein, about 20% to about 40% total cell protein, about 20% to about 45% total cell protein, about 20% to about 50% total cell protein, about 20% to about 55% total cell protein, about 20% to about 60% total cell protein, about 20% to about 65% total cell protein, about 20% to about 70% total cell protein, about 20% to about 75% total cell protein, about 20% to about 80% total cell protein, about 20% to about 85% total cell protein, about 20% to about 90% total cell protein, about 25% to about 90% total cell protein, about 30% to about 90% total cell protein, about 35% to about 90% total cell protein, about 40% to about 90% total cell protein, about 45% to about 90% total cell protein, about 50% to about 90% total cell protein, about 55% to about 90% total cell protein, about 60% to about 90% total cell protein, about 65% to about 90% total cell protein, about 70% to about 90% total cell protein, about 75% to about 90% total cell protein, about 80% to about 90% total cell protein, about 85% to about 90% total cell protein, about 20% to about 40% total cell protein, about 25% to about 40% total cell protein, about 35% to about 40% total cell protein, about 20% to about 35% total cell protein, about 20% to about 30% total cell protein, or about 20% to about 25% total cell protein. In some embodiments, the yield of soluble recombinant crisantaspase is about 20% to about 40% total cell protein.

In embodiments, the methods herein are used to obtain a yield of soluble recombinant L-asparaginase of the present disclosure, e.g., monomer or tetramer, of about 1 gram per liter to about 50 grams per liter. In certain embodiments, the yield of soluble recombinant L-asparaginase is about 1 gram per liter, about 2 grams per liter, about 3 grams per liter, about 4 grams per liter, about 5 grams per liter, about 6 grams per liter, about 7 grams per liter, about 8 grams per liter, about 9 grams per liter, about 10 gram per liter, about 11 grams per liter, about 12 grams per liter, about 13 grams per liter, about 14 grams per liter, about 15 grams per liter, about 16 grams per liter, about 17 grams per liter, about 18 grams per liter, about 19 grams per liter, about 20 grams per liter, about 21 grams per liter, about 22 grams per liter, about 23 grams per liter about 24 grams per liter, about 25 grams per liter, about 26 grams per liter, about 27 grams per liter, about 28 grams per liter, about 30 grams per liter, about 35 grams per liter, about 40 grams per liter, about 45 grams per liter about 50 grams per liter about 1 gram per liter to about 5 grams per liter, about 1 gram to about 10 grams per liter, about 10 gram per liter to about 12 grams per liter, about 10 grams per liter to about 13 grams per liter, about 10 grams per liter to about 14 grams per liter, about 10 grams per liter to about 15 grams per liter, about 10 grams per liter to about 16 grams per liter, about 10 grams per liter to about 17 grams per liter, about 10 grams per liter to about 18 grams per liter, about 10 grams per liter to about 19 grams per liter, about 10 grams per liter to about 20 grams per liter, about 10 grams per liter to about 21 grams per liter, about 10 grams per liter to about 22 grams per liter, about 10 grams per liter to about 23 grams per liter, about 10 grams per liter to about 24 grams per liter, about 10 grams per liter to about 25 grams per liter, about 10 grams per liter to about 30 grams per liter, about 10 grams per liter to about 40 grams per liter, about 10 grams per liter to about 50 grams per liter, about 10 gram per liter to about 12 grams per liter, about 12 grams per liter to about 14 grams per liter, about 14 grams per liter to about 16 grams per liter, about 16 grams per liter to about 18 grams per liter, about 18 grams per liter to about 20 grams per liter, about 20 grams per liter to about 22 grams per liter, about 22 grams per liter to about 24 grams per liter, about 23 grams per liter to about 25 grams per liter, about 10 grams per liter to about 25 grams per liter, about 11 grams per liter to about 25 grams per liter, about 12 grams per liter to about 25 grams per liter, about 13 grams per liter to about 25 grams per liter, about 14 grams per liter to about 25 grams per liter, about 15 grams per liter to about 25 grams per liter, about 16 grams per liter to about 25 grams per liter, about 17 grams per liter to about 25 grams per liter, about 18 grams per liter to about 25 grams per liter, about 19 grams per liter to about 25 grams per liter, about 20 grams per liter to about 25 grams per liter, about 21 grams per liter to about 25 grams per liter, about 22 grams per liter to about 25 grams per liter, about 23 grams per liter to about 25 grams per liter, or about 24 grams per liter to about 25 grams per liter. In embodiments, the soluble recombinant protein yield is about 10 gram per liter to about 13 grams per liter, about 12 grams per liter to about 14 grams per liter, about 13 grams per liter to about 15 grams per liter, about 14 grams per liter to about 16 grams per liter, about 15 grams per liter to about 17 grams per liter, about 16 grams per liter to about 18 grams per liter, about 17 grams per liter to about 19 grams per liter, about 18 grams per liter to about 20 grams per liter, about 20 grams per liter to about 22 grams per liter, about 22 grams per liter to about 24 grams per liter, or about 23 grams per liter to about 25 grams per liter. In embodiments, the soluble recombinant protein yield is about 10 grams per liter to about 25 grams per liter, about 12 gram per liter to about 24 grams per liter, about 14 grams per liter to about 22 grams per liter, about 16 grams per liter to about 20 grams per liter, or about 18 grams per liter to about 20 grams per liter. In embodiments, the extracted protein yield is about 5 grams per liter to about 15 grams per liter, about 5 gram per liter to about 25 grams per liter, about 10 grams per liter to about 15 grams per liter, about 10 grams per liter to about 25 grams per liter, about 15 grams per liter to about 20 grams per liter, about 15 grams per liter to about 25 grams per liter, or about 18 grams per liter to about 25 grams per liter. In certain embodiments, the yield of soluble recombinant crisantaspase is about 10 grams per liter to about 25 grams per liter.

In embodiments, the amount of a recombinant L-asparaginase of the present disclosure, e.g., monomer or tetramer, detected in the soluble fraction is about 10% to about 100% of the amount of the total recombinant crisantaspase produced. In embodiments, this amount is about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 99%, or about 100% of the amount of the total recombinant crisantaspase produced. In embodiments, this amount is about 10% to about 20%, 20% to about 50%, about 25% to about 50%, about 25% to about 50%, about 25% to about 95%, about 30% to about 50%, about 30% to about 40%, about 30% to about 60%, about 30% to about 70%, about 35% to about 50%, about 35% to about 70%, about 35% to about 75%, about 35% to about 95%, about 40% to about 50%, about 40% to about 95%, about 50% to about 75%, about 50% to about 95%, about 70% to about 95%, or about 80 to about 100% of the amount of the total recombinant crisantaspase produced.

In some embodiments, the amount of a soluble recombinant L-asparaginase of the present disclosure is expressed as a percentage of the total soluble protein produced in a culture. Data expressed in terms of recombinant asparaginase protein weight/volume of cell culture at a given cell density can be converted to data expressed as percent recombinant protein of total cell protein. It is within the capabilities of a skilled artisan to convert volumetric protein yield to % total cell protein, for example, knowing the amount of total cell protein per volume of cell culture at the given cell density. This number can be determined if one knows 1) the cell weight/volume of culture at the given cell density, and 2) the percent of cell weight comprised by total protein. For example, at an OD550 of 1.0, the dry cell weight of E. coli is reported to be 0.5 grams/liter ("Production of Heterologous Proteins from Recombinant DNA Escherichia coli in Bench Fermentors," Lin, N. S., and Swartz, J. R., 1992, METHODS: A Companion to Methods in Enzymology 4: 159-168). A bacterial cell is comprised of polysaccharides, lipids, and nucleic acids, as well as proteins. An E. coli cell is reported to be about 52.4 to 55% protein by references including, but not limited to, Da Silva, N. A., et al., 1986, "Theoretical Growth Yield Estimates for Recombinant Cells," Biotechnology and Bioengineering, Vol. XXVIII: 741-746, estimating protein to make up 52.4% by weight of E. coli cells, and "Escherichia coli and Salmonella typhimurium Cellular and Molecular Biology," 1987, Ed. in Chief Frederick C. Neidhardt, Vol. 1, pp. 3-6, reporting protein content in E. coli as 55% dry cell weight. Using the measurements above (i.e., a dry cell weight of 0.5 grams/liter, and protein as 55% cell weight), the amount of total cell protein per volume of cell culture at an A550 of 1.0 for E. coli is calculated as 275 ug total cell protein/ml/A550. A calculation of total cell protein per volume of cell culture based on wet cell weight can use, e.g., the determination by Glazyrina, et al. (Microbial Cell Factories 2010, 9:42, incorporated herein by reference) that an A600 of 1.0 for E. coli resulted in a wet cell weight of 1.7 grams/liter and a dry cell weight of 0.39 grams/liter. For example, using this wet cell weight to dry cell weight comparison, and protein as 55% dry cell weight as described above, the amount of total cell protein per volume of cell culture at an A600 of 1.0 for E. coli can be calculated as 215 ug total cell protein/ml/A600. For Pseudomonas fluorescens, the amount of total cell protein per volume of cell culture at a given cell density is similar to that found for E. coli. P. fluorescens, like E. coli, is a gram-negative, rod-shaped bacterium. The dry cell weight of P. fluorescens ATCC 11150 as reported by Edwards, et al., 1972, "Continuous Culture of Pseudomonas fluorescens with Sodium Maleate as a Carbon Source," Biotechnology and Bioengineering, Vol. XIV, pages 123-147, is 0.5 grams/liter/A500. This is the same weight reported by Lin, et al., for E. coli at an A550 of 1.0. Light scattering measurements made at 500 nm and at 550 nm are expected to be very similar. The percent of cell weight comprised by total cell protein for P. fluorescens HK44 is described as 55% by, e.g., Yarwood, et al., July 2002, "Noninvasive Quantitative Measurement of Bacterial Growth in Porous Media under Unsaturated-Flow Conditions," Applied and Environmental Microbiology 68(7): 3597-3605. This percentage is similar to or the same as those given for *E. coli* by the references described above.

In embodiments, the amount of a soluble recombinant L-asparaginase of the present disclosure, e.g., monomer or tetramer, produced is about 0.1% to about 95% of the total soluble protein produced in a culture. In embodiments, this amount is more than about 0.1%, 0.5%, 1%, 5%, 10%, 15%, 20%, 25%, 30%, 40%, 45%, 50%, 55%, 60%, 65%, 70%, 75%, 80%, 85%, 90%, or 95% of the total soluble protein produced in a culture. In embodiments, this amount is about 0.1%, 0.5%, 1%, 5%, 10%, 15%, 20%, 25%, 30%, 40%, 45%, 50%, 55%, 60%, 65%, 70%, 75%, 80%, 85%, 90%, or 95% of the total soluble protein produced in a culture. In embodiments, this amount is about 5% to about 95%, about 10% to about 85%, about 20% to about 75%, about 30% to about 65%, about 40% to about 55%, about 1% to about 95%, about 5% to about 30%, about 1% to about 10%, about 10% to about 20%, about 20% to about 30%, about 30% to about 40%, about 40% to about 50%, about 50 to about 60%, about 60% to about 70%, or about 80% to about 90% of the total soluble protein produced in a culture.

In embodiments, the amount of soluble recombinant L-asparaginase in the present disclosure, e.g., monomer or tetramer, produced is about 0.1% to about 50% of the dry cell weight (DCW). In embodiments, this amount is more than about 0.1%, 0.5%, 1%, 5%, 10%, 15%, 20%, 25%, 30%, 40%, 45%, or 50% of DCW. In embodiments, this amount is about 0.1%, 0.5%, 1%, 5%, 10%, 15%, 20%, 25%, 30%, 40%, 45%, or 50% of DCW. In embodiments, this amount is about 5% to about 50%, about 10% to about 40%, about 20% to about 30%, about 1% to about 20%, about 5% to about 25%, about 1% to about 10%, about 10% to about 20%, about 20% to about 30%, about 30% to about 40%, or about 40% to about 50% of the total soluble protein produced in a culture.

In embodiments, the yield or amount of cytoplasmically produced soluble recombinant L-asparaginase of the present disclosure, as described in terms of any of these protein measures (e.g., the amount of recombinant protein per culture volume (e.g., grams or milligrams of protein/liter of culture), percent or fraction of recombinant protein measured in the insoluble pellet obtained after lysis (e.g., amount of recombinant protein in extract supernatant/amount of protein in insoluble fraction), percent or fraction of soluble recombinant protein, percent or fraction of active protein (e.g., amount of active protein/amount protein used in the assay), percent or fraction of total cell protein (tcp), amount of protein/cell, and percent dry biomass), is equivalent to or increased relative to the amount of periplasmically produced soluble recombinant crisantaspase obtained under similar or substantially similar conditions (conditions include, e.g., the host cell, genetic background of the host cell (e.g., deletions of different proteases), type of promoter in an expression construct, temperature of growth, OD of induction when an inducible promoter is used, amount of inducer added (e.g. amount of IPTG used for induction when a lacZ promoter or derivative thereof is used), duration of protein induction, temperature of growth following addition of an inducing agent to a culture, rate of agitation of culture, method of selection for plasmid maintenance, volume of culture in a vessel, and method of cell lysing). In embodiments, the yield ratio of cytoplasmically produced soluble recombinant L-asparaginase to periplasmically produced soluble recombinant L-asparaginase obtained under similar or substantially similar conditions is about 1:1 (i.e., 1) to about 5:1 (i.e., 5). In embodiments, the yield ratio of cytoplasmically produced soluble recombinant L-asparaginase to periplasmically produced soluble recombinant L-asparaginase obtained under similar or substantially similar conditions is about 1 to about 5. In embodiments, the yield ratio of cytoplasmically produced soluble recombinant L-asparaginase to periplasmically produced soluble recombinant crisantaspase obtained under similar or substantially similar conditions is at least about 1. In embodiments, the yield ratio of cytoplasmically produced soluble recombinant L-asparaginase to periplasmically produced soluble recombinant L-asparaginase obtained under similar or substantially similar conditions is at most about 5. In embodiments, the yield ratio of cytoplasmically produced soluble recombinant L-asparaginase to periplasmically produced soluble recombinant L-asparaginase obtained under similar or substantially similar conditions is about 1 to about 1.25, about 1 to about 1.5, about 1 to about 1.75, about 1 to about 2, about 1 to about 2.5, about 1 to about 3, about 1 to about 3.5, about 1 to about 4, about 1 to about 4.5, about 1 to about 5, about 1.25 to about 1.5, about 1.25 to about 1.75, about 1.25 to about 2, about 1.25 to about 2.5, about 1.25 to about 3, about 1.25 to about 3.5, about 1.25 to about 4, about 1.25 to about 4.5, about 1.25 to about 5, about 1.5 to about 1.75, about 1.5 to about 2, about 1.5 to about 2.5, about 1.5 to about 3, about 1.5 to about 3.5, about 1.5 to about 4, about 1.5 to about 4.5, about 1.5 to about 5, about 1.75 to about 2, about 1.75 to about 2.5, about 1.75 to about 3, about 1.75 to about 3.5, about 1.75 to about 4, about 1.75 to about 4.5, about 1.75 to about 5, about 2 to about 2.5, about 2 to about 3, about 2 to about 3.5, about 2 to about 4, about 2 to about 4.5, about 2 to about 5, about 2.5 to about 3, about 2.5 to about 3.5, about 2.5 to about 4, about 2.5 to about 4.5, about 2.5 to about 5, about 3 to about 3.5, about 3 to about 4, about 3 to about 4.5, about 3 to about 5, about 3.5 to about 4, about 3.5 to about 4.5, about 3.5 to about 5, about 4 to about 4.5, about 4 to about 5, or about 4.5 to about 5. In embodiments, the yield ratio of cytoplasmically produced soluble recombinant L-asparaginase to periplasmically produced soluble recombinant L-asparaginase obtained under similar or substantially similar conditions is about 1, about 1.25, about 1.5, about 1.75, about 2, about 2.5, about 3, about 3.5, about 4, about 4.5, or about 5.

V. Methods of Treatment and Use of the Recombinant Crisantaspase Protein

A. Diseases or Disorders

The recombinant L-asparaginase of the present disclosure can be used in the treatment of a disease in a human subject, where that disease is treatable by depletion of asparagine. In some embodiments, the human subject has, prior to administration of the recombinant L-asparaginase, experienced silent inactivation of the *E. Coli*-derived asparaginase. In some embodiments, the human subject has, prior to administration of the recombinant L-asparaginase, experienced an allergic reaction to the *E. Coli*-derived asparaginase. In some embodiments, the human subject has, prior to administration of the recombinant L-asparaginase, experienced anaphylaxis to the *E. coli*-derived asparaginase. Non-limiting examples of objective signs of allergy or hypersensitivity include testing "antibody positive" for an asparaginase enzyme.

In some embodiments, the recombinant L-asparaginase of the present disclosure is useful in the treatment or the manufacture of a medicament for use in the treatment of acute lymphoblastic leukemia (ALL). The incidence of relapse in ALL patients following treatment with L-asparaginase remains high, with approximately 10-25% of pediatric ALL patients having early relapse (e.g., some during maintenance phase at 30-36 months post-induction). If a patient treated with *E. coli*-derived L-asparaginase has a relapse, subsequent treatment with *E. coli* preparations could lead to a "vaccination" effect, whereby the *E. coli* preparation has increased immunogenicity during the subsequent administrations. In one embodiment, the recombinant L-asparaginase of the invention may be used in a method of treating patients with relapsed ALL who were previously treated with other asparaginase preparations, in particular those who were previously treated with *E. coli*-derived asparaginases. In some embodiments, the recombinant L-asparaginase administered to the patient with relapsed ALL is conjugated with a PEG moiety. In some embodiments, the recombinant L-asparaginase administered to the patient with relapsed ALL is not conjugated with a PEG moiety. In some embodiments, the recombinant L-asparaginase administered to the patient with relapsed ALL is conjugated with a proline- or alanine-containing peptide. In some embodiments, the recombinant L-asparaginase administered to the patient with relapsed ALL is not conjugated with a proline- or alanine-containing peptide.

In some embodiments, the recombinant L-asparaginase of the present disclosure is useful in the treatment or the manufacture of a medicament for use in the treatment of lymphoblastic lymphoma (LBL). Similarly to patients with ALL, in some embodiments, the recombinant L-asparaginase administered to the patient with relapsed LBL is conjugated with a PEG moiety. In some embodiments, the recombinant L-asparaginase administered to the patient with relapsed LBL is not conjugated with a PEG moiety. In some embodiments, the recombinant L-asparaginase administered to the patient with relapsed LBL is conjugated with a proline- or alanine-containing peptide. In some embodiments, the recombinant L-asparaginase administered to the patient with relapsed LBL is not conjugated with a proline- or alanine-containing peptide.

Diseases or disorders that the recombinant L-asparaginase of the present disclosure is useful in treating include but are not limited to the following: malignancies, or cancers, including but not limited to hematalogic malignancies, lymphoma, non-Hodgkin's lymphoma, NK lymphoma, pancreatic cancer, Hodgkin's disease, large cell immunoblastic lymphoma, acute promyelocytic leukemia, acute myelocytic leukemia, acute myelomonocytic leukemia, acute monocytic leukemia, acute T-cell leukemia, acute myeloid leukemia (AML), biphenotypic B-cell myelomonocytic Leukemia, chronic lymphocytic leukemia, lymphosarcoma, reticulosarcoma, and melanosarcoma, and diffuse large B-cell lymphoma (DLBCL). Other diseases or disorders that the recombinant L-asparaginase is useful in treating are cancers including, but not limited to, renal cell carcinoma, renal cell adenocarcinoma, glioblastoma including glioblastoma multiforma and glioblastoma astrocytoma, medulloblastoma, rhabdomyosarcoma, malignant melanoma, epidermoid carcinoma, squamous cell carcinoma, lung carcinoma including large cell lung carcinoma and small cell lung carcinoma, endometrial carcinoma, ovarian adenocarcinoma, ovarian tetratocarcinoma, cervical adenocarcinoma, breast carcinoma, breast adenocarcinoma, breast ductal carcinoma, pancreatic adenocarcinoma, pancreatic ductal carcinoma, colon carcinoma, colon adenocarcinoma, colorectal adenocarcinoma, bladder transitional cell carcinoma, bladder papilloma, prostate carcinoma, osteosarcoma, epitheloid carcinoma of the bone, prostate carcinoma, and thyroid cancer. The cancer may be a solid cancer, for example lung cancer or breast cancer. Representative non-malignant hematologic diseases which respond to asparagine depletion include immune system-mediated blood diseases, including but not limited to infectious diseases such as those caused by HIV infection (i.e., AIDS). Non-hematologic diseases associated with asparagine dependence include autoimmune diseases, for example rheumatoid arthritis, collagen vascular diseases, AIDS, osteoarthritis, Issac's syndrome, psoriasis, insulin dependent diabetes mellitus, multiple sclerosis, sclerosing panencephalitis, systemic lupus erythematosus (SLE), rheumatic fever, inflammatory bowel disease (e.g., ulcerative colitis and Crohn's disease), primary billiary cirrhosis, chronic active hepatitis, glomerulonephritis, myasthenia gravis, pemphigus vulgaris, and Graves' disease. Cells suspected of causing disease can be tested for asparagine dependence in any suitable in vitro or in vivo assay, e.g., an in vitro assay wherein the growth medium lacks asparagine.

Diseases or disorders that the recombinant L-asparaginase of the present disclosure is useful in treating include sarcoma, breast cancer, metastatic breast cancer, liver cancer, stomach cancer, colorectal cancer, and head and neck cancer.

B. Methods for Testing for Asparagine Dependence

Cells suspected of causing disease can be tested for asparagine dependence in any suitable in vitro or in vivo assay, e.g., an in vitro assay wherein the growth medium lacks asparagine. Thus, in some embodiments, the present disclosure is directed to a method of treating a disease treatable in a patient, the method comprising administering to the patient an effective amount of a recombinant L-asparaginase of the invention. In a specific embodiment, the disease is ALL. In a specific embodiment, the disease is LBL. In a particular embodiment, the recombinant L-asparaginase used in the treatment of a disease treatable by asparagine depletion comprises the sequence of SEQ ID NO:1. In a further embodiment, the recombinant L-asparaginase is not conjugated to a polymer such as PEG.

C. Methods for Assessing Nadir Serum Asparaginase Activity (NSAA)

Assays for measuring nadir serum asparaginase activity (NSAA) in human subjects may be conducted for evaluation of the human subject. In some embodiments, a serum sample is taken from the human subject to assess NSAA. In some embodiments, a whole blood sample is taken from the subject in order to assess NSAA. In some embodiments, assessing NSAA occurs before the patient is given recombinant L-asparaginase. In some embodiments, assessing NSAA occurs after the patient is given recombinant L-asparaginase.

D. Line of Therapy

A first line therapy is the first treatment given for a disease. A first line therapy may be a monotherapy or a standard set of treatments.

A second line therapy may be a monotherapy or a standard set of treatments. A second line therapy is a treatment given after a first treatment fails, loses its effect (either partially or totally), has side effects that are not tolerated, the patient elects to withdraw from the first treatment for any reason, or a new treatment becomes available that may have a better outcome than the present treatment. In some embodiments, the second line therapy may be given to the human subject in addition to the first line therapy for beneficial additive or synergistic results.

Additional lines of therapy including third, fourth, fifth, sixth, and any further lines of therapies are defined similarly to second line therapies but in this case both the first and the second line therapies either fail, lose their effect (either partially or totally), have side effects that are not tolerated, the patient elects to withdraw from the first and/or second lines of therapy for any reason, a new treatment becomes available that may have a better outcome than the first and second line treatment, or any combination of these reasons. Additional lines of therapy may be a monotherapy or a standard set of treatments. In some embodiments, the additional lines of therapy may be given to the human subject in addition to the first line and/or second line of therapy for beneficial additive or synergistic results.

In some embodiments, treatment with a recombinant L-asparaginase of the present disclosure will be administered as a first line therapy. In other embodiments, treatment with a recombinant L-asparaginase of the present disclosure will be administered as a second line therapy in patients, particularly patients with ALL and LBL, where objective signs of allergy or hypersensitivity, including "silent inactivation," have developed to other asparaginase preparations, in particular, the native *Escherichia-coli*-derived L-asparaginase or its PEGylated variant (pegaspargase). Non-limiting examples of objective signs of allergy or hypersensitivity include testing "antibody positive" for an asparaginase enzyme. The patient may have had a previous hypersensitivity to at least one L-asparaginase from *E. coli*, and/or may have had a previous hypersensitivity to at least one L-asparaginase from *Erwinia chrysanthemi*. The hypersensitivity may be selected from the group consisting of allergic reaction, anaphylactic shock, and silent inactivation. In a specific embodiment, the recombinant L-asparaginase of the present disclosure is used in second line therapy after treatment with pegaspargase. In a more specific embodiment, the recombinant L-asparaginase of the present disclosure used in second line therapy comprises an L-asparaginase produced in a Pseudomonadales flourescens cell, more specifically, comprising a tetramer, wherein each monomer or subunit comprises the sequence of SEQ ID NO:1.

In some embodiments, recombinant L-asparaginase of the present disclosure is used in second line therapy with patients who are hypersensitive to an *E. coli*-derived L-asparaginase, and/or may have had a previous hypersensitivity to an *Erwinia chrysanthemi*-derived L-asparaginase. In some embodiments, the recombinant L-asparaginase may be used as a second line therapy with patients receiving a long-acting *E. coli*-derived asparaginase. In some embodiments, six doses of the recombinant L-asparaginase are administered to the patient as a substitute for one dose of the long-acting *E. coli*-derived asparaginase. In some embodiments, the long-acting *E. coli*-derived asparaginase is pegaspargase. In some embodiments, treatment with a recombinant L-asparaginase of the present disclosure is administered as a third line therapy. In some embodiments, treatment with a recombinant L-asparaginase of the present disclosure is administered as a fourth line therapy. In some embodiments, treatment with a recombinant L-asparaginase of the present disclosure is administered as a fifth line therapy. In some embodiments, treatment with a recombinant L-asparaginase of the present disclosure is administered as a sixth line therapy. In some embodiments, treatment with a recombinant L-asparaginase of the present disclosure is administered as a maintenance therapy.

In some embodiments, treatment with a recombinant L-asparaginase of the present disclosure is co-administered with a multi-agent chemotherapeutic regimen. In some embodiments, treatment with a recombinant L-asparaginase of the present disclosure is co-administered with one or more other chemotherapeutic agents as part of a multi-agent chemotherapeutic regimen. In some embodiments, treating patients with a recombinant L-asparaginase of the present disclosure in addition to other agents helps to ensure availability of an asparaginase for patients who have developed hypersensitivity to *E. coli* derived-asparaginase. Examples of agents that may be part of a multi-agent chemotherapeutic regimen with a recombinant L-asparaginase of the present disclosure include, but are not limited to: cytarabine, vincristine, daunorubicin, methotrexate, leuvocorin, doxorubicin, anthracycline, corticosteroids and glucocortiods (including but not limited to prednisone, prednisolone, and/or dexamethasone), cyclophosphamide, 6-mercaptopurine, venetoclax, and etoposide. In some embodiments, the multi-agent chemotherapeutic regimen is the recombinant L-asparaginase and one additional chemotherapeutic agent. In some embodiments, the multi-agent chemotherapeutic regimen is the recombinant L-asparaginase and two or more additional chemotherapeutic agents.

As an example, patients with ALL will be co-administered the recombinant L-asparaginase of the present disclosure along with a multi-agent chemotherapy during 3 chemotherapy phases including induction, consolidation or intensification, and maintenance. In a specific example, the recombinant L-asparaginase of the present disclosure is co-administered with an asparagine synthetase inhibitor (e.g., such as set forth in WO 2007/103290, which is herein incorporated by reference in its entirety). In another specific example, the recombinant L-asparaginase of the present disclosure is not co-administered with an asparagine synthetase inhibitor, but is co-administered with other chemotherapy drugs. In another specific example, the recombinant L-asparaginase of the present disclosure is co-administered with an asparagine sythetase inhibitor and other chemotherapy drugs. The recombinant L-asparaginase of the present disclosure can be co-administered before, after, or simultaneously with other compounds as part of a multi-agent chemotherapy regimen. In a particular embodiment, the recombinant L-asparaginase of the present disclosure comprises a protein recombinantly produced in *Pseudomonas fluorescens*, and more specifically, the recombinant L-asparaginase comprising the sequence of SEQ ID NO:1.

VI. Compositions, Formulations, Routes of Administration, and Dosing

A. Compositions, Formulations and Routes of Administration

The invention also includes a pharmaceutical composition comprising a recombinant L-asparaginase of the present disclosure. The pharmaceutical composition can be administered to a patient using standard techniques. Techniques and formulations generally may be found in Remington's Pharmaceutical Sciences, 22nd edition, Mack Publishing, 2015 (herein incorporated by reference).

Suitable dosage forms, in part, depend upon the use or the route of entry, for example, oral, transdermal, transmucosal, or by injection (parenteral). Such dosage forms should allow the therapeutic agent to reach a target cell or otherwise have the desired therapeutic effect. For example, pharmaceutical compositions injected into the blood stream preferably are soluble. The pharmaceutical compositions according to the present disclosure can be formulated as pharmaceutically acceptable salts and complexes thereof. Pharmaceutically acceptable salts are non-toxic salts present in the amounts and concentrations at which they are administered. The preparation of such salts can facilitate pharmaceutical use by altering the physical characteristics of the compound without preventing it from exerting its physiological effect. Useful alterations in physical properties include lowering the melting point to facilitate transmucosal administration and increasing solubility to facilitate administering higher concentrations of the drug. The pharmaceutically acceptable salt of a modified protein as described herein may be present as a complex, as those in the art will appreciate. Pharmaceutically acceptable salts include acid addition salts such as those containing sulfate, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate, and quinate. Pharmaceutically acceptable salts can be obtained from acids, including hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid. Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see Remington's Pharmaceutical Sciences, supra. Such salts can be prepared using the appropriate corresponding bases. Pharmaceutically acceptable carriers and/or excipients can also be incorporated into a pharmaceutical composition according to the invention to facilitate administration of the particular asparaginase. Examples of carriers suitable for use in the practice of the invention include calcium carbonate, calcium phosphate, various sugars such as lactose, glucose, or sucrose, or types of starch, cellulose derivatives, gelatin, vegetable oils, polyethylene glycols, and physiologically compatible solvents. Examples of physiologically compatible solvents include sterile solutions of water for injection (WFI), saline solution and dextrose. Pharmaceutical compositions according to the invention can be administered by different routes, including intravenous, intraperitoneal, subcutaneous, intramuscular, oral, topical (transdermal), or transmucosal administration. For oral administration, for example, the compounds can be formulated into conventional oral dosage forms such as capsules, tablets, and liquid preparations such as syrups, elixirs, and concentrated drops. Alternatively, injection (parenteral administration) may be used, e.g., intramuscular, intravenous, intraperitoneal, and subcutaneous injection. For injection, pharmaceutical compositions are formulated in liquid solutions, preferably in physiologically compatible buffers or solutions, such as saline solution, Hank's solution, or Ringer's solution. In addition, the compounds may be formulated in solid form and redissolved or suspended immediately prior to use. For example, lyophilized forms of the recombinant L-asparaginase can be produced. In a specific aspect, the recombinant L-asparaginase is administered intramuscularly. In preferred specific aspect, the recombinant L-asparaginase is administered intravenously.

In a preferred embodiment, the pharmaceutical composition is not lyophilized. In a further embodiment, the pharmaceutical composition is in solution. In some embodiments, a final lyophilization step may cause induced stress and promote degradation of the compound. In some embodiments, lyophilization may increase aggregation. In some further preferred embodiments, the recombinant crisantaspase is administered intramuscularly. In some further preferred embodiments, the recombinant crisantaspase is administered intravenously. For each of these preferred embodiments of forms of administration, it will be appreciated that any form of the recombinant L-asparaginase may be administered, including modified and non-modified forms.

Systemic administration can also be accomplished by transmucosal or transdermal means. For transmucosal or transdermal administration, penetrants appropriate to the barrier to be permeated are used in the formulation. Such penetrants are well known in the art, and include, for example, for transmucosal administration, bile salts, and fusidic acid derivatives. In addition, detergents may be used to facilitate permeation. Transmucosal administration, for example, may be through nasal sprays, inhalers (for pulmonary delivery), rectal suppositories, or vaginal suppositories. For topical administration, compounds can be formulated into ointments, salves, gels, or creams, as is well known in the art.

B. Dosing

In some embodiments, a dose is an amount administered to the human subject over a certain time and frequency. In some embodiments, the dose of recombinant L-asparaginase will be given to a human subject with hypersensitivity only when the hypersensitivity subsides.

In an exemplary embodiment, a recombinant L-asparaginase is administered to a human subject in an amount from about 10 mg/m$^2$ to 100 mg/m$^2$.

In an exemplary embodiment, a recombinant L-asparaginase is administered intramuscularly every other day over a period of 5 consecutive days followed by a rest period of 2 consecutive days, wherein the amount is about 25 mg/m$^2$.

In an exemplary embodiment, a recombinant L-asparaginase is administered intravenously every other day over a period of 5 consecutive days followed by a rest period of 2 consecutive days, wherein the amount is about 37.5 mg/m$^2$.

In further exemplary embodiments and in accordance with any of the discussion herein regarding dosing, the recombinant L-asparaginase administered in such doses is not conjugated to a polymer such as a PEG moiety and/or is not conjugated to a peptide comprising solely alanine and/or proline residues.

1. Dose Amount

The amounts of the recombinant L-asparaginase of the present disclosure that are to be delivered will depend on many factors, for example, the IC50, EC50, the biological half-life of the compound, the age, size, weight, and physical condition of the patient, and the disease or disorder to be treated. The importance of these and other factors to be considered are well known to those of ordinary skill in the art. Generally, the amount of the recombinant L-asparaginase of the present disclosure will be administered at a range from about 1 milligram per square meter of the surface area of the patient's body (mg/m$^2$) to 1,000/m$^2$, with a dosage range of about 10 mg/m$^2$ to about 100 mg/m$^2$ to treat disease, including but not limited to ALL or LBL. Of course, other dosages and/or treatment regimens may be employed, as determined by the attending physician.

In some embodiments, the method comprises administering the recombinant L-asparaginase of the present disclosure at an amount from about 10 mg/m$^2$ and about 100 mg/m$^2$. In some embodiments, the method comprises administering the recombinant L-asparaginase of the present disclosure at an amount from 10 mg/m$^2$ and 100 mg/m$^2$. In some embodiments, the recombinant L-asparaginase of the present disclosure is administered in an amount of about 10, 15, 20, 25, 30, 35, 40, 45, 50, 55, 60, 65, 70, 75, 80, 85, 95, or 95 mg/m$^2$ or an equivalent amount thereof (for example on a protein content basis). In a more specific embodiment, the recombinant L-asparaginase of the present disclosure is administered at an amount selected from the group consisting of about 10, 20, 30, 40, 50, 60, 70, 80, 90, and about 100 mg/m². In another specific embodiment, the recombinant L-asparaginase of the present disclosure is administered at a dose more than or equal to about 1, 10, 15, 20, 25, 30, 35, 40, 45, 50, 55, 60, 65, 70, 75, 80, 85, 95, 95, 100, 200, or 300 mg/m². In another specific embodiment, the recombinant L-asparaginase of the present disclosure is administered at a dose less than or equal to about 300, 200 100, 95, 80, 75, 70, 65, 60, 55, 50, 45, 40, 35, 30, 25, 20, 15, 10, 5, or 1 mg/m². In an exemplary embodiment, the recombinant L-asparaginase of the present disclosure is administered in an amount between about 12 mg/m² and about 90 mg/m². In another exemplary embodiment, the recombinant L-asparaginase of the present disclosure is administered in an amount between about 20 mg/m² and about 80 mg/m². In another exemplary embodiment, the recombinant L-asparaginase of the present disclosure is administered in an amount between about 25 mg/m² and about 70 mg/m². In an exemplary embodiment, the recombinant L-asparaginase of the present disclosure is administered in an amount between about 25 mg/m² and about 80 mg/m². In an exemplary embodiment, the recombinant L-asparaginase of the present disclosure is administered in an amount between about 37.5 mg/m² and about 80 mg/m². In an exemplary embodiment, the recombinant L-asparaginase of the present disclosure is administered in an amount between about 37.5 mg/m² and about 65 mg/m². In an exemplary embodiment, the recombinant L-asparaginase of the present disclosure is administered in an amount between about 25 mg/m² and about 37.5 mg/m². In an exemplary embodiment, the recombinant L-asparaginase of the present disclosure is administered in an amount between about 25 mg/m² and about 100 mg/m². In an exemplary embodiment, the recombinant L-asparaginase of the present disclosure is administered in an amount between about 25 mg/m² and about 65 mg/m². In an exemplary embodiment, the recombinant L-asparaginase of the present disclosure is administered in an amount between about 25 mg/m² and about 80 mg/m².

In an exemplary embodiment, the recombinant L-asparaginase of the present disclosure is administered in an amount between about 30 mg/m² and about 75 mg/m². In an exemplary embodiment, the recombinant L-asparaginase of the present disclosure is administered in an amount between about 35 mg/m² and about 70 mg/m². In an exemplary embodiment, the recombinant L-asparaginase of the present disclosure is administered in an amount between about 40 mg/m² and about 65 mg/m². In an exemplary embodiment, the recombinant L-asparaginase of the present disclosure is administered in an amount between about 45 mg/m² and about 60 mg/m². In an exemplary embodiment, the recombinant L-asparaginase of the present disclosure is administered in an amount between about 50 mg/m² and about 55 mg/m².

In an exemplary embodiment, the recombinant L-asparaginase of the present disclosure is administered in an amount between about 40 mg/m² and about 75 mg/m². In an exemplary embodiment, the recombinant L-asparaginase of the present disclosure is administered in an amount between about 45 mg/m² and about 70 mg/m². In an exemplary embodiment, the recombinant L-asparaginase of the present disclosure is administered in an amount between about 50 mg/m² and about 65 mg/m². In an exemplary embodiment, the recombinant L-asparaginase of the present disclosure is administered in an amount between about 55 mg/m² and about 60 mg/m².

In an exemplary embodiment, the recombinant L-asparaginase of the present disclosure is administered in an amount between about 40 mg/m² and about 60 mg/m². In an exemplary embodiment, the recombinant L-asparaginase of the present disclosure is administered in an amount between about 45 mg/m² and about 55 mg/m². In an exemplary embodiment, the recombinant L-asparaginase of the present disclosure is administered in an amount between about 47.5 mg/m² and about 50 mg/m².

In an exemplary embodiment, the recombinant L-asparaginase of the present disclosure is administered in an amount between about 30 mg/m² and about 35 mg/m².

In an exemplary embodiment, the recombinant L-asparaginase of the present disclosure is administered in an amount between about 30 mg/m² and about 95 mg/m². In an exemplary embodiment, the recombinant L-asparaginase of the present disclosure is administered in an amount between about 35 mg/m² and about 90 mg/m². In an exemplary embodiment, the recombinant L-asparaginase of the present disclosure is administered in an amount between about 40 mg/m² and about 85 mg/m². In an exemplary embodiment, the recombinant L-asparaginase of the present disclosure is administered in an amount between about 45 mg/m² and about 80 mg/m². In an exemplary embodiment, the recombinant L-asparaginase of the present disclosure is administered in an amount between about 50 mg/m² and about 75 mg/m². In an exemplary embodiment, the recombinant L-asparaginase of the present disclosure is administered in an amount between about 55 mg/m² and about 70 mg/m². In an exemplary embodiment, the recombinant L-asparaginase of the present disclosure is administered in an amount between about 60 mg/m² and about 65 mg/m².

In an exemplary embodiment, the recombinant L-asparaginase of the present disclosure is administered in an amount between about 30 mg/m² and about 60 mg/m². In an exemplary embodiment, the recombinant L-asparaginase of the present disclosure is administered in an amount between about 35 mg/m² and about 55 mg/m². In an exemplary embodiment, the recombinant L-asparaginase of the present disclosure is administered in an amount between about 40 mg/m² and about 50 mg/m². In an exemplary embodiment, the recombinant L-asparaginase of the present disclosure is administered in an amount between about 42.5 mg/m² and about 57.5 mg/m².

In an exemplary embodiment, the recombinant L-asparaginase of the present disclosure is administered in an amount between about 30 mg/m² and about 75 mg/m². In an exemplary embodiment, the recombinant L-asparaginase of the present disclosure is administered in an amount between about 35 mg/m² and about 70 mg/m². In an exemplary embodiment, the recombinant L-asparaginase of the present disclosure is administered in an amount between about 40 mg/m² and about 65 mg/m². In an exemplary embodiment, the recombinant L-asparaginase of the present disclosure is administered in an amount between about 45 mg/m² and about 60 mg/m². In an exemplary embodiment, the recombinant L-asparaginase of the present disclosure is administered in an amount between about 50 mg/m² and about 55 mg/m².

In some embodiments, the recombinant L-asparaginase of the present disclosure is administered intramuscularly in an amount of between about 10 mg/m² and about 50 mg/m². In some embodiments, the recombinant L-asparaginase of the present disclosure is administered intramuscularly in an amount of between about 12.5 mg/m² and about 47.5 mg/m². In some embodiments, the recombinant L-asparaginase of the present disclosure is administered intramuscularly in an amount of between about 15 mg/m² and about 45 mg/m². In some embodiments, the recombinant L-asparaginase of the present disclosure is administered intramuscularly in an amount of between about 20 mg/m² and about 42.5 mg/m². In some embodiments, the recombinant L-asparaginase of the present disclosure is administered intramuscularly in an amount of between about 22.5 mg/m² and about 40 mg/m². In some embodiments, the recombinant L-asparaginase of the present disclosure is administered intramuscularly in an amount of between about 24 mg/m² and about 39 mg/m². In some embodiments, the recombinant L-asparaginase of the present disclosure is administered intramuscularly in an amount of between about 27 mg/m² and about 37.5 mg/m². In some embodiments, the recombinant L-asparaginase of the present disclosure is administered intramuscularly in an amount of between about 30 mg/m² and about 45 mg/m². In some embodiments, the recombinant L-asparaginase of the present disclosure is administered intramuscularly in an amount of about 25 mg/m². In some embodiments, the recombinant L-asparaginase of the present disclosure is administered intramuscularly in an amount of 25 mg/m². In an exemplary embodiment, the recombinant L-asparaginase of the present disclosure is administered intramuscularly in an amount between about 25 mg/m² and about 80 mg/m². In an exemplary embodiment, the recombinant L-asparaginase of the present disclosure is administered intramuscularly in an amount between about 37.5 mg/m² and about 80 mg/m². In an exemplary embodiment, the recombinant L-asparaginase of the present disclosure is administered intramuscularly in an amount between about 37.5 mg/m² and about 65 mg/m². In an exemplary embodiment, the recombinant L-asparaginase of the present disclosure is administered intramuscularly in an amount between about 25 mg/m² and about 37.5 mg/m². In an exemplary embodiment, the recombinant L-asparaginase of the present disclosure is administered intramuscularly in an amount between about 30 mg/m² and about 75 mg/m². In an exemplary embodiment, the recombinant L-asparaginase of the present disclosure is administered intramuscularly in an amount between about 35 mg/m² and about 70 mg/m². In an exemplary embodiment, the recombinant L-asparaginase of the present disclosure is administered intramuscularly in an amount between about 40 mg/m² and about 65 mg/m². In an exemplary embodiment, the recombinant L-asparaginase of the present disclosure is administered intramuscularly in an amount between about 45 mg/m² and about 60 mg/m². In an exemplary embodiment, the recombinant L-asparaginase of the present disclosure is administered intramuscularly in an amount between about 50 mg/m² and about 55 mg/m². In an exemplary embodiment, the recombinant L-asparaginase of the present disclosure is administered intramuscularly in an amount between about 40 mg/m² and about 75 mg/m². In an exemplary embodiment, the recombinant L-asparaginase of the present disclosure is administered intramuscularly in an amount between about 45 mg/m² and about 70 mg/m². In an exemplary embodiment, the recombinant L-asparaginase of the present disclosure is administered intramuscularly in an amount between about 50 mg/m² and about 65 mg/m². In an exemplary embodiment, the recombinant L-asparaginase of the present disclosure is administered intramuscularly in an amount between about 55 mg/m² and about 60 mg/m². In an exemplary embodiment, the recombinant L-asparaginase of the present disclosure is administered intramuscularly in an amount between about 40 mg/m² and about 60 mg/m². In an exemplary embodiment, the recombinant L-asparaginase of the present disclosure is administered intramuscularly in an amount between about 45 mg/m² and about 55 mg/m². In an exemplary embodiment, the recombinant L-asparaginase of the present disclosure is administered intramuscularly in an amount between about 47.5 mg/m² and about 50 mg/m². In an exemplary embodiment, the recombinant L-asparaginase of the present disclosure is administered intramuscularly in an amount between about 30 mg/m² and about 35 mg/m².

In some embodiments, the recombinant L-asparaginase of the present disclosure is administered intravenously in an amount of between about 10 mg/m² and about 95 mg/m². In some embodiments, the recombinant L-asparaginase of the present disclosure is administered intravenously in an amount of between about 20 mg/m² and about 60 mg/m². In some embodiments, the recombinant L-asparaginase of the present disclosure is administered intravenously in an amount of between about 22.5 mg/m² and about 57.5 mg/m². In some embodiments, the recombinant L-asparaginase of the present disclosure is administered intravenously in an amount of between about 25 mg/m² and about 55 mg/m². In some embodiments, the recombinant L-asparaginase of the present disclosure is administered intravenously in an amount of between about 27.5 mg/m² and about 47.5 mg/m². In some embodiments, the recombinant L-asparaginase of the present disclosure is administered intravenously in an amount of between about 30 mg/m² and about 45 mg/m². In some embodiments, the recombinant L-asparaginase of the present disclosure is administered intravenously in an amount of between about 32.5 mg/m² and about 42.5 mg/m². In some embodiments, the recombinant L-asparaginase of the present disclosure is administered intravenously in an amount of between about 21.5 mg/m² and about 38.5 mg/m². In some embodiments, the recombinant L-asparaginase of the present disclosure is administered intravenously in an amount of between about 36 mg/m² and about 45 mg/m². In some embodiments, the recombinant L-asparaginase of the present disclosure is administered intravenously in an amount of about 37.5 mg/m². In some embodiments, the recombinant L-asparaginase of the present disclosure is administered intravenously in an amount of 37.5 mg/m².

In an exemplary embodiment, the recombinant L-asparaginase of the present disclosure is administered intravenously in an amount between about 25 mg/m² and about 37.5 mg/m². In an exemplary embodiment, the recombinant L-asparaginase of the present disclosure is administered intravenously in an amount between about 25 mg/m² and about 100 mg/m². In an exemplary embodiment, the recombinant L-asparaginase of the present disclosure is administered intravenously in an amount between about 25 mg/m² and about 65 mg/m². In an exemplary embodiment, the recombinant L-asparaginase of the present disclosure is administered intravenously in an amount between about 25 mg/m² and about 80 mg/m². In an exemplary embodiment, the recombinant L-asparaginase of the present disclosure is administered intravenously in an amount between about 30 mg/m² and about 35 mg/m². In an exemplary embodiment, the recombinant L-asparaginase of the present disclosure is administered intravenously in an amount between about 30 mg/m² and about 95 mg/m². In an exemplary embodiment, the recombinant L-asparaginase of the present disclosure is administered intravenously in an amount between about 35 mg/m² and about 90 mg/m². In an exemplary embodiment, the recombinant L-asparaginase of the present disclosure is administered intravenously in an amount between about 40 mg/m² and about 85 mg/m². In an exemplary embodiment, the recombinant L-asparaginase of the present disclosure is administered intravenously in an amount between about 45 mg/m² and about 80 mg/m². In an exemplary embodiment, the recombinant L-asparaginase of the present disclosure is administered intravenously in an amount between about 50 mg/m$^2$ and about 75 mg/m$^2$. In an exemplary embodiment, the recombinant L-asparaginase of the present disclosure is administered intravenously in an amount between about 55 mg/m$^2$ and about 70 mg/m$^2$. In an exemplary embodiment, the recombinant L-asparaginase of the present disclosure is administered intravenously in an amount between about 60 mg/m$^2$ and about 65 mg/m$^2$. In an exemplary embodiment, the recombinant L-asparaginase of the present disclosure is administered intravenously in an amount between about 30 mg/m$^2$ and about 60 mg/m$^2$. In an exemplary embodiment, the recombinant L-asparaginase of the present disclosure is administered intravenously in an amount between about 35 mg/m$^2$ and about 55 mg/m$^2$. In an exemplary embodiment, the recombinant L-asparaginase of the present disclosure is administered intravenously in an amount between about 40 mg/m$^2$ and about 50 mg/m$^2$. In an exemplary embodiment, the recombinant L-asparaginase of the present disclosure is administered intravenously in an amount between about 42.5 mg/m$^2$ and about 57.5 mg/m$^2$. In an exemplary embodiment, the recombinant L-asparaginase of the present disclosure is administered intravenously in an amount between about 30 mg/m$^2$ and about 75 mg/m$^2$. In an exemplary embodiment, the recombinant L-asparaginase of the present disclosure is administered intravenously in an amount between about 35 mg/m$^2$ and about 70 mg/m$^2$. In an exemplary embodiment, the recombinant L-asparaginase of the present disclosure is administered intravenously in an amount between about 40 mg/m$^2$ and about 65 mg/m$^2$. In an exemplary embodiment, the recombinant L-asparaginase of the present disclosure is administered intravenously in an amount between about 45 mg/m$^2$ and about 60 mg/m$^2$. In an exemplary embodiment, the recombinant L-asparaginase of the present disclosure is administered intravenously in an amount between about 50 mg/m$^2$ and about 55 mg/m$^2$.

In another embodiment, the method comprises administering a recombinant L-asparaginase of the present disclosure that elicits a lower immunogenic response in a patient compared to a non-recombinant L-asparaginase.

2. Dose Frequency

In a specific embodiment, treatment will be administered at a dose ranging from about 1 mg/m$^2$ to about 1000 mg/m$^2$, typically about 10 mg/m$^2$ to about 100 mg/m$^2$, at a schedule ranging from about three a week to about once a month, typically once per week or once every other week, as a single agent (e.g., monotherapy) or as part of a combination of chemotherapy drugs, including, but not limited to glucocorticoids, corticosteroids, anticancer compounds or other agents, including, but not limited to methotrexate, dexamethasone, prednisone, prednisolone, vincristine, cyclophosphamide, and anthracycline.

The recombinant L-asparaginase of the present disclosure can be administered before, after, or simultaneously with other compounds as part of a multi-agent chemotherapy regimen. In a particular embodiment, the recombinant L-asparaginase of the present disclosure comprises a protein recombinantly produced in *Pseudomonas fluorescens*, and more specifically, the recombinant L-asparaginase comprises a sequence according to SEQ ID NO: 1. In some embodiments, the recombinant L-asparaginase of the present disclosure is administered at a dose that depletes L-asparagine to undetectable levels using methods and apparatus known in the art for a period of about 3 days to about 10 days (e.g., 3, 4, 5, 6, 7, 8, 9, or 10 days) for a single dose.

In some embodiments, the recombinant L-asparaginase of the present disclosure is administered three times a week. In some embodiments, the recombinant L-asparaginase of the present disclosure is administered every other day over a period of 5 consecutive days followed by a rest period of 2 consecutive days. In some embodiments, the recombinant L-asparaginase of the present disclosure is administered on Monday, Wednesday, and Friday of the same week.

In some embodiments, the recombinant L-asparaginase of the present disclosure is administered three times a week for at least one to three weeks. In some embodiments, the recombinant L-asparaginase of the present disclosure is administered every other day over a period of 5 consecutive days followed by a rest period of 2 consecutive days for about one to three weeks. In some embodiments, the recombinant L-asparaginase of the present disclosure is administered on Monday, Wednesday, and Friday of the week for about one to three weeks.

In some embodiments, the recombinant L-asparaginase of the present disclosure is administered three times a week for about two weeks. In some embodiments, the recombinant L-asparaginase of the present disclosure is administered every other day over a period of 5 consecutive days followed by a rest period of 2 consecutive days for about two weeks. In some embodiments, the recombinant L-asparaginase of the present disclosure is administered on Monday, Wednesday, and Friday of the same week for about two weeks.

In some embodiments, the recombinant L-asparaginase of the present disclosure is administered three times a week for two weeks. In some embodiments, the recombinant L-asparaginase of the present disclosure is administered every other day over a period of 5 consecutive days followed by a rest period of 2 consecutive days for two weeks. In some embodiments, the recombinant L-asparaginase of the present disclosure is administered on Monday, Wednesday, and Friday of the same week for two weeks.

In some embodiments, the recombinant L-asparaginase of the present disclosure is administered three times a week, continuing until the patient no longer has a disease that is treatable by depletion of asparagine. In some embodiments, the recombinant L-asparaginase of the present disclosure is administered every other day over a period of 5 consecutive days followed by a rest period of 2 consecutive days, continuing until the patient no longer has a disease that is treatable by depletion of asparagine. In some embodiments, the recombinant L-asparaginase of the present disclosure is administered on Monday, Wednesday, and Friday of the same week, continuing until the patient no longer has a disease that is treatable by depletion of asparagine.

In some embodiments, the recombinant L-asparaginase of the present disclosure is administered three times a week, continuing until the patient decides to end or postpone treatment. In some embodiments, the recombinant L-asparaginase of the present disclosure is administered every other day over a period of 5 consecutive days followed by a rest period of 2 consecutive days, continuing until the patient decides to end or postpone treatment. In some embodiments, the recombinant L-asparaginase of the present disclosure is administered on Monday, Wednesday, and Friday of the same week, continuing until the patient decides to end or postpone treatment.

In some embodiments, the recombinant L-asparaginase of the present disclosure is administered about every 48 hours. In some embodiments, the recombinant L-asparaginase of the present disclosure is administered about every 72 hours.

In some embodiments, recombinant L-asparaginase of the present disclosure is administered as a second line therapy with patients who are hypersensitive to an *E. coli*-derived L-asparaginase, and/or may have had a previous hypersensitivity to an *Erwinia chrysanthemi*-derived L-asparaginase.

In some embodiments, the recombinant L-asparaginase is administered to the human subject as a substitute for a dose of a long-acting E. coli-derived asparaginase. In some embodiments, six doses of recombinant L-asparaginase are administered to the human subject as a substitute for one dose of the long-acting E. coli-derived asparaginase. In some embodiments, the long-acting E. coli-derived asparaginase is pegaspargase. In a further embodiment, the six separate doses may occur over a period of about two weeks.

In some embodiments, a dose regimen for the recombinant L-asparaginase comprises a cycle, wherein the cycle comprises a first dose, a second dose, and a third dose, wherein the cycle is optionally repeatable, and wherein the first dose, second dose, and third dose are administered about 48-72 hours apart.

In some embodiments, dose amounts may vary within the cycle.

In some embodiments, a dose regimen for the recombinant L-asparaginase comprises a cycle, wherein the cycle is optionally repeatable, and wherein the cycle comprises administration of the recombinant L-asparaginase every other day over a period of five consecutive days followed by a rest period of two consecutive days, wherein the first dose of the cycle is 25 mg/m$^2$, the second dose of the cycle is 25 mg/m$^2$ and the third dose of the cycle is 37.5 mg/m$^2$, followed by the rest period of two consecutive days.

In some embodiments, a dose regimen for the recombinant L-asparaginase comprises a cycle, wherein the cycle is optionally repeatable, and wherein the cycle comprises administration of the recombinant L-asparaginase every other day over a period of five consecutive days followed by a rest period of two consecutive days, wherein the first dose of the cycle is 37.5 mg/m$^2$, the second dose of the cycle is 37.5 mg/m$^2$ and the third dose of the cycle is 37.5 mg/m$^2$, followed by the rest period of two consecutive days.

In some embodiments, a dose regimen for the recombinant L-asparaginase comprises a cycle, wherein the cycle is optionally repeatable, and wherein the cycle comprises administration of the recombinant L-asparaginase every other day over a period of five consecutive days followed by a rest period of two consecutive days, wherein the first dose of the cycle is 37.5 mg/m$^2$, the second dose of the cycle is 25 mg/m$^2$ and the third dose of the cycle is 37.5 in mg/m$^2$, followed by the rest period of two consecutive days.

In some embodiments, a dose regimen for the recombinant L-asparaginase comprises a cycle, wherein the cycle is optionally repeatable, and wherein the cycle comprises administration of the recombinant L-asparaginase every other day over a period of five consecutive days followed by a rest period of two consecutive days, wherein the first dose of the cycle is 37.5 mg/m$^2$, the second dose of the cycle is 25 mg/m$^2$ and the third dose of the cycle is 25 mg/m$^2$, followed by the rest period of two consecutive days. In some embodiments, the first dose of the cycle is administered on a Monday, the second dose of the cycle is given on a Wednesday, and the third dose of the cycle is given on a Friday.

The dose regimen may encompass any number of cycles for any number of weeks or until any endpoint that is specified herein.

3. Dose Time

In some embodiments, the dose time to the human subject has a short duration, for example, immediate or from one second to five minutes when delivered by intramuscular injection. In other embodiments, the dose time to the human subject is of longer duration, for example when delivered by intravenous injection, In some embodiments, the dose of recombinant L-asparaginase lasts between about 5 minutes and about 4 hours. In an exemplary embodiment, the dose time to the human subject lasts between 90 minutes and about 150 minutes. In some embodiments, the dose time to the human subject lasts about two hours. In some embodiments, the dose time to the human subject lasts two hours. In some embodiments, the dose time to the human subject lasts between about 45 minutes and about 75 minutes. In some embodiments, the dose time to the human subject lasts about one hour. In some embodiments, the dose time to the human subject lasts one hour.

EXAMPLES

Example 1: Study to Evaluate Toxicity and Toxicokinetics

The toxicity and toxicokinetics (TK) of recombinant L-asparaginase was investigated in a good laboratory practices (GLP) 2-week daily intravenous infusion study in rats. A 2-week recovery phase was also included to assess the reversibility or persistence of the effects, and/or the occurrence of delayed toxicities. Considering that recombinant L-asparaginase is a biotechnology-derived product, the development of anti-drug antibodies (ADAs) was prospectively evaluated in all main study animals to aid in the interpretation of the study outcomes.

Four groups of male and female Crl:CD (SD) rats (n=10/sex/group) were administered doses of 0, 4.6, 15.2, and 45.6 mg/kg recombinant L-asparaginase respectively. Recovery animals were included in the control and high dose groups (n=5/sex/group). Toxicokinetic animals (n=3/sex for control group, and n=9/sex/dose groups) were also included. Animals received recombinant L-asparaginase via 2-hour intravenous infusion (+10 minutes) by means of a catheter implanted in a femoral vein at a dose rate of 5 mL/kg/hour. The vehicle and control article was 20 mM sodium phosphate, 50 mM sodium chloride, and 6.4% Trehalose, with a pH of 7.0.

A sentinel group was also dosed with the highest dose prior to initiation of the main study and observed for 2 days, and sacrificed on Day 3, without necropsy.

Mortality, clinical observations, body weights, body weight change, food consumption, ophthalmic observations, and clinical and anatomic pathology were documented along with toxicokinetics (as assessed via serum asparaginase activity (SAA)) and anti-drug antibody analysis.

Toxicity and toxicokinetic animals in groups 1 (control) through 3 (15.2 mg/kg) were dosed for 14 days and survived to their scheduled necropsy. Dosing in group 4 (45.6 mg/kg) was halted on Day 6 due to adverse clinical observations at which time animals were either necropsied or put on a 2-week recovery according to their assigned group. Recovery animals in group 1 were administered the vehicle once daily for 14 days, followed by 6 days of recovery, and were thus sacrificed on the same calendar day as the recovery animals in group 4.

Exposure, as assessed by SAA Cmax and AUC0-24, increased with the increase in dose level from 4.6 to 45.6 mg/kg/day on Day 1 and from 4.6 to 15.2 mg/kg/day on Day 14. The increases in Cmax and AUC0-24 values were approximately dose proportional from 4.6 to 15.2 and 15.2 to 45.6 mg/kg/day on Day 1 and from 4.6 to 15.2 mg/kg/day on Day 14, while from 4.6 to 45.6 mg/kg/day on Day 1, AUC0-24 increased 18-fold with a 10-fold increase in dose.

There are no significant sex differences in SAA Cmax and AUC0-24 values. No accumulation of SAA was observed after multiple doses in rats.

In animals from the high dose group euthanized prematurely, clinical observations included piloerection, rough haircoat, red skin of the feet, and clear oral discharge. Significant hematology changes indicative of decreased hematopoiesis were noted and included decreased reticulocyte, platelet, and leukocyte counts. These changes were found to be reversible in the recovery animals. Increased blood glucose and urea nitrogen concentrations, as well as decreased protein and liver enzymes were suggestive of dehydration, prerenal azotemia, protein loss or compartmental shift and hepatic downregulation of enzymatic activity, respectively. Macroscopic observations were limited to focal red discoloration of the mucosa in the glandular stomach of one female that lacked microscopic correlate. Microscopic findings included decreased cellularity in the marrow of the femur, myocardial necrosis and hemorrhage, submucosal edema/abscess and epithelial hyperplasia/erosion in the nonglandular stomach/duodenum, decreased red pulp, extramedullary hematopoiesis, and lymphocytes in the spleen, decreased cortical lymphocytes in the thymus and secretory depletion in the pancreas. These changes were considered adverse. Increases in spleen and thymus weights in males and females were noted at the recovery sacrifice but considered consistent with recovery. Microscopic evaluation was not conducted on recovery animals.

Dose-related decrease in food consumption and body weights were noted in animals administered ≤15.2 mg/kg/day and piloerection was noted at 15.2 mg/kg/day. Dose-related hematology and clinical chemistry changes generally consistent with those observed in the high-dose group, but of lesser magnitude were observed in most animals. These clinical pathology changes were considered not adverse. Microscopic findings in low- and mid-dose groups animals consisted of minimal to slight decreased erythroid precursors and increased myeloid precursors were consistent with the hematology findings. The decreased spleen weights correlated with decreased extramedullary hematopoiesis and red pulp whereas the decreased thymus weights lacked a microscopic correlate.

In conclusion, male and female Crl:CD (SD) rats received vehicle control article or 4.6, 15.2, or 45.6 mg/kg/day recombinant L-asparaginase via intravenous infusion once daily for 14 days. Adverse clinical observations that required sacrifice in moribund condition and cessation of dosing on Day 6 of the dosing phase, and decreased cellularity of the marrow in the femur, myocardial necrosis and hemorrhage in the heart, submucosal edema or abscess and epithelial hyperplasia in the nonglandular stomach, and erosion/ulcer of the stomach or duodenum occurred in animals administered 45.6 mg/kg/day. Nonadverse clinical observations, clinical pathology changes, and microscopic findings occurred in animals administered ≤15.2 mg/kg/day. Thus, the no observed adverse effect level (NOAEL) is 15.2 mg/kg/day.

The highlights of this study include: Male and female Crl:CD (SD) rats (n=10/sex/gr) with recovery groups (n=5/sex/gr) in controls and high dose. Recombinant L-asparaginase (0, 4.6, 15.2, or 45.6 mg/kg/day) was administered via daily 2 h intravenous infusion for up to 14 days. Adverse clinical observations required sacrifice and cessation of dosing on Day 6 in high dose group. Adverse decreased cellularity of the marrow in the femur, necrosis and hemorrhage in the heart, and erosion, edema, hyperplasia, abscess and/or ulcer in the nonglandular stomach/duodenum occurred in high dose group. Nonadverse but qualitatively similar clinical observations, clinical pathology changes, and microscopic findings occurred in animals administered ≤15.2 mg/kg/day. No observed adverse effect level (NOAEL) was determined to be 15.2 mg/kg/day.

Example 2: Study to Evaluate Safety

Subjects were aged 18 to 55 years and in good general health as determined by the investigator. In Dose Cohort 1, the subjects were randomized (1:1) to receive a single recombinant L-asparaginase dose (25 mg/m$^2$) by either a 2-hour intravenous (IV) infusion (N=6) or an intramuscular (IM) injection (N=6). After the safety, tolerability, and pharmacokinetics of the recombinant L-asparaginase was evaluated to determine the need for another dosing cohort, Dose Cohort 2 randomized subjects (1:1) to receive a single recombinant L-asparaginase dose either 37.5 mg/m$^2$ IV (N=6) or 12.5 mg/m$^2$ IM (N=6). Recombinant L-asparaginase was administered in the inpatient clinical unit; the subjects were discharged on Day 5 with safety follow-up calls on Days 6 and 30. The primary objective was to assess safety and tolerability of recombinant L-asparaginase by IV and IM dosing for each cohort. Secondary objectives included characterization of recombinant L-asparaginase pharmacokinetics by IV and IM administrations based on serum asparaginase activity (SAA).

Among the 24 subjects enrolled, demographic characteristics (mean±SD) included: age (38.4±8.30 years), weight (77.04±10.00 kg), and body surface area (1.91±0.15 m$^2$). Additionally, 63% of the subjects were male, 97% were of Hispanic/Latino ethnicity, 83% were white, and 17% were black/African American. Both safety and pharmacokinetics were evaluated in this study. For safety, 8/12 (67%) subjects had ≥1 adverse event (IV=4 subjects; IM=4 subjects) in Dose Cohort 1. In Dose Cohort 2, 11/12 (92%) subjects had ≥1 adverse event (IV=6 subjects; IM=5 subjects). No serious adverse events or grade ≥3 adverse events were reported for any subject in either dosing cohort. The most common treatment-emergent adverse event occurring in ≥2 subjects in each dosing cohort was nausea (FIG. 1, see Table 1). Dyspepsia was the most common adverse event in subject who received recombinant L-asparaginase 12.5 mg/m$^2$ IM (FIG. 1, see Table 1). Pharmacokinetics assessment showed that when administered IM, recombinant L-asparaginase serum asparaginase activity levels achieved ≥0.1 IU/mL in 6/6 (100%) subjects at 48 and 72 hours post-dose in the 12.5 and 25 mg/m$^2$ dose cohorts. Following IV administration, serum asparaginase activity levels achieved ≥0.1 IU/mL in 6/6 (100%) subjects at 48 hours and 4/6 (67%) subjects at 72 hours post-dose at the 25 mg/m$^2$ dose level, while 6/6 (100%) subjects achieved ≥0.1 IU/mL at 48 and 72 hours post-dose at the 37.5 mg/m$^2$ dose level (FIG. 1, see Table 2).

Recombinant L-asparaginase administration in healthy adults was well tolerated and there were no unanticipated adverse events, no reported serum asparaginase activities, and no grade ≥3 adverse events. Serum asparaginase activity levels ≥0.1 IU/mL, a surrogate marker for asparagine depletion, were achieved in all human subjects receiving IM and IV recombinant L-asparaginase at 48 hours. SAA levels ≥0.1 IU/mL were also achieved by all subjects at 72 hours after recombinant L-asparaginase dosing, except for 2 subjects in the 25 mg/m$^2$ IV group. Based on the totality of pharmacokinetics and safety data from this study, the recommended phase 2/3 starting dose is 25 mg/m$^2$ for the IM route of administration and 37.5 mg/m² for the IV route of administration on a Monday/Wednesday/Friday dosing schedule.

Example 3: Population Pharmacokinetic (PK) Model Development and Simulation

A population PK model was developed for recombinant L-asparaginase using intensive serum asparaginase activity (SAA) data from a phase 1 single-dose study in healthy adult subjects (sbj), and effects of intrinsic covariates (body weight, body surface area, age, sex, and race) on PK parameters were evaluated. This population PK model was developed to inform the starting dose selected for the pivotal phase 2/3 recombinant L-asparaginase study. A total of 24 subjects were included in the model, including intravenous (IV) data at 25 mg/m² [N=6] and 37.5 mg/m² [N=6], and intramuscular (IM) data at 12.5 mg/m² [N=6] and 25 mg/m² [N=6]. The developed model was used to simulate adult and pediatric SAA profiles (1000 sbj/population) to explore the likelihood of achieving a therapeutic target trough SAA level ≥0.1 IU/mL based on different doses, schedules, and routes of administration.

The final model, which describes both IV and IM routes, is a 1-compartment model with linear elimination (IV) and mixed order absorption (IM only), with weight included as an allometric covariate on SAA clearance. Body size metrics, i.e. body weight and BSA (body surface area), were confirmed as statistically significant covariates and accounted for 2.8% and 3.4% variability in recombinant L-asparaginase PK. Based on phase 1 data and population PK modeling and simulations, the recommended starting dose for a phase 2/3 study is 25 mg/m² for IM and 37.5 mg/m² for IV routes of administration on a Monday/Wednesday/Friday dosing schedule. The recommended doses and schedule are anticipated to maintain trough SAA levels ≥0.1 IU/mL at 72 hours postdose.

Example 4: Study to Evaluate Safety and Efficacy

This test is an open-label, multicenter, dose confirmation and pharmacokinetic Phase 2/3 study of recombinant L-asparaginase in patients with Acute Lymphoblastic Leukemia (ALL) or Lymphoblastic Lymphoma (LBL) who are hypersensitive to an *E. coli*-derived asparaginase (allergic reaction or silent inactivation) and have more than one dose of *E. coli*-derived asparaginase remaining in their treatment plan (Table 3). The study is designed to assess the tolerability and efficacy of recombinant L-asparaginase in patients who develop hypersensitivity to an *E. coli*-derived asparaginase, as measured by asparaginase activity. For these patients, 6 doses of recombinant L-asparaginase are substituted for each dose of long-acting *E. coli*-derived asparaginase. Individual patient treatment duration varies depending on the number of *E. coli*-derived asparaginase doses that remain in the patient's original treatment plan.

The study consists of 2 sequential parts: Part A determined the dose of recombinant L-asparaginase for intramuscular (IM) administration and confirmed safety and efficacy; Part B defined the optimal dose and schedule of intravenous (IV) recombinant L-asparaginase.

Part A of the study has 2 IM cohorts. Cohort 1 is a repeat dose/confirmatory cohort, where a final IM dose level will be selected. Cohort 2 is an expansion cohort to confirm the efficacy and safety of the final IM dose level and schedule.

Part B will be conducted to define the optimal dose of the IV administration of recombinant L-asparaginase for further study in ALL/LBL patients as a repeated dose.

Additional courses of recombinant L-asparaginase will be administered based on each patient's original treatment plan for as long as the patient derives clinical benefit.

Blood samples will be collected at prespecified time points to determine serum asparaginase activity levels, and patients were monitored for adverse events. Immunogenicity of recombinant L-asparaginase treatment was also assessed.

The primary objectives are to (1) determine the response rate during the first course of IM recombinant L-asparaginase administration. The response rate is defined as the proportion of patients with the last 72-hour nadir serum asparaginase activity level being ≥0.1 IU/mL during the first course of treatment, and (2) assess the occurrence of treatment-emergent adverse events (TEAE).

Secondary objectives are to determine (1) the proportion of patients with the last 48-hour nadir serum asparaginase activity level ≥0.1 IU/mL during the first course of IM administration of recombinant L-asparaginase, in a time frame of two weeks (2) the proportion of patients with the last 48-hour nadir serum asparaginase activity level ≥0.4 IU/mL during the first course of IM administration of recombinant L-asparaginase in a time frame of two weeks, (3) the proportion of patients with the last 72-hour nadir serum asparaginase level ≥0.4 IU/mL during the first course of IM administration of recombinant L-asparaginase in a time frame of two weeks, (4) characterization of the pharmacokinetics of IM recombinant L-asparaginase based on serum asparaginase activity using a population pharmacokinetics approach and exposure related correlations in a time frame of up to 30 days after the last dose, (5) incidence of anti-drug antibody formation against recombinant L-asparaginase in a time frame up to 30 days after the last dose.

The eligibility criteria allows for both males and females. Inclusion criteria include: (1) pediatric and adult patients with a diagnosis of ALL or LBL, (2) patients that have had an allergic reaction to a long-acting *E. coli*-derived asparaginase OR have silent inactivation, (3) patients have 1 or more courses of *E. coli*-derived asparaginase remaining in his/her treatment plan, (4) patients must have, in the opinion of the investigator, fully recovered from their prior allergic reaction to *E. coli*-derived asparaginase. Exclusion criteria include: (1) patients having previously received *Erwinia chrysanthemi*-derived L-asparaginase or recombinant L-asparaginase, (2) patients having relapsed ALL or LBL, (3) patients who are currently receiving another investigational agent and/or treated with an investigation device at the same time as recombinant L-asparaginase (within 48 hours) during course 1 of recombinant L-asparaginase, (4) patients having a history of ≥Grade 3 pancreatitis, (5) patients having prior history of asparaginase-associated ≥Grade 3 hemorrhagic event or asparaginase-associated thrombus requiring anticoagulation therapy, excluding catheter-related thrombotic events.

Further testing will be with additional subcohorts at higher doses above 37.5 mg/m² with each additional dose level(s) not to exceed a 50% increase from the previous dose level.

This study allows enrollment for an assessment of IV formulation as well as IM formulation; study center participation will be at the discretion of the sponsor.

Undetectable SAA levels may be based on the lower limit of quantification, as defined by a certified laboratory authorized under CLIA to perform this testing. CLIA-certified laboratories utilize different limits of quantification depending on their assay methodologies, and results to determine undetectable SAA levels may vary between laboratories.

Serum asparaginase concentration is the same as PK Content for this study. Alignment between the SAP (which uses serum asparaginase concentration) and the label on the laboratory tubes (which uses PK Content).

The testing window is in certain preferred embodiments is 7 days for all laboratory tests, including coagulation tests and laboratory tests at screening.

Example 5: Study to Evaluate Protein Aggregation

A qualification study was conducted on a small scale recombinant L-asparaginase batch produced at lab scale. The study consisted of analytical comparability with commercial product Erwinase® to ensure that the quality, safety, and potency of the recombinant L-asparaginase was comparable to native L-asparaginase from the natural fermentation of Dickeya chrysanthemi (currently in clinical use) and is not adversely affected by the use of an alternative expression system and purification process.

SEC-HPLC Method: The determination of purity by size exclusion chromatography was performed using SEC-HPLC using a Phenomenex BioSep SEC-s4000 column. The column was conditioned with mobile phase (50 mM phosphate, 200 mM NaCl, pH 7.0) at 1 mL/min for 1 hour before injections. BioRad Gel Filtration Standards were diluted to 1 mg/mL in mobile phase and injected in triplicate after multiple injections of mobile phase blanks to clear the column. The purities of recombinant L-asparaginase, E. coli-derived recombinant crisantaspase, and Erwinase® were evaluated (FIG. 2).

The SEC-HPLC results exhibit a main peak which represents the tetramer as well as an aggregate peak. There are varying levels of HMW aggregation in all samples with higher amounts in Erwinaze CAMR176 (6%) when compared to recombinant L-asparaginase (0.3%).

Size Exclusion Chromatography-Multi-Angle Light Scattering (SEC MALLS) Method: Using C.52.S1640 and the Solvias standard operating procedure, test solutions were prepared in duplicate for all samples. The samples were diluted with formulation buffer to 10 mg/mL and mixed. At least 4 mL were prepared. The sample solution was filtered through a 0.2 µM syringe filter directly into an HPLC vial. The first few drops were discarded. If the protein concentration was below 10 mg/mL, the injection volume needed to be adjusted to be able to inject 750 ug. The following samples and references were analyzed with this technique: all non-stressed batches, all batches stressed due to overnight freeze at <-75° C. and 3 hours thawed room temperature for five and ten times, respectively. Results are shown in FIG. 3.

The SEC MALLS results confirm the SEC-HPLC results with levels of HMW aggregation in Erwinaze® CAMR176 (6%) higher when compared to recombinant L-asparaginase (1%).

Sedimentation Velocity AUC (svAUC) Method: Recombinant L-asparaginase and Erwinaze® samples were diluted to 10 mg/mL in 20 mM sodium phosphate, pH 7.0 and dialyzed against the same buffer. Samples were then placed into an AN-60Ti analytical rotor and loaded into a Beckman-Coulter ProteomeLab XL-analytical ultracentrifuge. The data were analyzed using the c(s) method developed by Peter Schuck at the N.I.H. and implemented in his analysis program SEDFIT (version 11.3). The resultant size distributions were graphed and the peaks were integrated using OriginLab Origin® version 9.0. In FIG. 4, the results demonstrate that recombinant L-asparaginase exhibits the highest homogeneity (due to the lowest aggregate content 1%) and the Erwinase® material is the least homogenous (aggregate 5%). In conclusion, measured by multiple orthogonal methods, recombinant L-asparaginase has a lower aggregate level than Erwinase®.

Example 6: Study to Evaluate Commercial Scale Protein Aggregation

This qualification study was conducted on a full scale recombinant L-asparaginase batch produced at 1000 L (intended commercial scale). The study consisted of analytical comparability with commercial product Erwinase® to ensure the small scale (SS) recombinant L-asparaginase comparability study in Example 5 was verified at full scale (1000 L). The study also used the SEC-MALLS method to characterize recombinant L-asparaginase.

One mL aliquots of recombinant L-asparaginase were pipetted into 5 mL PETG Bottles and stored at −20° C. The formulation was 20 mM sodium phosphate, 50 mM sodium chloride, 6.4% trehalose and the pH was 7.0.

SE-UHPLC Method: Size Exclusion Ultra High Pressure Liquid Chromatography (SE-UPLC) with UV detection is used to determine the purity of the recombinant L-asparaginase DS samples based on the size of the molecule, i.e. the hydrodynamic radius. Samples and reference material are diluted in Mobile Phase (10 mM phosphate, 0.3M arginine, 0.05% Sodium Azide) to 2.5 mg/mL and injected on to a Waters Acquity UPLC (BEH 200 SEC, 1.7 µm, 4.6×30 mm) column. Recombinant L-asparaginase DS is eluted isocratically at 0.4 mL/min. The purity profile is characterized by UV detection at 280 nm. For purity the % tetramer (main peak), % HMW and the % LMW are integrated and reported. The SE-UPLC profile of recombinant L-asparaginase DS consists of a main peak identified as the tetrameric form of the enzyme as well as a HMW peak which is identified as the Octomer in the SEC-MALLS analysis below. There are also very low levels of a low molecular weight (LMW) back shoulder. Percent areas are displayed in FIG. 5.

In line with the small scale data in Example 5 the SEC-UPLC showed that recombinant L-asparaginase FS batch (0.2%) has significantly lower aggregate values than Erwinase CAMR-174 (6%).

SEC-MALLS Method: High molecular weight species present in two samples (A and B) of the recombinant L-asparaginase were measured using SEC-MALLS Size Exclusion Chromatography coupled with a Multi Angle Light Scattering detector (SEC-MALLS). Samples were diluted with formulation buffer and injected on to a Superdex™ 200 Increase column with a Minidawn Treos MALLS Detector. FIG. 6 describes the percent UV peak areas. The results show that recombinant L-asparaginase is mainly present in tetrameric form with low levels of octamer and higher order aggregates. Minor levels of a LMW species were also noted.

Recombinant L-asparaginase and Erwinaze® samples were diluted to 10 mg/mL in 20 mM sodium phosphate, pH 7.0 and dialyzed against the same buffer. Samples were then placed into an AN-60Ti analytical rotor and loaded into a Beckman-Coulter ProteomeLab XL-analytical ultracentrifuge. The data were analyzed using the c(s) method developed by Peter Schuck at the N.I.H. and implemented in his analysis program SEDFIT (version 11.3). The resultant size distributions were graphed and the peaks were integrated using OriginLab Origin® version 9.0.

Figure 8:
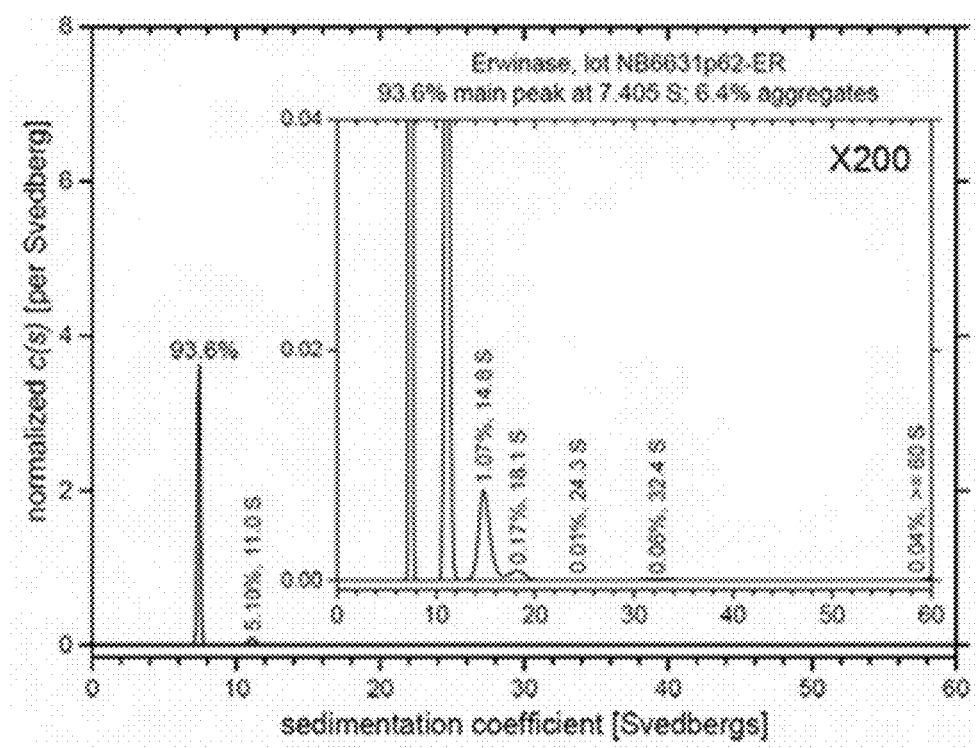
FIG. 8 shows the normalized sedimentation coefficient distribution of Erwinase® (commercial scale) as outlined in Example 6.

As seen in FIG. 7 and FIG. 8, recombinant L-asparaginase is highly homogenous with 99.2% in the tetrameric form of the enzyme with low levels of octamer (0.61%) and higher order aggregates (0.07%). This confirms the low aggregate levels observed in the SE-UHPLC and SEC-MALLS methods. The Erwinase® batch was observed to be more heterogeneous with 93.6% identified as tetramer with higher levels (6.4%) of HMW species present.

Example 7: A Randomized Phase 1 Study of the Safety, Tolerability, and Pharmacokinetics of Recombinant *Erwinia* Asparaginase (JZP-458) in Healthy Adult Volunteers JZP-458 is a recombinant *Erwinia* asparaginase produced using a novel *Pseudomonas fluorescens* expression platform that yields an enzyme with no immunologic cross-reactivity to *E. coli*-derived asparaginases. To evaluate the safety, tolerability, and pharmacokinetics of a single dose of JZP-458, a randomized, single-center, open-label, phase 1 study was conducted with JZP-458 given via intramuscular (IM) injection or intravenous (IV) infusion to healthy adult volunteers. In determining asparaginase efficacy, serum asparaginase activity (SAA) levels serve as a surrogate marker for asparagine depletion, and nadir SAA (NSAA) levels ≥0.1 IU/mL are the accepted threshold for demonstrating adequate asparagine depletion in clinical practice.

METHODS: A phase 1, randomized, single-center, open-label study was conducted in the US between Nov. 19, 2018 and May 20, 2019. The study was approved by the IntegReview Institutional Review Board in Austin, Texas, and conducted at QPS Miami Research Associates (Miami Clinical Research) in Miami, Florida, in accordance with the Declaration of Helsinki and Good Clinical Practice guidelines. All healthy volunteers provided written informed consent prior to enrollment. Eligible volunteers were men and nonpregnant, nonlactating women between the ages of 18 and 55 years with a normal body mass index (ie, 19.0-30.0 kg/m$^2$) who were in good general health as determined by the investigator at screening and Day-1 and were able to understand and comply with study-specific requirements. Main exclusions from the study included the history or presence of any illness, physical finding, laboratory examination or electrocardiogram finding that, in the opinion of the sponsor and/or the investigator, might confound the results or conduct of the study or pose a risk to the healthy volunteer. This included any condition that might interfere with the distribution, metabolism, or excretion of drugs.

Figure 20:
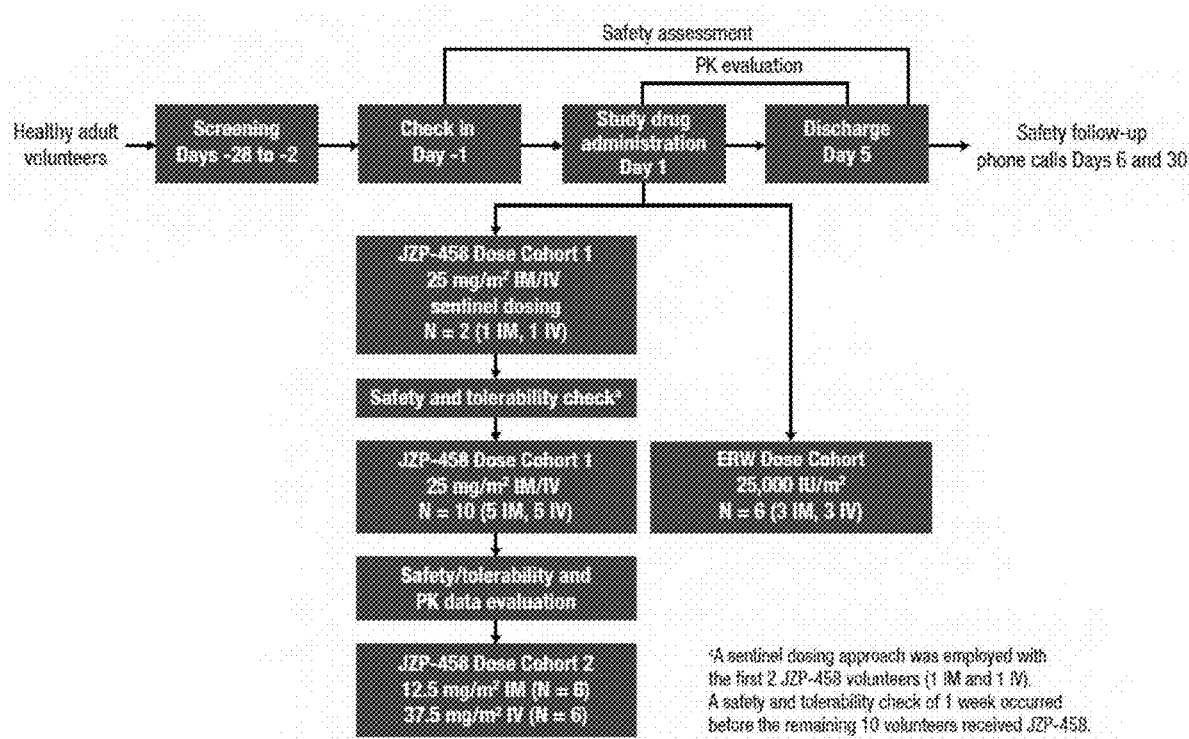
FIG. 20 shows the Study Design for the study in Example 7. Abbreviations: ERW, asparaginase *Erwinia chrysanthemi*; IM, intramuscular; IV, intravenous; PK, pharmacokinetics.
Figure 21:
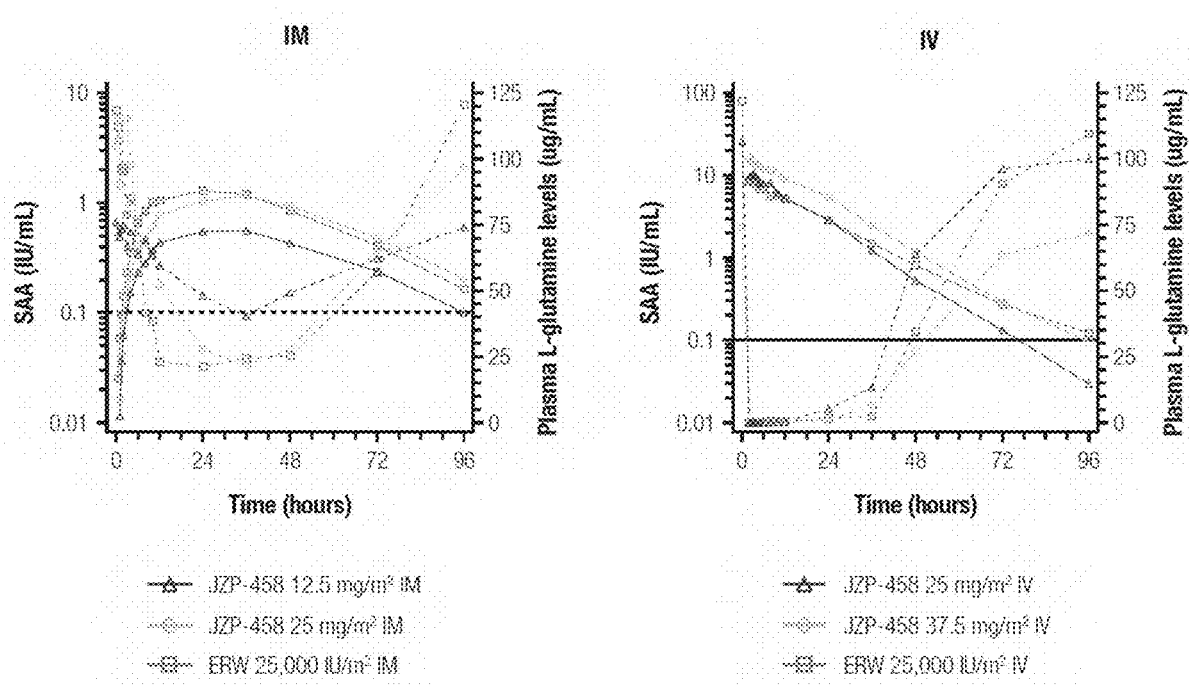
FIG. 21 shows Mean SAA-time Profiles for All Treatments and Corresponding Mean Plasma L-glutamine Levels as described further in the study in Example 7. Abbreviations: IM, intramuscular; IV, intravenous; SAA, serum asparaginase activity. Note: Lower limit of quantitation (LLOQ): asparaginase activity=0.0250 IU/mL; L-glutamine=0.250 ug/mL. Values below the LLOQ were set to zero. Abbreviations: IM, intramuscular; IV, intravenous; SAA, serum asparaginase activity. Note: Lower limit of quantitation (LLOQ): asparaginase activity=0.0250 IU/mL; L-glutamine=0.250 ug/mL. Values below the LLOQ were set to zero.

Study Design: This study screened healthy adult volunteers for eligibility between 2 and 28 days prior to dosing (FIG. 20). Eligible healthy volunteers checked in at the study center on Day-1 for baseline assessments, then were admitted to the inpatient clinic and received a single dose of the study drug on Day 1. All volunteers remained in the inpatient clinic for pharmacokinetic (PK) and safety assessments until they were discharged on Day 5. Safety follow-up phone calls regarding adverse events (AEs) occurred on Days 6 and 30.

This was an open-label study with a total enrollment of 30 healthy adult volunteers. The study used an adaptive design for JZP-458, where the starting dose for Cohort 1 was 25 mg/m$^2$, and the dose selection for Cohort 2 was based on safety, tolerability, and PK data from Cohort 1. A sentinel dosing approach was followed for JZP-458 for the first 2 volunteers dosed in the study, who were randomized to the JZP-458 Dose Cohort 1 only. These 2 volunteers were randomized to either IM or IV JZP-458, 1 to each route of administration. One week separated the sentinel dosing volunteers from the dosing of the remaining volunteers in the initial cohorts (JZP-458 Dose Cohort 1 and Erwinaze Dose Cohort), which was permitted by the protocol, as the safety and tolerability for the first 2 volunteers was deemed acceptable by the investigator and sponsor (no study-drug related AE≥Grade 3).

The next 16 volunteers were randomized to JZP-458 and Erwinaze Dose Cohorts with 10 volunteers randomized to the JZP-458 Dose Cohort 1 and 6 volunteers to the Erwinaze Dose Cohort. Within the JZP-458 Dose Cohort 1 and Erwinaze Dose Cohort, the volunteers were randomized to IM or IV treatment groups in a 1:1 ratio. This randomization schema is equivalent to randomizing all 18 volunteers to IM JZP-458, IV JZP-458, IM Erwinaze, or IV Erwinaze in a 2:2:1:1 ratio, while ensuring that the first 2 randomized volunteers received IM JZP-458 and IV JZP-458 following the sentinel dosing approach.

The safety, tolerability, and PK data for all volunteers in the JZP-458 Dose Cohort 1 was evaluated by the investigator and sponsor to determine the need to enroll volunteers in another cohort, JZP-458 Dose Cohort 2. However, during SAP development, it was determined that the JZP-458 Dose Cohort 2 would be performed and the previously collected safety, tolerability, and PK data were evaluated to determine the dose levels to be used in this cohort. For JZP-458 Dose Cohort 2, 12 additional volunteers were randomized to IM or IV treatment groups in a 1:1 ratio.

Objectives: The primary objective was to assess the safety and tolerability of a single dose of JZP-458 (IM or IV) in healthy adult volunteers, assessed by the occurrence of treatment-emergent adverse events (TEAEs) and clinically significant changes in vital signs and laboratory tests. The secondary objective was to characterize the PK of a single dose of JZP-458 (IM or IV) in healthy adult volunteers, based on SAA data. Additional assessments included serum asparaginase concentration (SAC) determinations for JZP-458, and the measurement of L-asparagine and L glutamine levels to assess the pharmacodynamic (PD) effect of JZP-458 in healthy adults.

Pharmacokinetic/Pharmacodynamic Sample Collection and Bioanalytical Method: Serial blood samples for PK/PD evaluation were collected from all healthy volunteers at prespecified timepoints up to 96 hours postdose. For IM dosing, samples were taken predose and at 0.5, 1, 1.5, 2, 3, 4, 6, 8, 10, 12, 24, 36, 48, 72, and 96 hours after dosing. For IV dosing, samples were taken predose and at 2, 2.5, 3, 3.5, 4, 5, 6, 8, 10, 12, 24, 36, 48, 72, and 96 hours after the start of the infusion. Blood samples for PK analysis were collected into labeled 4 mL EDTA tubes and kept on ice until the samples were centrifuged to serum. Blood samples for PD analysis were collected into 4 mL EDTA tubes and kept on ice until the samples were centrifuged to plasma.

The bioanalytical analysis for PK samples was performed by Charles River Laboratories (Skokie, IL). PK samples were assayed for SAA levels using a validated enzyme activity method in human serum over the range of 0.025 IU/mL to 0.15 IU/mL. In addition, PK samples were also assayed for SAC using a validated ECLIA enzyme content assay in human serum over the range of 1.0 ng/mL to 128 ng/mL. PD samples were assayed for L-asparagine and L-glutamine concentrations by Syneos Health (Princeton, NJ), using a validated liquid chromatography tandem mass spectrometry (LC/MS/MS) method over the range of 0.025 µg/mL to 10.0 µg/mL for L asparagine and 0.250 µg/mL to 100 µg/mL for L-glutamine Pharmacokinetic and Statistical Analyses: PK of JZP-458 was primarily evaluated based on SAA data. The following PK parameters were evaluated using noncompartmental analysis in Phoenix WinNonlin Version 6.3: $C_{max}$=maximum SAA; $C_{48\,h}$=SAA value at 48 hours; $C_{72\,h}$=SAA value at 72 hours; $t_{max}$=time to reach $C_{max}$; $AUC_{0-t}$=area under the SAA-time curve from time zero to time of last quantifiable SAA; $AUC_{0-inf}$=area under the SAA-time curve from time zero to infinity; CL=clearance; Vss=estimate of the volume of distribution at steady state following IV dosing; $V_z/F$=apparent volume of distribution following IM dosing, and $t_{1/2}$=terminal elimination half-life.

Descriptive statistics (n, mean, standard deviation, median, minimum and maximum) were used to summarize continuous data, while counts and percentages were used to summarize categorical data. Post hoc analyses were performed to assess the relationship between SAA and serum asparaginase concentration (SAC). Correlation and linear regression analyses were performed by study drug and across routes of administration, as well as by route of administration. In the linear regression modeling, SAC was the dependent variable and SAA was the independent variable. Lastly, no formal hypothesis testing was performed.

RESULTS: At the highest doses tested for each route of administration (ie, 25 mg/m² for IM and 37.5 mg/m² for IV), JZP-458 achieved serum asparaginase activity (SAA) levels ≥0.1 IU/mL at 72 hours postdose for 100% of healthy volunteers. All JZP-458 dose levels were well tolerated; there were no unanticipated adverse events (AEs), no serious AEs, and no grade 3 or higher AEs. Based on pharmacokinetic and safety data from this study, the recommended JZP-458 starting dose for the pivotal phase 2/3 study is 25 mg/m² for IM administration and 37.5 mg/m² for IV administration on a Monday/Wednesday/Friday dosing schedule.

Baseline Demographics: In total, 30 healthy adult volunteers were enrolled and randomized in the study. Of the 30 volunteers enrolled, all 30 completed the study, including the final scheduled safety follow-up phone call on Day 30. The overall baseline demographics (mean±SD) included the a mean±SD age of 38.4±8.30 years, weight of 77.04±9.998 kg, and BSA of 1.91±0.150 m² (FIG. 16). In addition, 63% were male, 97% were Hispanic or Latino ethnicity, 83% were White, and 17% were Black/African American.

Pharmacokinetics Analysis: The PK analysis set consisted of all 30 healthy volunteers (100%) enrolled in the study.

Figure 12:
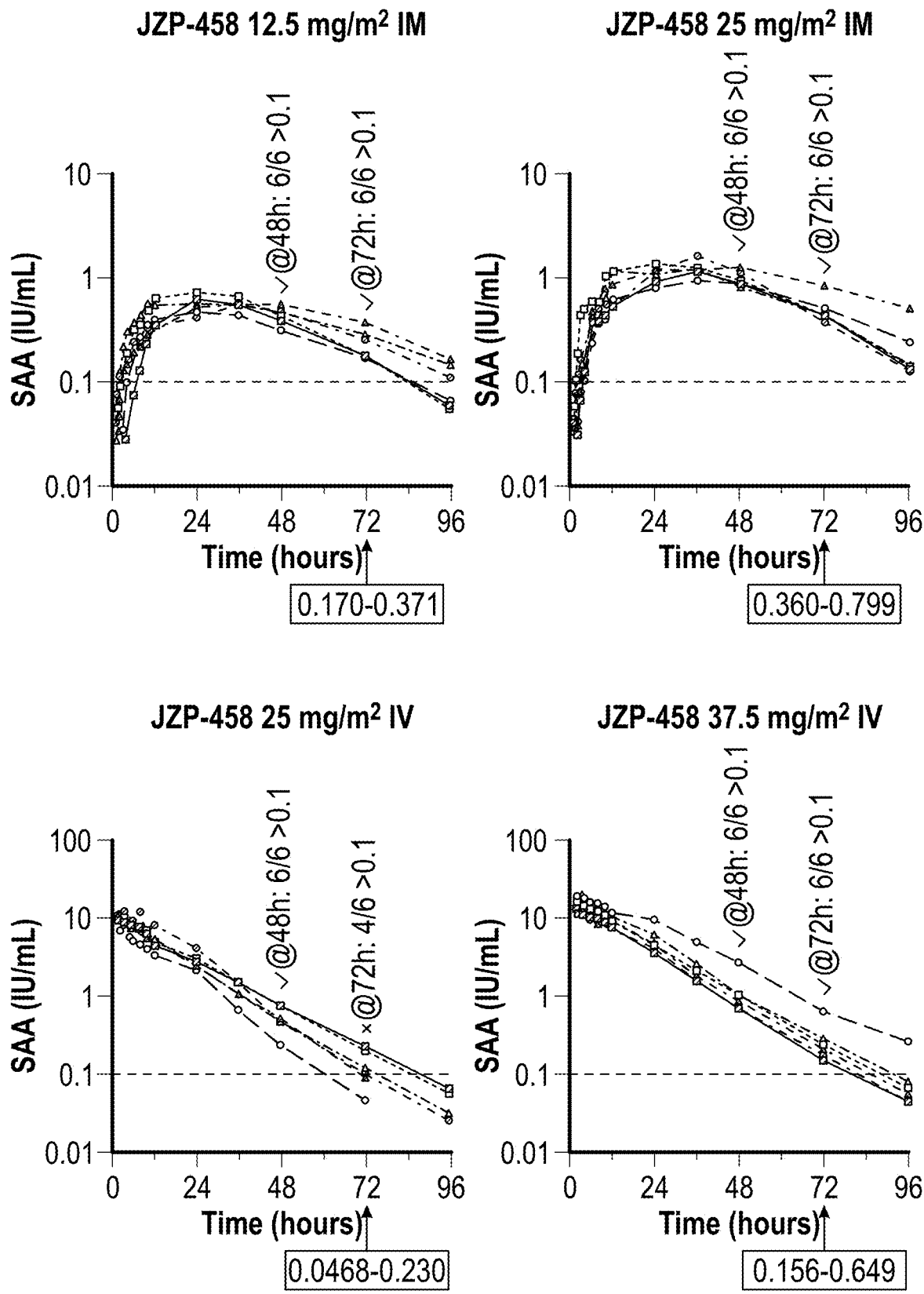
FIG. 12 shows individual SAA-time profiles. Abbreviations: ERW, asparaginase *Erwinia chrysanthemi*; IM, intramuscular; IV, intravenous; SAA, serum asparaginase activity. Further description can be found in Example 7.
Figure 12:
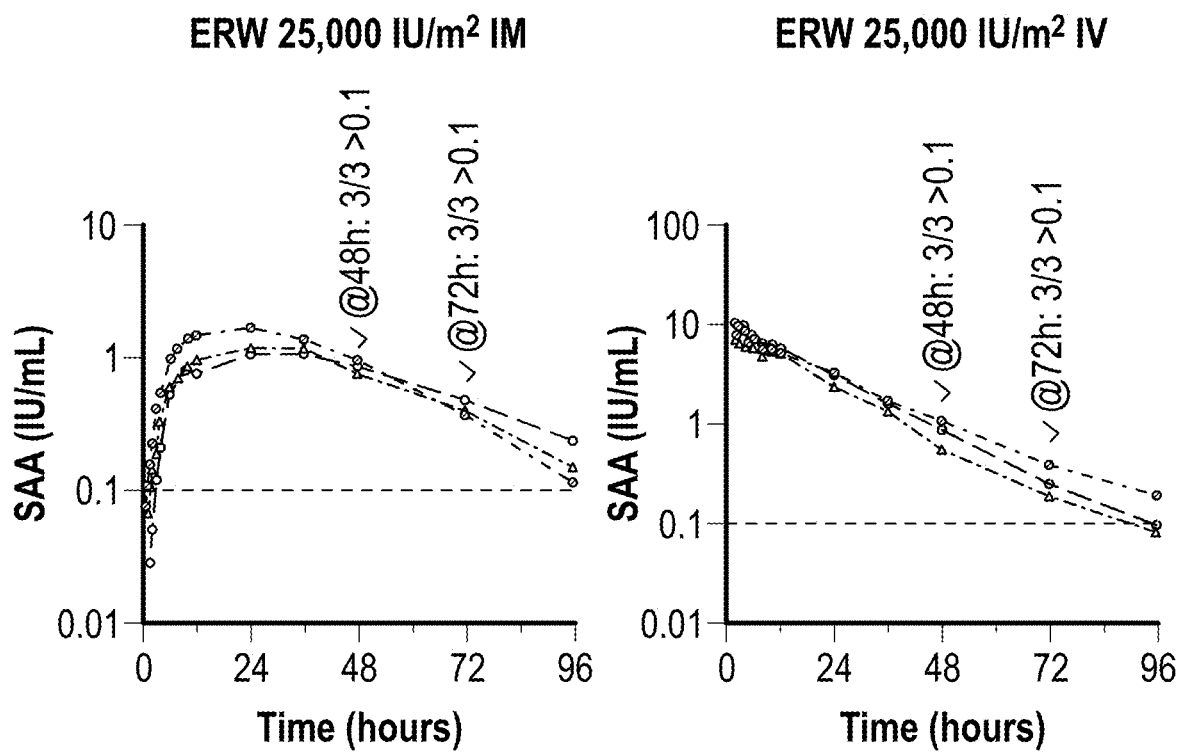

Serum Asparaginase Activity Data: In this study, the starting dose for JZP-458 Dose Cohort 1 was 25 mg/m². Individual SAA-time profiles were generated for all treatment groups (FIG. 12). Predose SAA values were below the limit of quantitation for all volunteers and all treatments. The number and proportion of volunteers with SAA levels ≥0.1 IU/mL and ≥0.4 IU/mL at 48 and 72 hours postdose are presented in FIG. 9.

The dose level of Cohort 2 was determined based on the safety, tolerability, and PK SAA data from Cohort 1. There were no unanticipated AEs, no reported serious AEs, and no grade 3 or higher AEs observed in Cohort 1. The PK SAA data for JZP-458 in Cohort 1 at 25 mg/m² is shown in FIG. 12. For the IM dose of 25 mg/m², SAA values at 72 hours postdose were ≥0.1 IU/mL in 6/6 (100%) healthy volunteers. This suggested that an IM dose of 25 mg/m² is expected to maintain SAA levels ≥0.1 IU/mL throughout the treatment duration on a Monday/Wednesday/Friday dosing schedule in the pivotal phase 2/3 study. Therefore, in Cohort 2, the IM dose level was decreased by 50% to 12.5 mg/m² to study the dose proportionality and safety profile at this dose. Alternatively, for an IV dose of 25 mg/m², SAA values at 72 hours postdose were ≥0.1 IU/mL in only 4/6 (67%) healthy volunteers. This suggested that the IV dose of 25 mg/m² was inadequate for maintaining SAA levels ≥0.1 IU/mL for 72 hours. Therefore, in Cohort 2, the IV dose level was increased by 50% to 37.5 mg/m².

Following IM administration of JZP-458, SAA levels achieved ≥0.1 IU/mL in 6/6 (100%) healthy volunteers at 48 and 72 hours postdose for both the 12.5 mg/m² and 25 mg/m² dose levels. After IV administration of JZP-458, SAA levels achieved ≥0.1 IU/mL in 6/6 (100%) healthy volunteers at 48 hours and in 4/6 (67%) healthy volunteers at 72 hours postdose at the dose level of 25 mg/m², while SAA levels achieved ≥0.1 IU/mL in 6/6 (100%) healthy volunteers at both 48 and 72 hours postdose at the dose level of 37.5 mg/m². Data suggested that at the same dose level, IM route of administration was able to maintained higher levels of SAA when compared with IV. SAA data for healthy volunteers who received ERW are also presented in FIG. 12 and FIG. 9.

Figure 13:
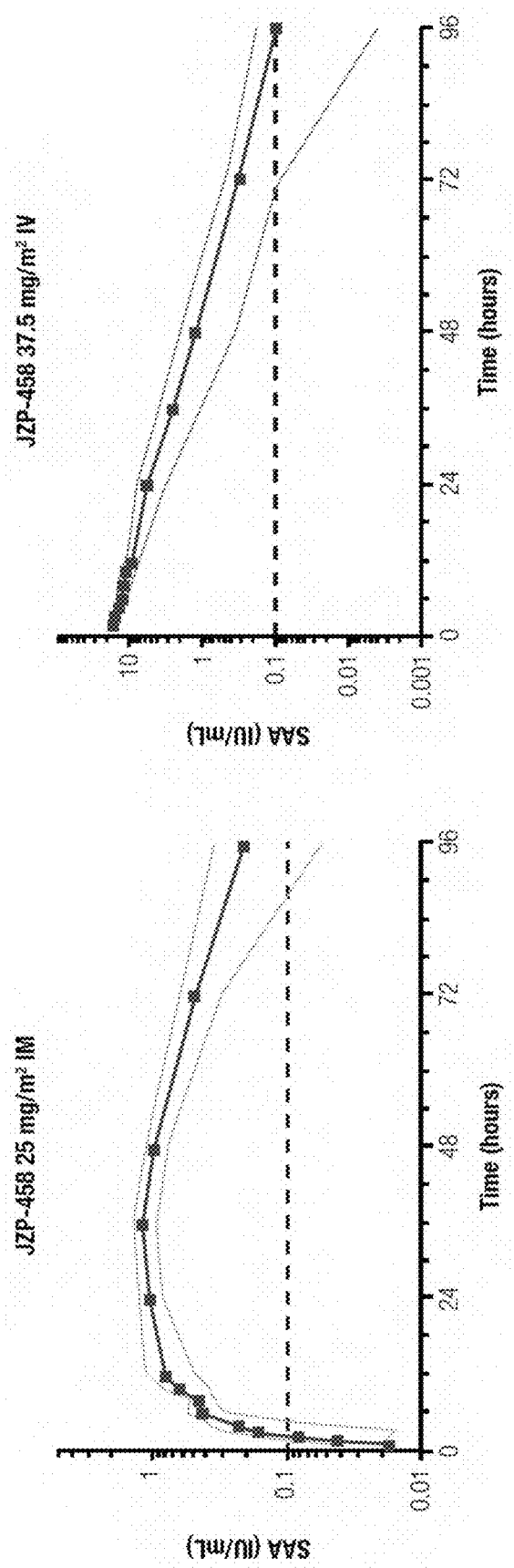
FIG. 13 shows mean (95% CI) SAA-time profiles as described further in Example 7. CI, confidence interval; IM, intramuscular; IV, intravenous; SAA, serum asparaginase activity.

Mean and 95% confidence interval (CI) curves for SAA were also generated for JZP-458 for IM administration at 25 mg/m² and IV administration at 37.5 mg/m² based on observed data (N=6 each; FIG. 13). Data indicated that the lower bound of 95% CI achieved ≥0.1 IU/mL at 72 hours postdose for both IM administration at 25 mg/m² and IV administration at 37.5 mg/m² for JZP-458 (lower bound of 95% CI for IM and IV were 0.31107 IU/mL and 0.09476 IU/mL, respectively). These data facilitated dose recommendations for the pivotal phase 2/3 study.

PK parameters based on SAA were summarized for all treatment groups (FIG. 10). When administered IM, JZP-458 was slowly absorbed based on SAA, with median $t_{max}$ of 24 hours and 36 hours following administration of 12.5 mg/m² and 25 mg/m² doses, respectively. Mean $t_{1/2}$ values of 23.4 hours and 19.1 hours were estimated following administration of 12.5 mg/m² and 25 mg/m², respectively. When administered IV, JZP-458 SAA levels declined with mean $t_{1/2}$ of 11.5 hours and 12.6 hours following administration of 25 mg/m² and 37.5 mg/m² doses, respectively. In general, the $t_{1/2}$ of JZP-458 after IM administration was longer than IV infusion due to absorption rate-limited elimination kinetics. Furthermore, the volume of distribution was approximately the same as the plasma volume, suggesting that JZP-458 was mostly confined to the central vascular compartment.

Dose proportionality assessment based on SAA showed that JZP-458 exposures increased with increasing doses based on SAA (FIG. 17). For both IM and IV administration, the increases in JZP-458 SAA exposures ($C_{max}$ and AUC) were approximately dose-proportional for the dose ranges studied. The bioavailability for JZP-458 for the IM route of administration was also calculated; it was estimated at 34.5% to 36.8% for JZP 458 based on SAA data.

Serum Asparaginase Concentration Data: Historically, asparaginase PK has been determined based on SAA data. However, SAA is not considered a true PK measurement; therefore, an enzyme content assay was developed to measure JZP-458 asparaginase concentrations in human serum.

Figure 14A:
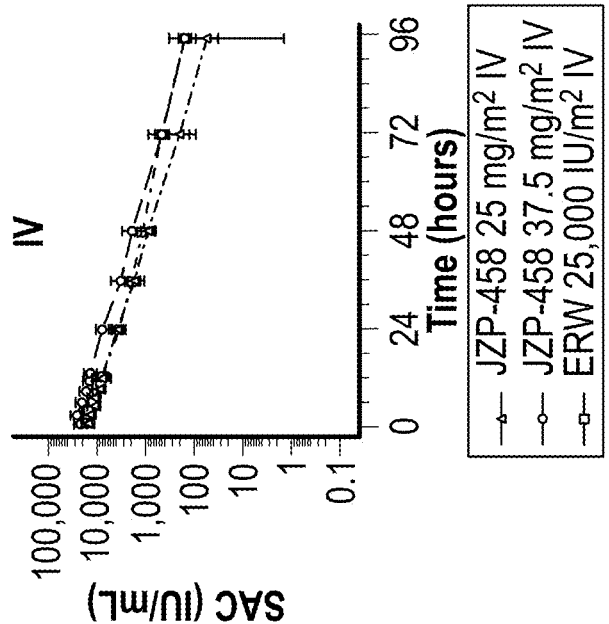
FIG. 14 shows A) Mean SAA-time profiles for JZP-458 IM. ERW, asparaginase *Erwinia chrysanthemi*; IM, intramuscular; SAC, serum asparaginase concentration. Note: Lower limit of quantitation (LLOQ)=1.00 ng/mL. Values below the LLOQ were set to zero, B) Mean SAA-time profiles for JZP-458 IV. ERW, asparaginase *Erwinia chrysanthemi*; Iv, intravenous; SAC, serum asparaginase concentration. Note: Lower limit of quantitation (LLOQ)=1.00 ng/mL. Values below the LLOQ were set to zero, C) Individual asparaginase concentration-time profiles. ERW, asparaginase *Erwinia chrysanthemi*; IM, intramuscular; IV, intravenous; SAC, serum asparaginase concentration, and D) Correlation between SAC and SAA for JZP-458 IM and IV administration. Abbreviations: IM, intramuscular; IV, intravenous; SAA, serum asparaginase activity; SAC, serum asparaginase concentration. Note: Regression line equation: SAC=1407.9×SAA; Pearson correlation coefficient=0.9779. Further description can be found in Example 7.
Figure 14B:
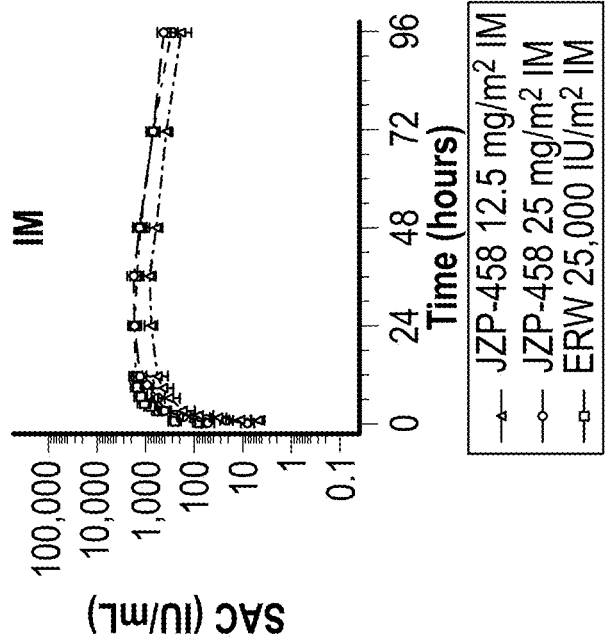
Figure 14C:
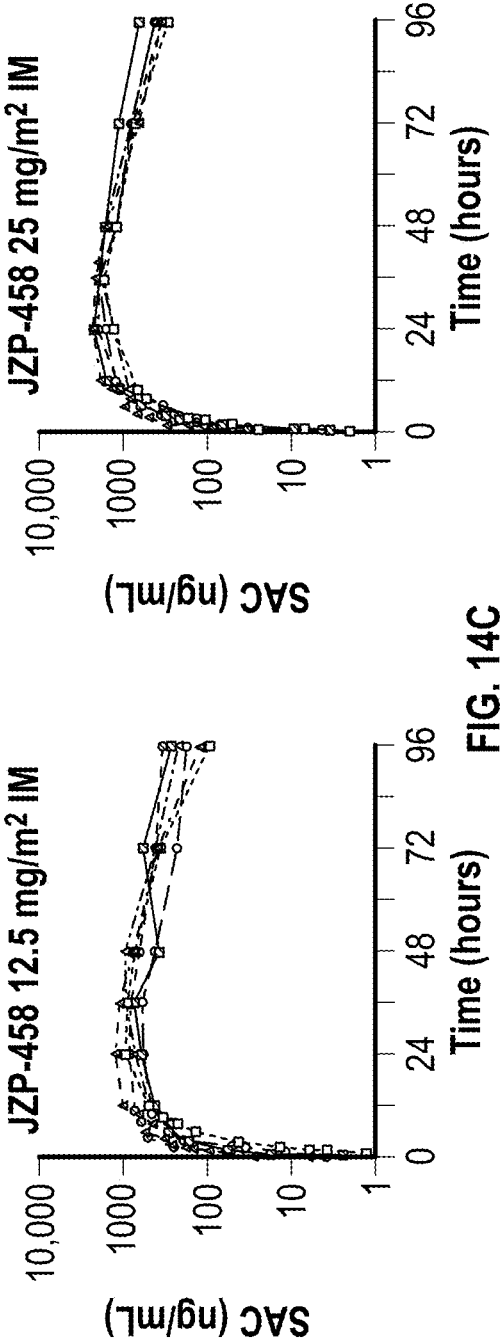
Figure 14C:
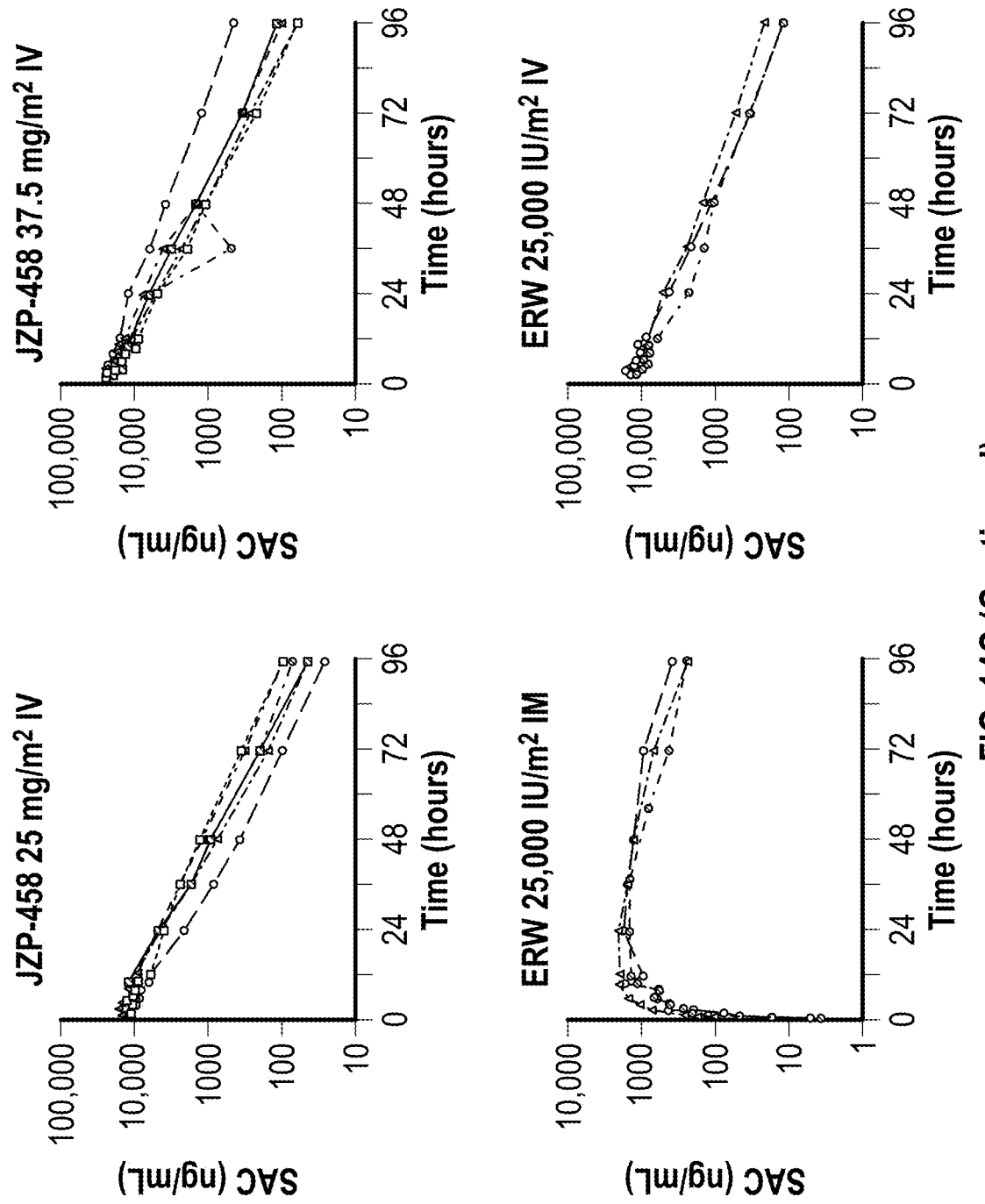

Individual and mean SAC-time profiles were generated for all treatment groups (FIG. 14A-C), and PK parameters based on SAC are summarized in FIG. 18. When administered IM, JZP-458 was slowly absorbed based on SAC, with median tmax values of 30 hours for both 12.5 mg/m² and 25 mg/m² doses. Mean $t_{1/2}$ values of 28.9 hours and 25.4 hours were estimated for JZP-458 at 12.5 mg/m² and 25 mg/m², respectively. Following IV administration of JZP-458, SAC levels declined with mean $t_{1/2}$ of 12.0 hours and 12.7 hours following administration of 25 mg/m² and 37.5 mg/m² doses, respectively.

Dose proportionality and bioavailability were also assessed for JZP-458 based on SAC (FIG. 19). JZP-458 exposures increased with increasing dose based on SAC. For both IM and IV administration, the increases in JZP-458 exposures based on SAC ($C_{max}$ and AUC) were approximately dose-proportional for the dose ranges studied. For the IM route of administration, bioavailability was estimated at 37.7% to 43.9% for JZP-458 based on SAC data.

Figure 14D:
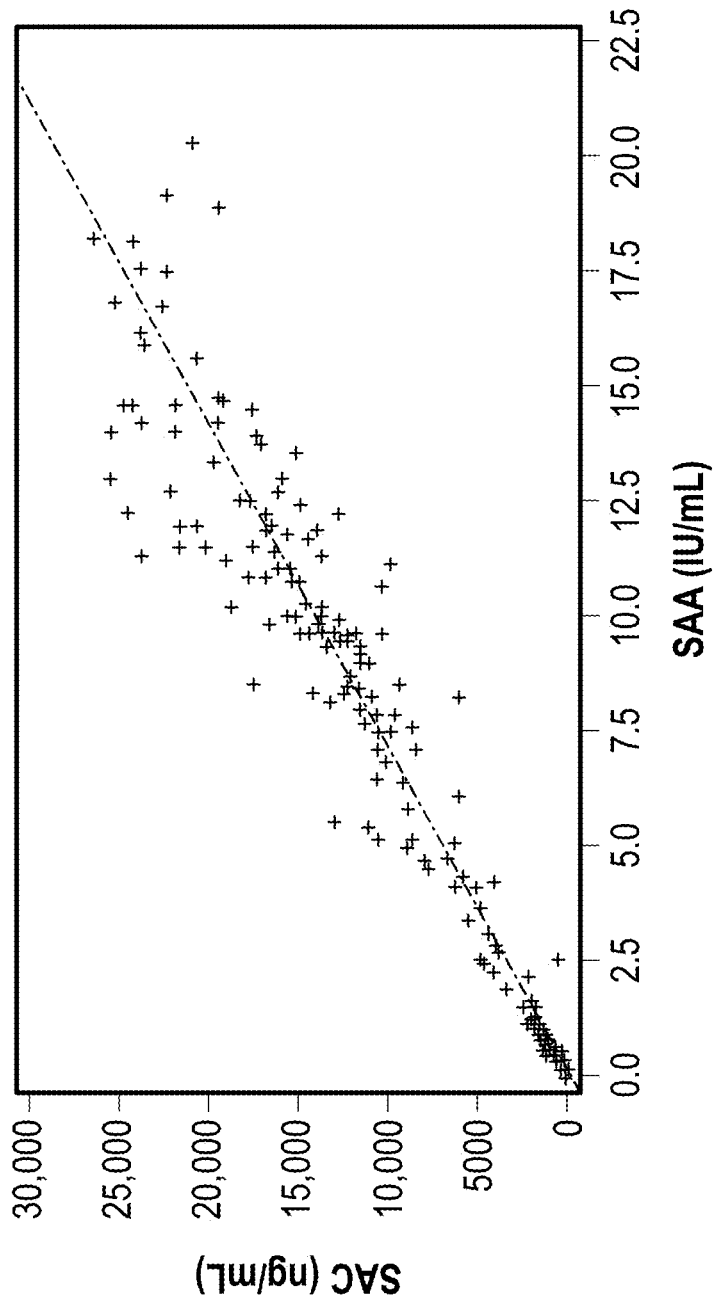

The relationship between SAA and SAC was further explored for JZP-458 (FIG. 14D). When assessed across routes of administration for JZP-458, a strong positive association was observed between SAA and SAC with a correlation coefficient greater than 0.95. Additionally, the equation from the linear regression model was SAC=1407.9×SAA. These data suggest that when SAA levels are at 0.1 IU/mL, the corresponding SAC would be approximately 141 ng/mL in this healthy adult population.

Figure 15:
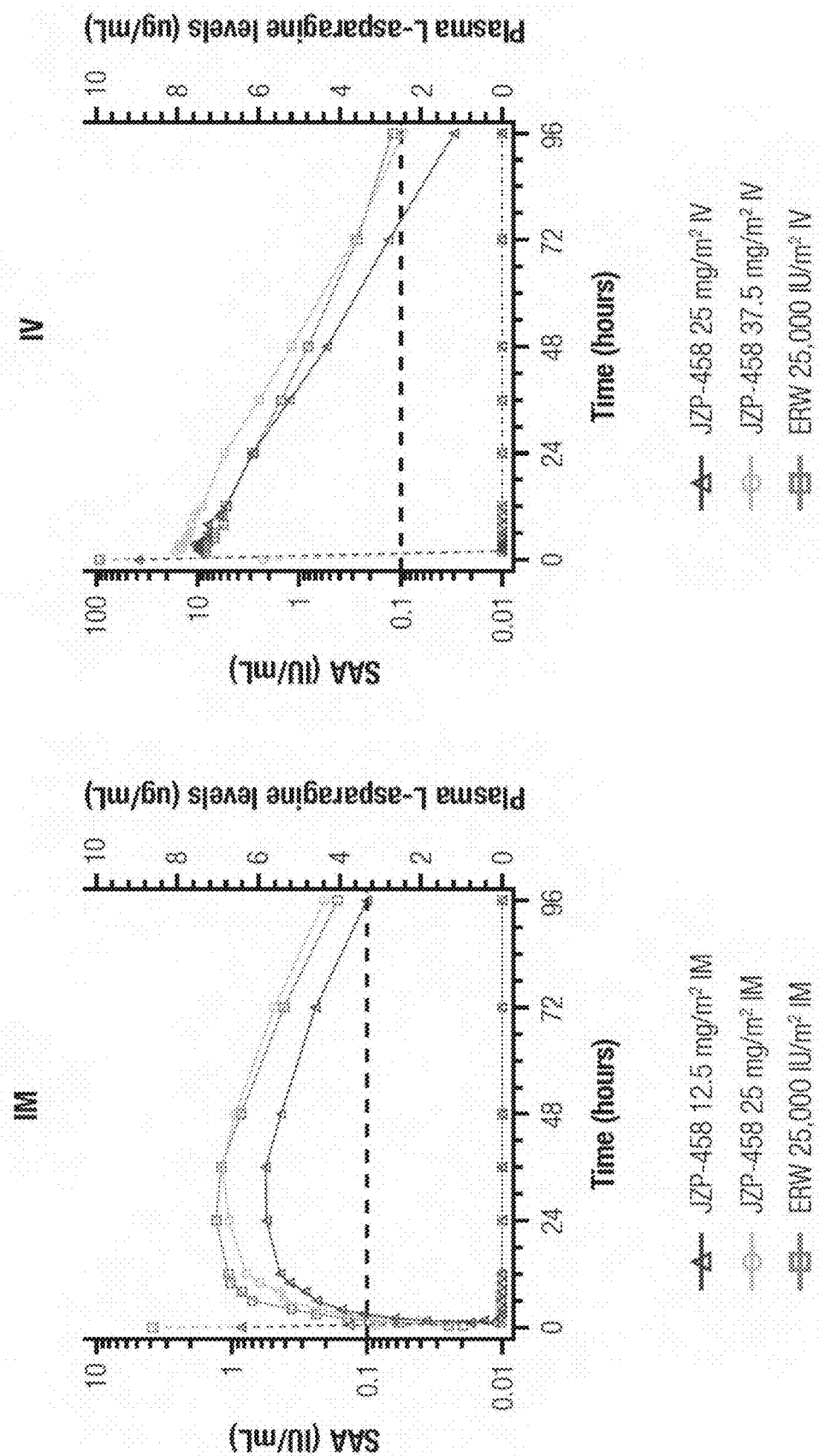
FIG. 15 shows mean SAA-time profiles and corresponding mean plasma L-asparagine levels further described in the study in Example 7. IM, intramuscular; IV, intravenous; SAA, serum asparaginase activity. Note: Lower limit of quantitation (LLOQ): asparaginase activity=0.0250 IU/mL; L-asparagine=0.0250 ug/mL. Values below the LLOQ were set to zero.

Pharmacodynamic Data: Asparaginase hydrolyzes the amino acid asparagine into aspartic acid and ammonia. Plasma levels of asparagine were monitored throughout the treatment duration. Mean SAA versus mean plasma asparagine concentration over time profiles are provided in FIG. 15. Baseline (predose) mean plasma asparagine concentrations were similar for IM and IV groups; individual asparagine concentrations ranged from 5.09 μg/mL to 13.8 μg/mL for all volunteers, which is consistent with literature-reported values. After JZP-458 administration (IM and IV), mean plasma asparagine levels were rapidly depleted from the predose concentrations (Cohort 1: 8.62 μg/mL and 8.96 μg/mL for IM and IV, respectively; Cohort 2: 6.42 μg/mL and 5.89 μg/mL for IM and IV, respectively) to levels below the assay lower limit of quantitation (LLOQ; 0.025 μg/mL) for both routes, and remained undetectable through the final sample collection time point at 96 hours. Data indicated that there was direct correlation between SAA and the reduction in plasma asparagine levels. At all JZP-458 dose levels, plasma asparagine levels were completely depleted with JZP-458 administration. At the highest JZP-458 doses tested (ie, 25 mg/m² for IM and 37.5 mg/m² for IV) in this phase 1 healthy volunteer study, JZP-458 not only achieved SAA levels ≥0.1 IU/mL at 72 hours postdose for 100% of the healthy volunteers for each route, but also resulted in a complete depletion of plasma asparagine levels through 96 hours postdose.

In addition to asparagine, asparaginase is also capable of hydrolyzing glutamine to glutamic acid and ammonia, but with much less efficiency. Plasma levels of glutamine were monitored for all treatments (FIG. 17). Baseline (predose) mean plasma glutamine concentrations were similar for IM and IV groups; individual glutamine predose concentrations ranged from 60.4 μg/mL to 146 μg/mL for all volunteers, which is also consistent with literature-reported values. Data showed that mean plasma glutamine levels fell quickly following JZP-458 IV administration from the predose concentrations of 106.5 and 74.0 μg/mL for Cohort 1 and Cohort 2, respectively, to levels below the assay LLOQ (0.25 μg/mL) for approximately 12 hours, after which glutamine levels recover to approximately predose levels at the final sample collection time point at 96 hours postdose. For the IM route, mean plasma glutamine levels declined following IM administration of JZP-458, with the lowest glutamine level observed at 36 hours postdose with 79% and 47% glutamine depletion at 25 mg/m² and 12.5 mg/m², respectively, after which glutamine levels recovered to levels similar to predose at the last sample collection time point of 96 hours postdose. Complete depletion of L-glutamine was not observed; glutamine levels were moderately affected to only partial depletion, and data were more variable than those observed for L-asparagine.

Safety and Tolerability: The safety profile observed for JZP-458 in this phase 1 study was consistent with profiles of other asparaginases. All dose levels of JZP-458 were well tolerated; there were no unanticipated AEs, no serious AEs, and no grade 3 or higher AEs. The most common TEAE occurring in ≥2 healthy volunteers in each dosing cohort was nausea (FIG. 11).

DISCUSSION: JZP-458, a recombinant Erwinia asparaginase with no expected immunologic cross-reactivity to E. coli-derived asparaginases, is being developed to ensure the availability of asparaginase therapy for patients with ALL or LBL who develop hypersensitivity to E. coli-derived asparaginases. In this randomized, single-center, open-label, phase 1 study, at the highest doses tested for each route of administration (ie, 25 mg/m² for IM and 37.5 mg/m² for IV), JZP-458 achieved SAA levels ≥0.1 IU/mL at 72 hours postdose for 100% of the healthy adult volunteers in each route. The SAA levels observed in this study also indicated that JZP-458 is capable of complete depletion of plasma asparagine levels. This was confirmed by asparagine concentrations measured from this study. At all JZP-458 dose levels, plasma asparagine levels were completely depleted with JZP-458 treatment with both IM and IV routes of administration. Additionally, the safety profile for JZP-458 in this study was consistent with the profiles of other asparaginases. All dose levels of JZP-458 were well tolerated; there were no unanticipated AEs, no reported serious AEs, and no grade 3 or higher AEs.

Based on the cumulative PK and safety data, the recommended pivotal phase 2/3 JZP-458 starting dose is 25 mg/m² for the IM route of administration and 37.5 mg/m² for the IV route of administration on a Monday/Wednesday/Friday dosing schedule. These doses achieved SAA levels ≥0.1 IU/mL at 72 hours postdose for 6/6 (100%) healthy volunteers in this phase 1 study in healthy adult volunteers, and these doses are expected to maintain SAA levels ≥0.1 IU/mL throughout the treatment duration in the pivotal phase 2/3 study.

Completing asparaginase therapy is important for improved patient outcomes and as has been shown in previous studies. In the Dana-Farber Cancer Institute ALL Consortium Protocol 91-01 study, patients with asparaginase intolerance, defined as completion of ≤25 weeks of a planned total of 30 weeks of asparaginase therapy, had a significantly lower 5 year EFS when compared with patients who received ≥26 weeks of asparaginase therapy (73% vs 90%, respectively; P<0.01). A recent Children's Oncology Group study demonstrated that high-risk and slow early-responding standard-risk ALL patients who did not complete their prescribed asparaginase doses had a significantly inferior EFS compared with patients who received all prescribed asparaginase doses. Notably, patients with hypersensitivity reactions who completed their course of therapy with Erwinia asparaginase substitution showed similar EFS as those who completed their course of first-line asparaginase therapy. These studies suggest that patients who complete their prescribed asparaginase doses, whether on first- or second-line asparaginase, have better outcomes than those who discontinue early. These results highlight the need for alternative asparaginase preparations to ensure that patients who develop hypersensitivity to E. coli-derived asparaginases are able to complete their full treatment course.

CONCLUSIONS: At the highest doses tested for each route of administration (ie, 25 mg/m² for IM and 37.5 mg/m² for IV), JZP-458 achieved SAA levels ≥0.1 IU/mL at 72 hours postdose in each route for 100% of the healthy adult volunteers in this phase 1 study, and resulted in complete asparagine depletion with no unanticipated AEs, SAEs, or grade ≥3 AEs. Based on the cumulative PK and safety data from this study, the recommended phase 2/3 JZP-458 starting dose is 25 mg/m$^2$ for the IM route of administration and 37.5 mg/m$^2$ for the IV route of administration on a Monday/Wednesday/Friday dosing schedule. JZP-458 may be used as a treatment alternative for ALL/LBL patients who develop hypersensitivity to *E. coli*-derived asparaginases.

Example 8: Phase 2/3 Study of JZP-458 in ALL/LBL Patients Hypersensitive to *E. coli* Derived Asparaginases An open-label, multicenter, dose confirmation, and PK study of JZP-458 was designed for participants (of any age) with ALL/LBL who are hypersensitive to *E. coli*-derived asparaginases (allergic reaction or silent inactivation). This study was designed to assess the tolerability and efficacy of JZP-458, as measured by serum asparaginase activity with additional supportive analyses for asparagine depletion and anti-drug antibody (ADA) levels. Six doses of JZP-458 are substituted for each dose of a long-acting *E. coli*-derived asparaginase. Two consecutive weeks of treatment with JZP-458 is defined as one course.

Figure 22:
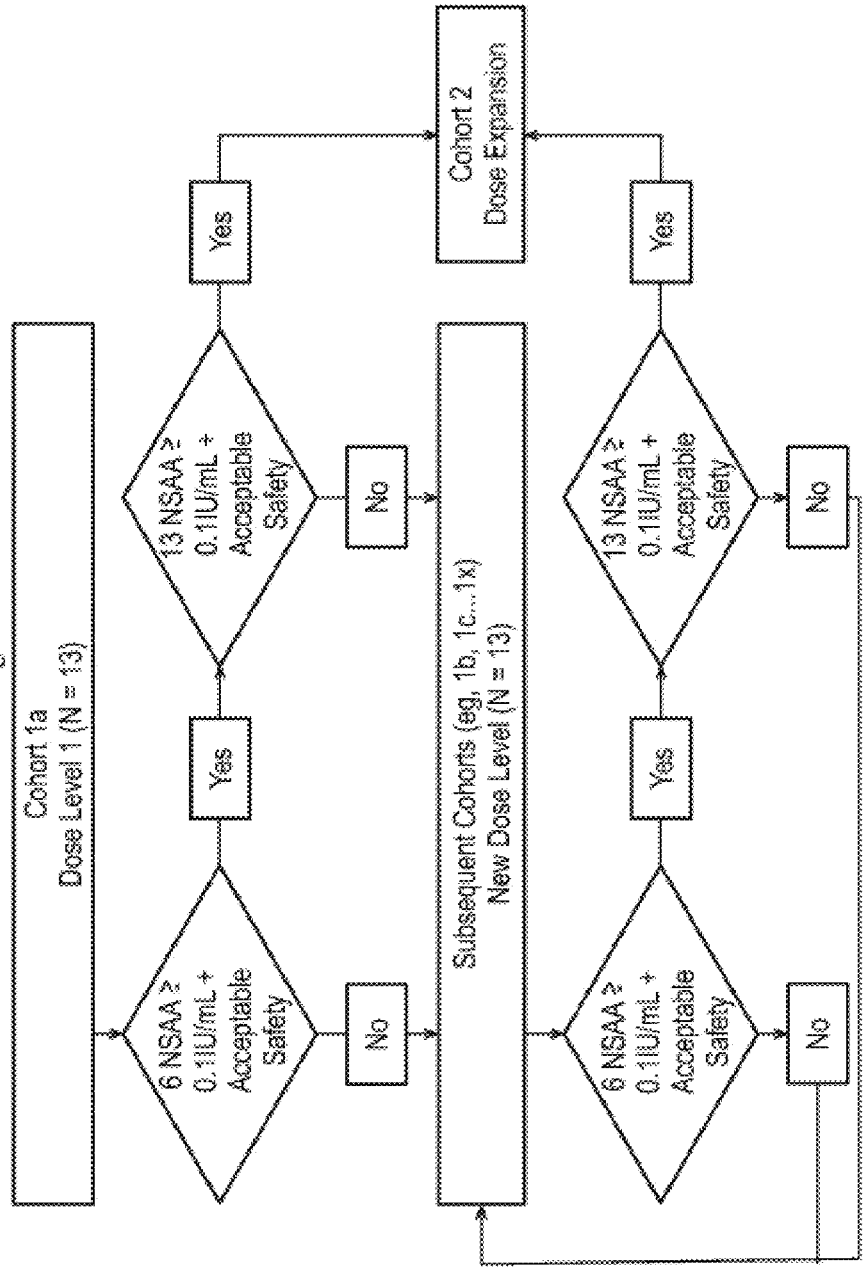
FIG. 22 shows Part A IM JZP-458 Dose Cohorts (Example 8). The SDRC will assess the safety and tolerability issues for participants in Cohort 1 to determine if additional participants at different dose levels are needed or if the appropriate IM JZP-458 dose level to proceed to the Expansion Cohort (Cohort 2) has been determined. The SDRC will review NSAA and safety/tolerability data when 6 and 13 evaluable participants in each subcohort complete Course 1; enrollment will not stop at the specified time points for SDRC review. Abbreviations: IM=intramuscular; IU=International Units; NSAA=nadir serum asparaginase activity; SDRC=Study Data Review Committee

STUDY DESIGN: This study consists of 2 parts: Part A to determine the dose of JZP-458 for IM administration and to confirm safety and efficacy; and Part B to define the optimal dose and schedule of IV JZP-458 (see FIG. 22 and FIG. 23). Part A and Part B may be investigated in parallel. Part A (IM) is investigating multiple cohorts: in Cohort 1, the optimal dose will be determined; and in Cohort 2, the number of participants treated at the optimal dose will be expanded. Part B (IV) will mirror Part A: in both parts, a course of JZP-458 (6 doses over 2 weeks) may start on either a Monday, Wednesday, or a Friday and the number of courses per participant will depend on their individual treatment plan. In each part, a course of JZP-458 (6 doses over 2 weeks) may start on either a Monday, Wednesday, or a Friday; the number of courses per participant will depend on their individual treatment plan. The starting dose was 25 mg/m$^2$ for the IM route of administration (Cohort 1a). The starting dose was selected based on the phase 1 study results.

OBJECTIVES: The primary objectives of the study are to determine the efficacy of IM JZP-458 administration as measured by the response in Cohort 1 and Cohort 2, which is defined as the last 72 hour NSAA level ≥0.1 IU/mL during the first course, and to assess the safety and tolerability of IM JZP-458 in participants with ALL/LBL who are hypersensitive to *E. coli* derived asparaginases. Additional objectives include the following:

Key Secondary Objective: To determine the efficacy of IM JZP-458 administration as measured by the response in Cohort 1 and Cohort 2, defined as the last 48-hour NSAA level ≥0.1 IU/mL during the first course.

Secondary Objectives: 1) To determine the efficacy of IM JZP-458 administration as measured by the response in Cohort 1 and Cohort 2, defined as the last 48-hour and the last 72-hour NSAA levels ≥0.4 IU/mL during the first course, 2) To characterize the PK of IM JZP-458 using a PPK approach and to explore E-R correlations using data from all participants from all dose levels and samples from all time points, and 3) To assess the immunogenicity of IM JZP-458 following repeat administration of JZP-458.

Exploratory Objectives (for Part B of the study): 1) To determine the efficacy of IV JZP-458 administration as measured by the response, defined as the last 48-hour NSAA ≥0.1 IU/mL and the last 72-hour NSAA ≥0.1 IU/mL during the first course, 2) To determine the efficacy of IV JZP-458 administration measured by the response, defined as the last 48-hour NSAA ≥0.4 IU/mL and the last 72-hour NSAA ≥0.4 IU/mL during the first course, 3) To assess the safety and tolerability of IV JZP-458 in participants with ALL/LBL who are hypersensitive to *E. coli*-derived asparaginases, 4) To characterize the PK of IV JZP-458 using a population PK approach and 5) To assess the immunogenicity of IV JZP-458 following repeat administration of JZP-458.

Preliminary Results: As of 7 Oct. 2020, 31 participants have enrolled in Cohort 1a and 56 participants in Cohort 1b of the pivotal Phase 2/3 study (JZP458-201). The first protocol-defined SDRC evaluation of Cohort 1a included data from 6 evaluable participants, and the second SDRC evaluation of Cohort 1a included cumulative data from 16 evaluable participants. Each SDRC recommendation is based on a review of all available data at that time. After an evaluation of available efficacy data and because there were no unanticipated safety events observed at the IM 25 mg/m$^2$ dose level, the IM 37.5 mg/m$^2$ dose level evaluation was initiated (Cohort 1b). The first participant enrolled in Cohort 1b on 29 Jun. 2020. SDRC evaluation of Cohort 1b data occurred on 1 Sep. 2020 as a preliminary review of data through the first 7 participants enrolled in Cohort 1b. This review included all available SAA data, PPK modeling and simulation data, and safety data from the study. The recommendation was to continue enrollment without modifications and to review the study again when data are available for at least 13 evaluable participants in Cohort 1b, in line with the SDRC Charter. Available preliminary results from Cohorts 1a (N=31) and 1b (N=17) are summarized below.

Serum Asparaginase Activity Levels

Serum samples were assayed for SAA. SAA levels serve as a surrogate marker for efficacy and response. The bioanalytical analyses for SAA were performed by Charles River Laboratories (Skokie, IL), using a validated enzyme activity method in human serum and JZP-458 reference standard (lot #RM-M-009; specific activity of 693 U/mg) over the range of 0.035 IU/mL to 0.210 IU/mL.

Evaluable participants for Cohort 1 were defined as participants who had received at least 3 doses of IM JZP-458 and had a 72-hour NSAA level collected within the protocol-defined sample collection window (±2 hours) during the second half of Course 1. Of the 31 participants enrolled at 25 mg/m2, 26 participants were considered evaluable for the purpose of the primary efficacy objective in Cohort 1 per protocol. Reasons for participants being considered unevaluable included the following: 1) 2 participants had 72-hour PK samples collected out of the defined sample collection time window. 2) 1 participant had no 72-hour PK sample collected. 3) 1 participant withdrew informed consent and had no PK samples collected. 4) 1 participant had SAA values that were unevaluable due to assay interference from elevated lipids (as assessed by the bioanalytical laboratory, Charles River Laboratory). This participant had Grade 2 hypertriglyceridemia (318 mg/dL) at baseline and Grade 4 hypertriglyceridemia (2679 mg/dL) (reported as a TEAE; see details in safety summary below) during Course 1. The participant's triglycerides continued to decrease to baseline or below baseline in subsequent courses of JZP-458, and more recently, the participant completed Course 5 with triglycerides levels decreased to 234 mg/dL (Grade 1).

Of the 17 participants included in the preliminary analysis for Cohort 1b (37.5 mg/m2), 16 participants were evaluable for the purpose of the primary efficacy objective in Cohort 1 (1 participant had a 72-hour PK sample collected out of the defined collection window, so was excluded for the primary endpoint but is included for other endpoints). Preliminary individual SAA results at key time points are summarized in FIG. 24. Preliminary observed SAA results show that at JZP-458 IM dose level of 25 mg/m$^2$ (N=26 evaluable participants), the mean (95% CI) SAA levels at the last 72 and 48 hours postdose were 0.1560 (0.1144-0.1976) and 0.4504 (0.3637-0.5370), respectively (median [first quartile, Q1; third quartile, Q3] SAA levels at the last 72 and 48 hours postdose were 0.1345 [0.0886, 0.2178] and 0.4091 [0.2813, 0.6577], respectively). At JZP-458 IM dose level of 37.5 mg/m$^2$ (N=16 evaluable participants), the mean (95% CI) SAA levels at the last 72 and 48 hours postdose were 0.2605 (0.1326-0.3884) and 0.7146 (0.3976-1.0316), respectively (median [Q1, Q3] SAA levels at the last 72 and 48 hours postdose were 0.1732 [0.1157, 0.2849] and 0.6503 [0.3248, 0.8736], respectively).

The proportions of participants with NSAA levels ≥0.1 IU/mL and ≥0.4 IU/mL at the last 72 and 48 hours postdose are presented in FIG. 25. At JZP-458 IM dose levels of 25 mg/m$^2$ (N=26 evaluable participants) and 37.5 mg/m$^2$ (N=16 evaluable participants), 65.4% and 81.3% of participants, respectively, achieved NSAA levels ≥0.1 IU/mL at the last 72-hour assessment (primary endpoint); and 96.2% and 93.8% of participants, respectively, achieved NSAA levels ≥0.1 IU/mL at the last 48-hour assessment (key secondary endpoint).

Population Pharmacokinetic Modeling and Simulation: Preliminary PPK analyses (secondary endpoint) have been performed using SAA data (data received on 28 Sep. 2020). A total of 319 quantifiable SAA data points (Course 1 only) from 47 participants (30 participants at 25 mg/m$^2$ and 17 participants at 37.5 mg/m$^2$) from the JZP458-201 study who received IM JZP-458 were included in the PPK model development. Models were fit to the SAA data to identify a structural model. Weight, height, body surface area, age, gender, race, ethnicity, disease, and disease subtype were tested as potential covariates on JZP-458 SAA clearance and volume. Only weight was found to be statistically significant and was included in the model.

The covariate model developed for JZP-458 was a 1-compartment IM-only model with linear elimination and first order absorption, with weight included as an allometric covariate on JZP-458 SAA clearance and volume, and a proportional residual error model. Model diagnostics showed good fits based on the redicted versus the observed data and predictive modeling methodologies.

The covariate model was used to simulate patient SAA profiles (N=2000 subjects per dose level) to explore the likelihood of achieving a therapeutic NSAA level of ≥0.1 IU/mL. The simulated virtual populations were created by resampling subjects with replacement from demographics in the Centers for Disease Control National Health and Nutrition Examination Survey Data. The simulation population ranged from 2 to 85 years of age, with a weight range of 8.9 to 174.6 kg (median 62.7 kg).

Figure 26:
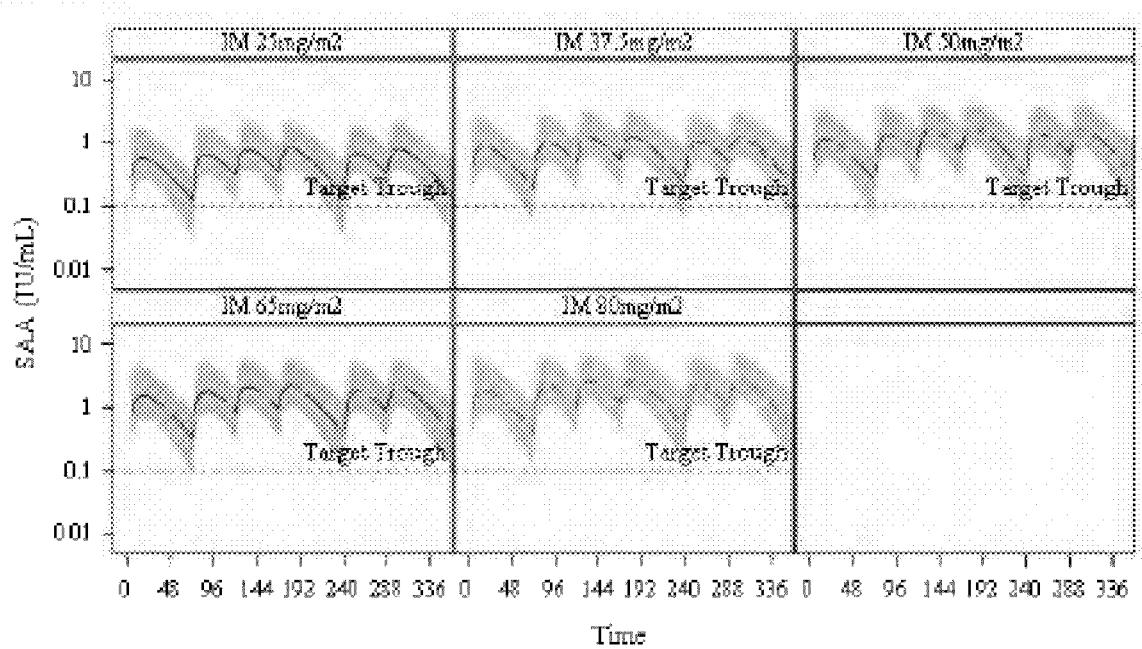
FIG. 26 shows simulated JZP-458 Median SAA Profiles with 95% Prediction Intervals-Semi-log scale (FMW Dosing Schedule) (Example 8 IM Simulation Model). Abbreviations: IM=intramuscular; FMW=Friday, Monday, Wednesday; SAA=serum asparaginase activity Center lines are the median value; bands (95% prediction interval) represent the 2.5th (lower) and 97.5th (upper) percentiles. The x-axis is displayed out to 336 hours with an extra offset, the data plotted include simulated observations to 504 hours after the start of the course.

Both Friday, Monday, Wednesday (FMW) and MWF dosing schedules were simulated for 6 doses per 1 course of treatment, with a focus on the FMW schedule because it represented the most conservative scenario with the first 72-hour NSAA after only one dose. Simulation data indicated that start day does not impact the simulated percentage of patients with NSAA levels ≥0.1 IU/mL for the last 48- or 72-hour time points. Simulated profiles for FMW dosing schedule with median and 95% prediction intervals are presented in FIG. 26. Tabular summaries of the simulated percentage of patients achieving NSAA ≥0.1 IU/mL, and the mean predicted SAA levels for IM doses ranging from 25 to 80 mg/m$^2$ are presented in FIG. 27.

Based on PPK modeling and simulation, at an IM dose of 37.5 mg/m$^2$ JZP-458 on a FMW schedule, JZP-458 is expected to achieve the last 72-hour NSAA levels ≥0.1 IU/mL in 87% of patients (95% CI: 85.5%-88.5%) and to achieve the last 48-hour NSAA level ≥0.1 IU/mL in 99.9% of patients (95% CI: 99.7%-100%); the simulated mean NSAA levels were 0.29 (95% prediction interval: 0.06-0.88) and 0.58 (95% prediction interval: 0.2-1.32) at the last 72 and 48 hours, respectively. The PPK model predicts that at a dose of 50 mg/m$^2$, 94.2% of patients would achieve NSAA levels ≥0.1 IU/mL at 72 hours postdose.

Preliminary Asparagine Depletion Results: Pharmacodynamic samples were assayed for asparagine concentrations by Syneos Health (Princeton, NJ), using a validated liquid chromatography tandem mass spectrometry method over the range of 0.025 to 10.0 µg/mL (Biomarker Partial Validation Report Amendment 1, SN 0044). Blood samples for asparagine assay were placed in ice bath immediately after collection and processed plasma was stored at −80° C. within 30 minutes to ensure analytical measurements represent in vivo asparagine levels. Asparagine levels were measured to support the effectiveness of JZP-458 over the dosing interval. The average baseline asparagine level was 10.2557 µg/mL (95% CI: 9.2175-11.2938) for 30 participants treated in Cohort 1a (25 mg/m2) and was 10.2282 µg/mL (95% CI: 7.1852-13.2712) for 17 participants treated in Cohort 1b (37.5 mg/m2), which are consistent with literature reported values (Tong 2014). For most participants, complete depletion of plasma asparagine was observed in a majority of samples, ie, plasma asparagine levels were rapidly depleted from the predose levels to levels below or near the assay lower limit of quantitation (0.025 µg/mL), and lasted throughout the treatment duration of Course 1 up to predose 6, where the last sample was collected. Four participants had transient low level increases in asparagine (3 from Cohort 1a and 1 from Cohort 1b).

Preliminary Safety Results: In Cohort 1a, a total of 31 participants have been dosed with JZP-458 IM 25 mg/m2. In Cohort 1b, data is available for 17 participants dosed with JZP-458 IM 37.5 mg/m2.

An overview of TEAEs is presented by dose cohort in FIG. 28. The majority of participants have experienced at least 1 TEAE. In the JZP-458 IM 25 mg/m2 cohort, the most frequent TEAEs have been neutrophil count decreased (32.3% of participants, 10/31), white blood cell count decreased (25.8% of participants, 8/31), and anemia (22.6% of participants, 7/31) (Table 4, Cohort 1a). In the JZP-458 IM 37.5 mg/m2 cohort, the most frequent TEAEs have been vomiting (35.3% of participants, 6/17) and nausea (23.5% of participants, 4/17) (FIG. 27, Cohort 1b).

In the JZP-458 IM 25 mg/m2 cohort (N=31), Grade 3 or 4 TEAEs have been reported in 18 participants (58.1%), with Grade 3 or 4 TEAEs of neutrophil count decreased (29.0%), white blood cell count decreased (16.1%), and febrile neutropenia (19.4%) being the most common (Table 6). Overall, a Grade 3 or higher treatment-emergent, unanticipated, clinically significant nonhematologic toxicity has been reported in 1 participant (Grade 4 hypertriglyceridemia, deemed related to study drug) (Table 6 and Listing 1, Cohort 1a). Serious TEAEs have been reported in 9 participants (29.0%) in the JZP-458 IM 25 mg/m2 cohort (Table 5). Serious TEAEs included presyncope in 1 participant; rhinorrhea and febrile neutropenia in 1 participant; febrile neutropenia, dehydration, and pyrexia in 1 participant; drug hypersensitivity and febrile neutropenia in 1 participant; febrile neutropenia in 1 participant; febrile neutropenia and stomatitis in 1 participant; worsening mucositis oral in 1 participant; pyrexia in 1 participant; and methemoglobinemia in 1 participant. All of these serious TEAEs were considered not related to study drug, except for the events of drug hypersensitivity and febrile neutropenia in 1 participant.

Overall, 1 participant (JZP-458 25 mg/m2) has experienced a TEAE leading to discontinuation of study drug. The participant (4 years of age) presented with a Grade 2 allergic reaction (nonserious) to cefepime and sulfamethoxazole/trimethoprim on the day of Dose 5 of Course 1.

Both of these drugs were discontinued. Subsequently, 1 day after receiving Dose 3 of Course 2 of JZP-458, the participant experienced a serious TEAE of drug hypersensitivity (Grade 3). The next day, the event resolved and the participant was discharged. This event was considered related to study drug and led to discontinuation of study drug (Listing 1, Cohort 1a). In the JZP-458 IM 37.5 mg/m2 cohort (N=17), 6 participants have experienced Grade 3 or 4 TEAEs, with febrile neutropenia (17.6%, 3/17) being the most common (FIG. 30 and Listing 1, Cohort 1b). Three participants in the JZP-458 IM 37.5 mg/m2 cohort have experienced serious TEAEs (vomiting and abdominal pain [not related to study drug] in 1 participant; drug hypersensitivity [verbatim term: allergic reaction to JZP-458; related to study drug] and febrile neutropenia in 1 participant [related to study drug]; and febrile neutropenia [related to study drug; 2 events] in 1 participant) (FIG. 28). No Grade 3 or higher treatment-emergent, unanticipated, clinically significant non-hematologic toxicity event has been reported in these participants and no TEAEs have led to study discontinuation (FIG. 29, Cohort 1b).

Adverse events of interest for asparaginase include allergic reactions, pancreatitis, and thrombosis (Stock 2011; Kearney 2009; Pieters 2011; Plourde 2014; Kloos 2020; Asparlas, Summary Basis of Approval 2018). As of the data cutoff for this preliminary safety analysis, only 1 participant (Cohort 1a) has experienced a ≥Grade 3 allergic reaction/hypersensitivity (discussed above) and no participant has experienced an event of ≥Grade 3 pancreatitis or thrombosis. No deaths have been reported.

In summary, the TEAE profile observed is consistent with other asparaginases, and showed that both dose levels of JZP-458 (25 and 37.5 mg/m2) were well tolerated in participants.

Based on a complete review of the available study data by internal and external experts on the SDRC an IM JZP-458 dose of 37.5 mg/m2 is the appropriate dose for registration of JZP-458, with a favorable benefit:risk profile. This dose may ensure patients complete their treatment regimen of asparaginase and is in line with FDA guidance on benefit:risk and minimum effective dosing.

Safety: A further safety study will be conducted with a minimum of 82 participants, including 31 from Cohort 1a (25 mg/m2) and 51 from Cohort 1 b (37.5 mg/m2), will be available for safety evaluation. Preliminary data on 47 participants (31 participants at 25 mg/m2 and 17 participants at 37.5 mg/m2) demonstrated that the proposed dose of 37.5 mg/m2 is safe and well tolerated. In a preliminary safety analysis, only 1 participant (Cohort 1a, 25 mg/m2) experienced a ≥Grade 3 allergic reaction/hypersensitivity and no participant experienced an event of ≥ Grade 3 pancreatitis or thrombosis. The Grade 3 serious adverse event (SAE) of drug hypersensitivity (related to study drug) led to discontinuation of study drug; no other participant has discontinued from the study due to a TEAE.

Efficacy Data: The standard for early efficacy assessment was based on the target SAA value of 0.1 IU/mL, as well as confirmation of asparagine depletion and consideration of a clinically appropriate response rate for patients with previous exposure to an asparaginase. Preliminary observed SAA results show that at JZP-458 IM dose level of 25 mg/m$^2$ (N=26 evaluable participants), the mean (95% CI) SAA levels at the last 72 and 48 hours postdose were 0.1560 (0.1144-0.1976) and 0.4504 (0.3637-0.5370), respectively (median [Q1, Q3] SAA levels at the last 72 and 48 hours postdose were 0.1345 [0.0886, 0.2178] and 0.4091 [0.2813, 0.6577], respectively). At JZP-458 IM dose level of 37.5 mg/m$^2$ (N=16 evaluable participants), the mean (95% CI) SAA levels at the last 72 and 48 hours postdose were 0.2605 (0.1326-0.3884) and 0.7146 (0.3976-1.0316), respectively (median [Q1, Q3] SAA levels at the last 72 and 48 hours postdose were 0.1732 [0.1157, 0.2849] and 0.6503 [0.3248, 0.8736], respectively).

At JZP-458 IM dose levels of 25 and 37.5 mg/m$^2$, 65.4% and 81.3% of participants, respectively, achieved NSAA levels ≥0.1 IU/mL at the last 72-hour assessment (primary endpoint); and 96.2% and 93.8% of participants, respectively, achieved NSAA levels ≥0.1 IU/mL at the last 48-hour assessment (key secondary endpoint). At 37.5 mg/m$^2$ (N=16), while the percentage of participants achieving NSAA levels ≥0.1 IU/mL at the last 72-hour assessment did not meet the primary endpoint criteria (as defined in the statistical analysis plan [SAP]), the results demonstrate clinically appropriate response rates consistent with published observed or predicted rates (80% to 88%) for patients who received non-E. coli-based asparaginase for treatment following hypersensitivity reactions (Vrooman 2010; Panetta 2020; Salzer 2013). At 37.5 mg/m$^2$ (N=16), the percentage of participants achieving NSAA levels ≥0.1 IU/mL at the last 48-hour assessment (secondary key endpoint) was 93.8% and is expected to meet the prespecified success criteria outlined in the SAP for the IA (planned for N=51 participants).

Additional confirmation of the efficacy of JZP-458 is demonstrated in the preliminary PPK results. Preliminary PPK were consistent with observed data and provide additional support for the proposed 37.5 mg/m2 dose selection. Based on the PPK modeling and simulation (secondary endpoint), at an IM dose of 37.5 mg/m$^2$ JZP-458 on a FMW schedule, JZP-458 is expected to achieve the last 72-hour NSAA level ≥0.1 IU/mL in 87% of patients (95% CI: 85.5%-88.5%) and to achieve the last 48-hour NSAA level ≥0.1 IU/mL in 99.9% of patients (95% CI: 99.7%-100%); the simulated mean NSAA levels were 0.29 (95% prediction interval: 0.06-0.88) and 0.58 (95% prediction interval: 0.2-1.32) at the last 72 and 48 hours, respectively. Simulation results indicated that start day does not impact the percentage of patients with NSAA levels ≥0.1 IU/mL for the last 72- or 48-hour time points.

The PPK analysis provides robust support of the observed data and for the total data package for the BLA because the model uses available data across all patients, time points, and dose levels. The PPK model results, based on all clinical and PK data available, can illustrate the exposure-response characteristics of JZP-458. As this model does not depend on categorized data, it provides reliable predictions of NSAA levels at the relevant times. The model demonstrates that the percentage of patients with 72-hour NSAA level ≥0.1 IU/mL after JZP-458 IM administration is consistent with the response expected in a population of patients with hypersensitivity to *E. coli*-based asparaginase product. The modeled SAA values suggests that an IM dose of 37.5 mg/m² is an appropriate dose on a MWF dosing schedule.

As further measure of the confirmed 37.5 mg/m² dose for JZP-458, the goal of total asparagine depletion as measured by the validated method (Biomarker Partial Validation Report Amendment 1, SN 0044) was achieved. A comparison of baseline asparagine levels to those measured at trough throughout the dosing period at 25 and 37.5 mg/m² consistently demonstrated near complete depletion of asparagine. Deviations from this pattern were small and transient. The effects of potential doses, toxicity studies, the effect of number of injections, number of vials, as well as other factors were evaluated. Such studies balanced higher doses with potential effect of increased risk of higher adverse events.

While embodiments and applications of the present invention have been described in some detail by way of illustration and example, it would be apparent to those of skill in the art that many additional modifications would be possible without departing from the inventive concepts contained herein. All references cited herein are hereby incorporated in their entirety.

---

The invention claimed is:

1. A method of treating a disease characterized by benefiting from asparagine depletion in a human subject, the method comprising intramuscularly administering to the human subject a pharmaceutical composition having a pH of about 7.0 and comprising:
   (i) a recombinant L-asparaginase; and
   (ii) trehalose,
   wherein the recombinant L-asparaginase is a tetramer,
   wherein the tetramer comprises four monomers,
   wherein each monomer has an amino acid sequence comprising SEQ ID NO: 1,
   wherein the recombinant L-asparaginase in the pharmaceutical composition demonstrates less than 5% aggregation, and
   wherein the treatment results in asparagine depletion in the subject, thereby treating the disease.

2. The method according to claim 1, wherein the recombinant L-asparaginase demonstrates less than 4% aggregation.

3. The method according to claim 1, wherein the recombinant L-asparaginase demonstrates less than 1% aggregation.

4. The method according to claim 1, wherein the recombinant L-asparaginase is recombinantly produced in *Pseudomonas fluorescens*.

5. The method according to claim 4, wherein the recombinant L-asparaginase is administered every other day over a period of 5 consecutive days followed by a rest period of 2 consecutive days.

6. The method according to claim 1, wherein the recombinant L-asparaginase is administered every 48 hours in an amount of 25 mg/m$^2$ for two weeks.

7. The method according to claim 1, wherein the recombinant L-asparaginase is administered every other day over a period of 5 consecutive days followed by a rest period of 2 consecutive days.

8. The method according to claim 1, wherein the recombinant L-asparaginase demonstrates less than 3% aggregation.

9. The method according to claim 1, wherein the recombinant L-asparaginase is recombinantly produced in a host cell of the order Pseudomonadales.

10. The method according to claim 1, wherein the pharmaceutical composition comprises about 6.4% of trehalose.

11. The method according to claim 1, wherein the pharmaceutical composition further comprises sodium phosphate.

12. The method according to claim 1, wherein the disease is acute lymphoblastic leukemia (ALL).

13. The method according to claim 1, wherein the disease is lymphoblastic lymphoma (LBL).

14. The method according to claim 1, wherein the disease is colon carcinoma, colon adenocarcinoma, or colorectal adenocarcinoma.

15. The method according to claim 1, wherein the human subject has previously experienced silent inactivation of an *E. coli*-derived asparaginase.

16. The method according to claim 1, wherein the human subject has previously experienced an allergic reaction to an *E. coli*-derived asparaginase.

17. The method according to claim 1, wherein the human subject has a nadir serum asparaginase activity level of at least about 0.1 IU/mL following the administration.

18. The method of claim 1, wherein the pharmaceutical composition further comprises sodium chloride and sodium phosphate.

19. A method of treating a disease characterized by benefiting from asparagine depletion in a human subject comprising intramuscularly administering to the human subject a dose regimen of a pharmaceutical composition having a pH of about 7.0 and comprising a recombinant L-asparaginase and trehalose,
wherein the recombinant L-asparaginase is a tetramer,
wherein the dose regimen of the pharmaceutical composition comprises a cycle,
wherein the cycle comprises a first dose, a second dose and a third dose,
wherein the first dose, the second dose, and the third dose each independently comprise about 25 mg/m$^2$ or 50 mg/m$^2$ of the recombinant L-asparaginase,
wherein the cycle is optionally repeatable, and
wherein the first dose, second dose, and third dose are administered about 48-72 hours apart.

20. The method according to claim 19, wherein the pharmaceutical composition is administered three times a week.

21. The method according to claim 19, wherein the pharmaceutical composition is administered for 2 weeks.

22. The method according to claim 19, wherein the first dose and the second dose are each administered in an amount of about 25 mg/m$^2$.

23. The method according to claim 19, wherein the third dose is administered in an amount of about 50 mg/m$^2$.

24. The method according to claim 19, wherein the first dose is administered on Monday, the second dose is administered on a Wednesday, and the third dose is administered on a Friday of the same week.

25. The method according to claim 19, wherein the recombinant L-asparaginase comprises SEQ ID NO:1.

26. The method according to claim 19, wherein the disease is acute lymphoblastic leukemia (ALL).

27. The method according to claim 19, wherein the disease is lymphoblastic lymphoma (LBL).

28. The method according to claim 19, wherein the disease is colon carcinoma, colon adenocarcinoma, or colorectal adenocarcinoma.

29. The method of claim 19, wherein the third dose is larger than the first dose and the second dose.

30. The method of claim 29, wherein the cycle is repeated at least once, the first dose and the second dose are administered about 48 hours apart, the second and the third dose are administered about 48 hours apart, and the third dose is administered about 72 hours before the first dose of a subsequent cycle.

31. The method of claim 19, wherein the dose regimen comprises about 25 mg/m$^2$ of the recombinant L-asparaginase.

32. The method of claim 19, wherein the pharmaceutical composition further comprises sodium chloride and sodium phosphate.

* * * * *

SEQUENCE LISTING

```
<160> NUMBER OF SEQ ID NOS: 3

<210> SEQ ID NO 1
<211> LENGTH: 327
<212> TYPE: PRT
<213> ORGANISM: Artificial Sequence
<220> FEATURE:
<223> OTHER INFORMATION: Synthetic protein

<400> SEQUENCE: 1

Ala Asp Lys Leu Pro Asn Ile Val Ile Leu Ala Thr Gly Gly Thr Ile
1               5                   10                  15

Ala Gly Ser Ala Ala Thr Gly Thr Gln Thr Thr Gly Tyr Lys Ala Gly
            20                  25                  30

Ala Leu Gly Val Asp Thr Leu Ile Asn Ala Val Pro Glu Val Lys Lys
        35                  40                  45

Leu Ala Asn Val Lys Gly Glu Gln Phe Ser Asn Met Ala Ser Glu Asn
    50                  55                  60

Met Thr Gly Asp Val Val Leu Lys Leu Ser Gln Arg Val Asn Glu Leu
65                  70                  75                  80

Leu Ala Arg Asp Asp Val Asp Gly Val Val Ile Thr His Gly Thr Asp
                85                  90                  95

Thr Val Glu Glu Ser Ala Tyr Phe Leu His Leu Thr Val Lys Ser Asp
            100                 105                 110

Lys Pro Val Val Phe Val Ala Ala Met Arg Pro Ala Thr Ala Ile Ser
        115                 120                 125

Ala Asp Gly Pro Met Asn Leu Leu Glu Ala Val Arg Val Ala Gly Asp
    130                 135                 140

Lys Gln Ser Arg Gly Arg Gly Val Met Val Val Leu Asn Asp Arg Ile
145                 150                 155                 160

Gly Ser Ala Arg Tyr Ile Thr Lys Thr Asn Ala Ser Thr Leu Asp Thr
                165                 170                 175

Phe Lys Ala Asn Glu Glu Gly Tyr Leu Gly Val Ile Ile Gly Asn Arg
            180                 185                 190

Ile Tyr Tyr Gln Asn Arg Ile Asp Lys Leu His Thr Thr Arg Ser Val
        195                 200                 205

Phe Asp Val Arg Gly Leu Thr Ser Leu Pro Lys Val Asp Ile Leu Tyr
    210                 215                 220

Gly Tyr Gln Asp Asp Pro Glu Tyr Leu Tyr Asp Ala Ala Ile Gln His
225                 230                 235                 240

Gly Val Lys Gly Ile Val Tyr Ala Gly Met Gly Ala Gly Ser Val Ser
                245                 250                 255

Val Arg Gly Ile Ala Gly Met Arg Lys Ala Met Glu Lys Gly Val Val
            260                 265                 270
```

-continued

```
Val Ile Arg Ser Thr Arg Thr Gly Asn Gly Ile Val Pro Pro Asp Glu
            275                 280                 285

Glu Leu Pro Gly Leu Val Ser Asp Ser Leu Asn Pro Ala His Ala Arg
        290                 295                 300

Ile Leu Leu Met Leu Ala Leu Thr Arg Thr Ser Asp Pro Lys Val Ile
305                 310                 315                 320

Gln Glu Tyr Phe His Thr Tyr
                325

<210> SEQ ID NO 2
<211> LENGTH: 20
<212> TYPE: PRT
<213> ORGANISM: Artificial Sequence
<220> FEATURE:
<223> OTHER INFORMATION: Synthetic protein

<400> SEQUENCE: 2

Ala Ala Pro Ala Ala Pro Ala Pro Ala Ala Pro Ala Ala Pro Ala Pro
1               5                   10                  15

Ala Ala Pro Ala
            20

<210> SEQ ID NO 3
<211> LENGTH: 6
<212> TYPE: PRT
<213> ORGANISM: Artificial Sequence
<220> FEATURE:
<223> OTHER INFORMATION: Synthetic RBS amino acid sequence

<400> SEQUENCE: 3

Ala Gly Gly Ala Gly Gly
1               5
```